(12) United States Patent
Ge et al.

(10) Patent No.: US 9,062,037 B2
(45) Date of Patent: Jun. 23, 2015

(54) TAZAROTENE DERIVATIVES

(71) Applicant: Stiefel Laboratories, Inc., Wilmington, New Castle, DE (US)

(72) Inventors: Xue Ge, Palo Alto, CA (US); Hansen Wong, Sunnyvale, CA (US); Wendy Huang Chern, Palo Alto, CA (US); Hans Hofland, Palo Alto, CA (US); Michael J. Bishop, Research Triangle Park, NC (US); Xin Frank Cai, Palo Alto, CA (US); Alan Colborn, Research Triangle Park, NC (US)

(73) Assignee: Stiefel Laboratories, Inc., Wilmington, New Castle, DE (US)

( * ) Notice: Subject to any disclaimer, the term of this patent is extended or adjusted under 35 U.S.C. 154(b) by 0 days.

(21) Appl. No.: 14/463,985

(22) Filed: Aug. 20, 2014

(65) Prior Publication Data

US 2014/0357672 A1 Dec. 4, 2014

Related U.S. Application Data

(63) Continuation of application No. 13/383,869, filed as application No. PCT/US2010/042225 on Jul. 16, 2010, now abandoned.

(60) Provisional application No. 61/272,257, filed on Sep. 4, 2009, provisional application No. 61/213,794, filed on Jul. 16, 2009.

(51) Int. Cl.
| | |
|---|---|
| *A61K 31/4436* | (2006.01) |
| *C07D 409/06* | (2006.01) |
| *C07D 409/14* | (2006.01) |
| *A61K 31/05* | (2006.01) |
| *A61K 31/38* | (2006.01) |
| *A61K 31/593* | (2006.01) |
| *A61K 45/06* | (2006.01) |
| *A61K 31/327* | (2006.01) |
| *A61K 31/444* | (2006.01) |
| *A61K 9/00* | (2006.01) |

(52) U.S. Cl.
CPC ............ *C07D 409/14* (2013.01); *A61K 31/05* (2013.01); *A61K 31/38* (2013.01); *A61K 31/593* (2013.01); *A61K 45/06* (2013.01); *C07D 409/06* (2013.01); *A61K 31/327* (2013.01); *A61K 31/4436* (2013.01); *A61K 31/444* (2013.01); *A61K 9/0014* (2013.01)

(58) Field of Classification Search
CPC .......................... C07D 409/06; A61K 31/4436
USPC ........................................ 546/280.1; 514/337
See application file for complete search history.

(56) References Cited

U.S. PATENT DOCUMENTS

| | | |
|---|---|---|
| 4,801,593 A | 1/1989 | Hodson et al. |
| 4,980,369 A | 12/1990 | Chandraratna |
| 5,045,551 A | 9/1991 | Chandraratna |
| 5,162,546 A | 11/1992 | Chandraratna |
| 5,183,827 A | 2/1993 | Chandraratna |
| 5,272,156 A | 12/1993 | Chandraratna |
| 5,278,318 A | 1/1994 | Chandraratna |
| 5,346,895 A | 9/1994 | Chandraratna |
| 5,346,915 A | 9/1994 | Chandraratna |
| 5,399,561 A | 3/1995 | Chandraratna |
| 5,407,937 A | 4/1995 | Chandraratna |
| 5,534,516 A | 7/1996 | Chandraratna |
| 5,599,819 A | 2/1997 | Chandraratna |
| 5,616,597 A | 4/1997 | Chandraratna |
| 5,677,323 A | 10/1997 | Chandraratna |
| 6,048,902 A | 4/2000 | Lebwohl et al. |
| 6,096,765 A | 8/2000 | Bershad |
| 6,448,233 B1 | 9/2002 | Lefevre et al. |
| 7,273,937 B2 | 9/2007 | Frigoli et al. |
| 2005/0002878 A1 | 1/2005 | Lefrancois et al. |
| 2009/0318371 A1 | 12/2009 | Ahumada Ayala |

FOREIGN PATENT DOCUMENTS

| | | |
|---|---|---|
| WO | WO 92/06084 A1 | 4/1992 |
| WO | WO 92/14725 A1 | 9/1992 |
| WO | WO 92/17471 A1 | 10/1992 |
| WO | WO 95/18803 A1 | 7/1995 |

*Primary Examiner* — Patricia L Morris

(74) *Attorney, Agent, or Firm* — Dara L. Dinner; Theodore Furman

(57) ABSTRACT

The presently described subject matter relates to new derivatives of tazarotene that also exhibit retinoid activity, pharmaceutical compositions comprising the derivatives, method of treating skin disorders with the pharmaceutical compositions, and process of making the derivatives.

22 Claims, 30 Drawing Sheets

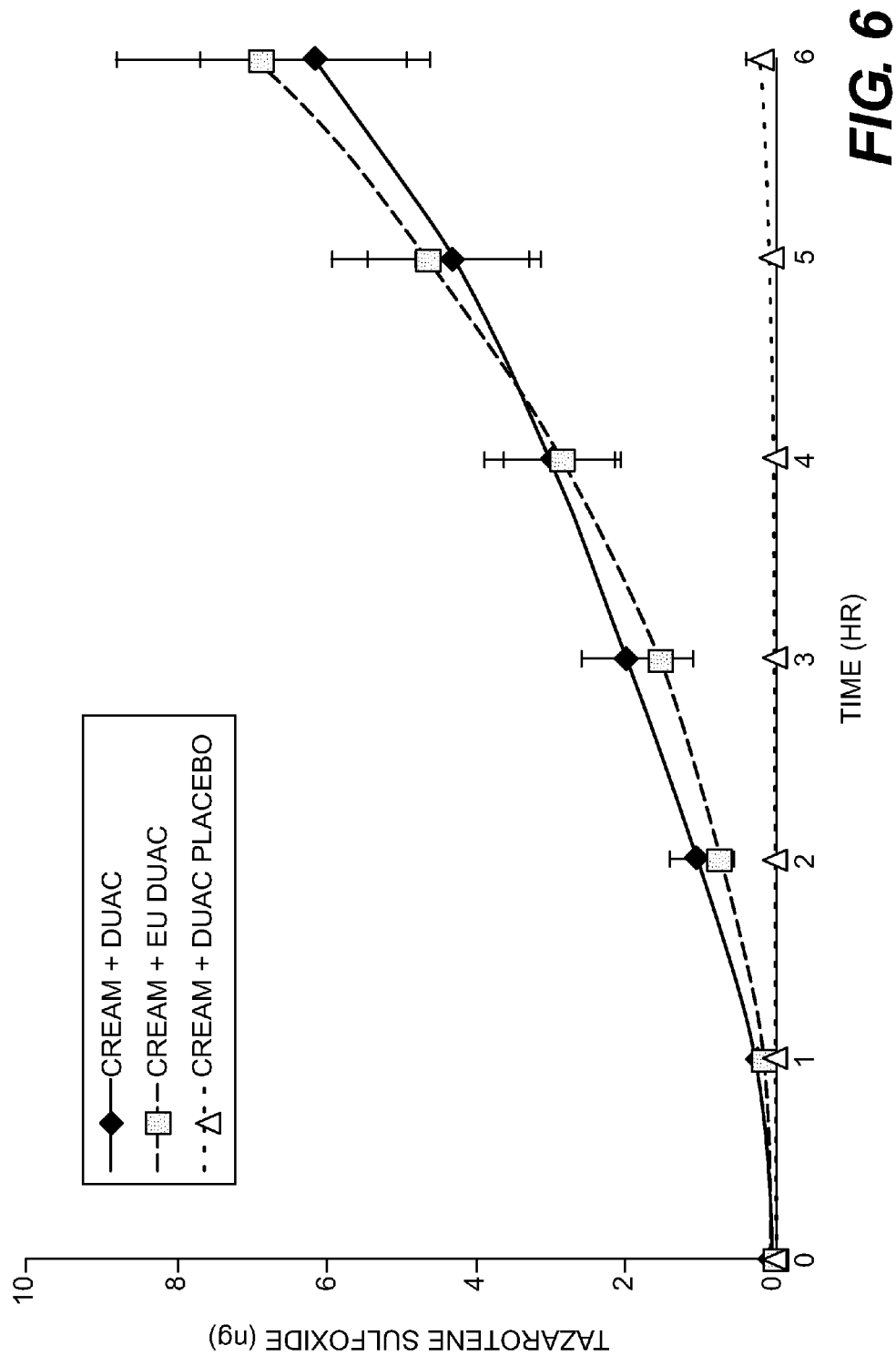

TAZAROTENE DERIVATIVES

FIELD OF THE INVENTION

The present invention relates to derivatives of tazarotene.

BACKGROUND OF THE INVENTION

Tazarotene has the chemical name: ethyl 6-[2-(4,4-dimethylthiochroman-6-yl)-ethynyl nicotinate. Tazarotene is a retinoid prodrug which is converted to its active form, tazarotenic acid, by rapid de-esterification in most biological systems. Tazarotenic acid binds to all three members of the retinoic acid receptor (RAR) family; $RAR_\alpha$, $RAR_\beta$, and $RAR_\gamma$, but has relative selectivity for $RAR_\beta$ and $RAR_\gamma$, and may modify gene expression.

Allergan, Inc. market TAZORAC® (tazarotene) cream and TAZORAC® (tazarotene) gel for the treatment of acne and psoriasis.

The treatment of skin disorders using a retinoid or an antibiotic in combination with benzoyl peroxide is of great interest to dermatologists. However, this presents challenges to the formulation chemist insofar as retinoids and antibiotics often readily degrade in the presence of benzoyl peroxide. Accordingly, the active ingredients are often not mixed together until immediately before administration to the patient, or are administered at different times of the day. Alternatively, the retinoid or antibiotic might be protected (e.g. by encapsulation) from reaction with the benzoyl peroxide, or the active ingredients may be housed in separate chambers of a dual chamber dispenser.

Thus, there is a need for improved dermatological compositions containing a combination of active ingredients which provide the requisite convenience, efficacy and shelf life. Specifically, a need exists for the identification of stable retinoids that may be combined with benzoyl peroxide in a pharmaceutical composition.

SUMMARY OF THE INVENTION

The present invention is directed to new derivatives of tazarotene that penetrate the skin and exhibit retinoid-like activity.

According to an embodiment, the present invention provides for a compound of general formula (I):

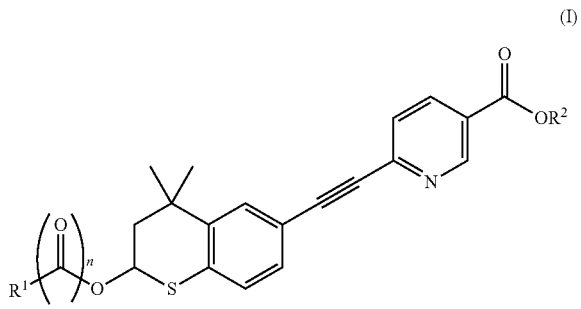

wherein n is 0 or 1;
$R^1$ is hydrogen, optionally substituted $C_{1-18}$ alkyl, optionally substituted $C_{2-18}$ alkenyl, optionally substituted $C_{2-18}$ alkynyl, optionally substituted aryl group, optionally substituted heterocyclic group, optionally substituted cycloalkyl group, or an optionally substituted heteroaryl group; and $R^2$ is hydrogen, optionally substituted $C_{1-18}$ alkyl, optionally substituted $C_{2-18}$ alkenyl, optionally substituted $C_{2-18}$ alkynyl, optionally substituted aryl group, optionally substituted heterocyclic group, optionally substituted cycloalkyl group, or an optionally substituted heteroaryl group; or a pharmaceutically acceptable salt thereof.

According to another embodiment, the present invention provides a compound of formula (II):

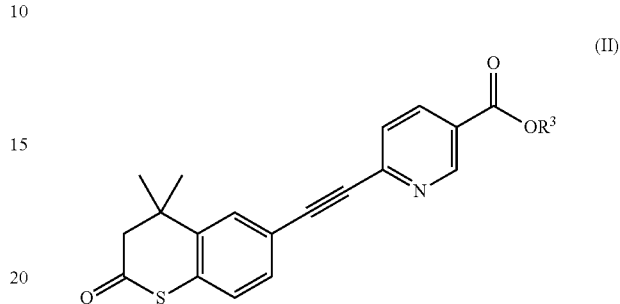

wherein
$R^3$ is hydrogen, optionally substituted $C_{1-18}$ alkyl, optionally substituted $C_{2-18}$ alkenyl, optionally substituted $C_{2-18}$ alkynyl, optionally substituted aryl group, optionally substituted heterocyclic group, optionally substituted cycloalkyl group, or an optionally substituted heteroaryl group; or a pharmaceutically acceptable salt thereof.

According to another embodiment, the present invention provides a pharmaceutical composition comprising a compound of Formula (I) or (II), or a pharmaceutically acceptable salt thereof, and one or more pharmaceutically acceptable excipients.

In a further embodiment, the present invention provides a method of treating a skin disorder in a subject, the method comprising administering a composition comprising a therapeutically effective amount of a compound of Formula (I) or (II), or a pharmaceutically acceptable salt thereof, and one or more pharmaceutically acceptable excipients, to a subject in need thereof.

In an embodiment, the present invention relates to the use of a compound of Formula (I) or (II), or a pharmaceutically acceptable salt thereof, for the preparation of a medicament for the treatment of a skin disorder.

In another embodiment, the present invention relates to the use of a compound of Formula (I) or (II), or a pharmaceutically acceptable salt thereof, for the treatment of a skin disorder.

BRIEF DESCRIPTION OF DRAWINGS

FIG. 6 illustrates skin penetration from mixtures of DUAC gel and TAZORAC cream. The data points represent the cumulative amount of tazarotene sulfoxide from at least 4 replicates from 4 donors (n≥18)±SEM.

DETAILED DESCRIPTION OF THE INVENTION

Figure 1:
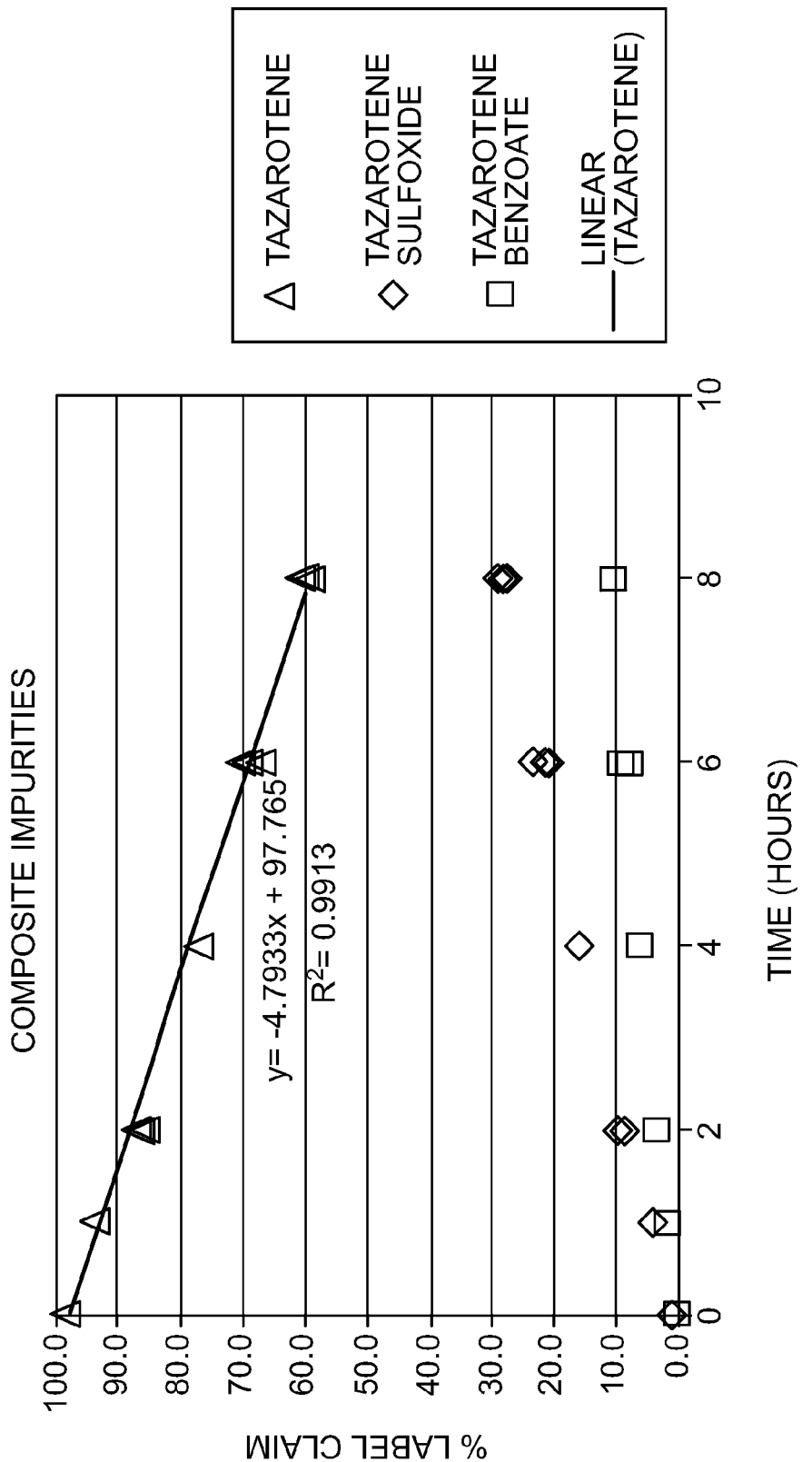
FIG. 1 illustrates the degradation of tazarotene into its degradation products when DUAC® gel and TAZORAC® cream are mixed together. The degradation was observed over 8 hours once "fresh" samples of DUAC gel and TAZORAC cream were mixed.

According to an embodiment, the present invention provides a compound of general formula (I):

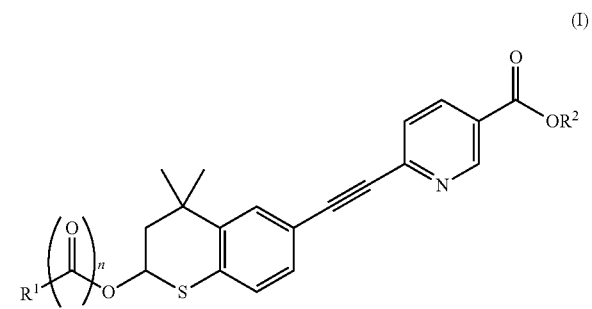

(I)

wherein n is 0 or 1;

$R^1$ is hydrogen, optionally substituted $C_{1-18}$ alkyl, optionally substituted $C_{2-18}$ alkenyl, optionally substituted $C_{2-18}$ alkynyl, optionally substituted aryl group, optionally substituted heterocyclic group, optionally substituted $C_{3-7}$ cycloalkyl group, or an optionally substituted heteroaryl group; and $R^2$ is hydrogen, optionally substituted $C_{1-18}$ alkyl, optionally substituted $C_{2-18}$ alkenyl, optionally substituted $C_{2-18}$ alkynyl, optionally substituted aryl group, optionally substituted heterocyclic group, optionally substituted $C_{3-7}$ cycloalkyl group, or an optionally substituted heteroaryl group; or a pharmaceutically acceptable salt thereof.

Suitably, n is 0 or an integer having a value of 1. In one embodiment, n is 1. In another embodiment n is 0. In one embodiment, n is 0, and $R^1$ is hydrogen.

Suitably, $R^1$ is hydrogen, optionally substituted $C_{1-18}$ alkyl, optionally substituted $C_{2-18}$ alkenyl, optionally substituted $C_{2-18}$ alkynyl, optionally substituted aryl group, optionally substituted heterocyclic group, optionally substituted $C_{3-7}$ cycloalkyl group, or an optionally substituted heteroaryl group.

Suitably, $R^2$ is hydrogen, optionally substituted $C_{1-18}$ alkyl, optionally substituted $C_{2-18}$ alkenyl, optionally substituted $C_{2-18}$ alkynyl, optionally substituted aryl group, optionally substituted heterocyclic group, optionally substituted $C_{3-7}$ cycloalkyl group, or an optionally substituted heteroaryl group.

When $R^1$ is an optionally substituted $C_{1-18}$ alkyl, $C_{2-18}$ alkenyl, $C_{2-18}$ alkynyl, aryl, heterocyclic, cycloalkyl or heteroaryl group, the group is optionally substituted one or more times, preferably 1 to 4 times independently by halogen; hydroxy; $NR_4R_5$; hydroxy substituted $C_{1-6}$ alkyl; $C_{1-6}$ alkoxy, such as methoxy or ethoxy; halosubstituted $C_{1-6}$ alkoxy, halosubstituted $C_{1-6}$ alkyl, such as $CF_2CF_2H$ or $CF_3$; $C_{1-6}$ alkyl such as methyl, ethyl, isopropyl etc.; —C(O)OR$_6$, or —OC(O)R$_6$. In one embodiment, the optional substituents are selected from hydroxy, $NR_4R_5$, or hydroxy substituted $C_{1-6}$ alkyl, or —C(O)OR$_6$.

Suitably, $R_4$ and $R_5$ are independently selected from hydrogen or $C_{1-6}$ alkyl. In one embodiment both $R_4$ and $R_5$ are hydrogen.

Suitably, $R_6$ is independently selected from hydrogen or $C_{1-6}$ alkyl. In one embodiment $R_6$ is $C_{1-6}$ alkyl. In another embodiment the $C_{1-6}$ alkyl is methyl.

Suitably, when $R^1$ or $R^2$ is an optionally substituted aryl group, the aryl is an aromatic cyclic hydrocarbon group of from 5 to 20 carbon atoms having a single ring (e.g., phenyl) or multiple condensed (fused) rings, such as naphthyl, indene or anthryl. In one embodiment the aryl group is an optionally substituted phenyl, naphthyl or indene. In another embodiment the $R^1$ aryl group is an optionally substituted phenyl or naphthyl. In another embodiment, $R^1$ is an optionally substituted phenyl. In another embodiment, $R^1$ is phenyl or hydroxy substituted phenyl.

Suitably, when $R^1$ or $R^2$ is an optionally substituted heteroaryl group, the heteroaryl ring is a monocyclic five- to seven-membered unsaturated aromatic hydrocarbon ring containing at least one heteroatom selected from oxygen, nitrogen and sulfur. Suitable rings include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, or uracil. The heteroaryl group may also include fused aromatic rings comprising at least one heteroatom selected from oxygen, nitrogen and sulfur. Each of the fused rings contains five or six ring atoms. Suitable examples of fused aromatic rings include, but are not limited to, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl or phthalazinyl.

In one embodiment, when $R^1$ is an optionally substituted heteroaryl group, the heteroaryl is an optionally substituted 2-, 3- or 4-pyridyl or pyranyl ring. In another embodiment the heteroaryl is an optionally substituted 2-, 3- or 4-pyridyl. In another embodiment $R^1$ is an optionally substituted pyrid-3-yl.

Suitably, when $R^1$ or $R^2$ is an optionally substituted heterocyclic group, the heterocyclic ring is a monocyclic three- to seven-membered saturated or non-aromatic, unsaturated hydrocarbon ring containing at least one heteroatom selected from nitrogen, oxygen, sulphur or oxidized sulphur moieties, such as S(O)m, and m is 0 or an integer having a value of 1 or 2. The heterocyclic group may also include fused rings, saturated or partially unsaturated, and wherein one of the rings may be aromatic or heteroaromatic. Each of the fused rings may have from four to seven ring atoms. Suitable examples of heterocyclyl groups include, but are not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), azepine, diazepine, aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety).

Suitably, when $R^1$ is an optionally substituted heterocyclic group, the heterocyclic is an optionally substituted piperidinyl, piperazinyl, tetrahydropyranyl or tetrahydrofuranyl ring. In one embodiment the heterocyclic ring is an optionally substituted 2-, 3- or 4-piperidinyl. In one embodiment the 2-, 3- or 4-piperidinyl is substituted by a $C_{1-6}$ alkyl. In one embodiment, the $C_{1-6}$ alkyl is methyl. In another embodiment $R^1$ is a 4-methylpiperidin-4-yl group.

In one embodiment, $R^1$ is an optionally substituted $C_{1-18}$ alkyl. In an embodiment, $R^1$ is a $C_{1-18}$ alkyl optionally substituted, independently, one or more times by hydroxy, $NR_4R_5$, $C_{1-6}$ alkoxy, or —C(O)OR$_6$. In another embodiment the $C_{1-18}$ alkyl is unsubstituted. In another embodiment $R^1$ is a $C_{1-3}$ alkyl or a $C_{15}$ alkyl. In another embodiment $R^1$ is a $C_{1-3}$ alkyl. In another embodiment the $C_{1-18}$ alkyl is substituted by —C(O)OR$_6$. In another embodiment, $R_6$ is a $C_{1-6}$ alkyl, preferably methyl.

In one embodiment, $R^1$ is an optionally substituted $C_{2-18}$ alkenyl.

In another embodiment, $R^1$ is an optionally substituted aryl, heteroaryl or heterocyclic group.

In another embodiment, $R^1$ is selected from an optionally substituted $C_{1-18}$ alkyl, a $C_{2-18}$ alkenyl, optionally substituted phenyl, optionally substituted pyridinyl, optionally substituted tetrahydropyranyl, or optionally substituted piperidinyl. In a further embodiment, $R^1$ is selected from an optionally substituted phenyl, optionally substituted pyridinyl, optionally substituted tetrahydropyranyl, or optionally substituted piperidinyl group.

When $R^2$ is an optionally substituted $C_{1-18}$ alkyl, $C_{2-18}$ alkenyl, $C_{2-18}$ alkynyl, aryl, heterocyclic, cycloalkyl or heteroaryl group, the group is optionally substituted one or more times, preferably 1 to 4 times, independently by halogen; hydroxy; $NR_4R_5$; hydroxy substituted $C_{1-6}$ alkyl; $C_{1-6}$ alkoxy, such as methoxy or ethoxy; halosubstituted $C_{1-6}$ alkoxy; halosubstituted $C_{1-6}$ alkyl, such as $CF_2CF_2H$ or $CF_3$; $C_{1-6}$ alkyl such as methyl, ethyl, isopropyl, etc.; —C(O)OR$_6$ or —OC(O)R$_6$.

In one embodiment $R^2$ is hydrogen or optionally substituted $C_{1-18}$ alkyl. In an embodiment, $R^2$ is hydrogen or optionally substituted $C_{1-6}$ alkyl. In another embodiment, $R^2$ is hydrogen. In another embodiment, $R^2$ is $C_{1-6}$ alkyl. According to a further embodiment, $R^2$ is ethyl.

According to one embodiment, n is 1, $R^1$ is phenyl and $R^2$ is hydrogen or $C_{1-6}$ alkyl. In another embodiment, n is 1, $R^1$ is phenyl and $R^2$ is hydrogen. This compound is known as 6-(2-(2-benzoyloxy-4,4-dimethylthiochroman-6-yl)ethynyl) nicotinic acid, and is also described herein as tazarotenic acid benzoate.

In another embodiment, n is 1, $R^1$ is phenyl and $R^2$ is $C_{1-6}$ alkyl. In one embodiment, the $C_{1-6}$ alkyl is ethyl. This compound is known as 6-(2-(2-benzoyloxy-4,4-dimethylthiochroman-6-yl)ethynyl) nicotinic acid, ethyl ester, and is described herein as tazarotene benzoate.

In another embodiment, the compound is (S)-6-(2-(2-benzoyloxy-4,4-dimethylthiochroman-6-yl)ethynyl) nicotinic acid, ethyl ester. In another embodiment, the compound is (R)-6-(2-(2-benzoyloxy-4,4-dimethylthiochroman-6-yl) ethynyl) nicotinic acid, ethyl ester.

According to a further embodiment, n is 0, $R^1$ is hydrogen and $R^2$ is hydrogen or $C_{1-6}$ alkyl. In an embodiment, $R^2$ is hydrogen. This compound is 6-((2-hydroxy-4,4-dimethylthiochroman-6-yl)ethynyl)nicotinic acid, and is also described herein as hydroxy tazarotenic acid.

In another embodiment, n is 0, $R^1$ is hydrogen and $R^2$ is $C_{1-6}$ alkyl. According to a further embodiment, $C_{1-6}$ alkyl is ethyl. This compound is ethyl 6-[(2-hydroxy-4,4-dimethyl-3,4-dihydro-2-thiochromen-6-yl)ethyynyl]pyridine-3-carboxylate, and is also described herein as hydroxy tazarotene.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

According to an embodiment, a compound of Formula (I), is selected from:

(i) 6-[4,4-dimethyl-2-(pyridine-3-carbonyloxy)thiochroman-6-ylethynyl]nicotinic acid ethyl ester,
(ii) (S)-6-[4,4-dimethyl-2-(pyridine-3-carbonyloxy)thiochroman-6-ylethynyl]nicotinic acid ethyl ester,
(iii) (R)-6-[4,4-dimethyl-2-(pyridine-3-carbonyloxy)thiochroman-6-ylethynyl]nicotinic acid ethyl ester,
(iv) Ethyl 6-[2-palmitoyl-4,4-dimethyl-3,4-dihydro-2-thiochromen-6-yl)ethynyl]pyridine-3-carboxylate,
(v) 6-[2-(2-Hydroxy-acetoxy)-4,4-dimethyl-thiochroman-6-ylethynyl]-nicotinic acid ethyl ester,
(vi) Ethyl 6-[(2-(2-methoxyacetyl)-4,4-dimethyl-3,4-dihydro-2-thiochromen-6-yl) ethynyl]pyridine-3-carboxylate,
(vii) Ethyl 6-[(2-acetyl-4,4-dimethyl-3,4-dihydro-2-thiochromen-6-yl)ethynyl]pyridine-3-carboxylate,
(viii) Ethyl 6-[(2-n-butyryloxyl-4,4-dimethyl-3,4-dihydro-2-thiochromen-6-yl) ethynyl]pyridine-3-carboxylate,
(ix) Ethyl 6-[(2-lauroyl-4,4-dimethyl-3,4-dihydro-2-thiochromen-6-yl)ethynyl]pyridine-3-carboxylate,
(x) Ethyl 6-[(2-isobutyryloxy-4,4-dimethyl-3,4-dihydro-2-thiochromen-6-yl) ethynyl]pyridine-3-carboxylate,
(xi) Ethyl 6-[(2-linoeoyll-4,4-dimethyl-3,4-dihydro-2-thiochromen-6-yl)ethynyl]pyridine-3-carboxylate,
(xii) Ethyl 6-[(2-linleolyl-4,4-dimethyl-3,4-dihydro-2-thiochromen-6-yl)ethynyl]pyridine-3-carboxylate,
(xiii) Ethyl 6-[(2-(N-methyl-4-piperidinylcarboxy-4,4-dimethyl-3,4-dihydro-2-thiochromen-6-yl)ethynyl]pyridine-3-carboxylate,
(xiv) Ethyl 6-[(2-propionyl-4,4-dimethyl-3,4-dihydro-2-thiochromen-6-yl)ethynyl]pyridine-3-carboxylate,
(xv) Ethyl 6-[(2-salicylicyl-4,4-dimethyl-3,4-dihydro-2-thiochromen-6-yl)ethynyl]pyridine-3-carboxylate,
(xvi) Ethyl 6-[(2-(4-pyranyloxy-4,4-dimethyl-3,4-dihydro-2-thiochromen-6-yl) ethynyl]pyridine-3-carboxylate,
(xvii) Ethyl 6-[(2-monomethyladopyl-4,4-dimethyl-3,4-dihydro-2-thiochromen-6-yl) ethynyl]pyridine-3-carboxylate,
(xviii) Ethyl 6-[(2-(3-monomethylazelauate-4,4-dimethyl-3,4-dihydro-2-thiochromen-6-yl)ethynyl]pyridine-3-carboxylate, and
(xix) 6-[2-((S)-2-Amino-3-methyl-butyryloxy)-4,4-dimethyl-thiochroman-6-ylethynyl]-nicotinic acid ethyl ester; or a pharmaceutically acceptable salt thereof.

Suitably, the compound of Formula (I) is 6-[4,4-dimethyl-2-(pyridine-3-carbonyloxy)thiochroman-6-ylethynyl]nicotinic acid ethyl ester, or a pharmaceutically acceptable salt thereof.

Suitably, the compound of Formula (I) is (S)-6-[4,4-dimethyl-2-(pyridine-3-carbonyloxy)thiochroman-6-ylethynyl]nicotinic acid ethyl ester, or a pharmaceutically acceptable salt thereof.

Suitably, the compound of Formula (I) is (R)-6-[4,4-dimethyl-2-(pyridine-3-carbonyloxy)thiochroman-6-ylethynyl]nicotinic acid ethyl ester, or a pharmaceutically acceptable salt thereof.

Suitably, the compound of Formula (I) is ethyl 6-[2-palmitoyl-4,4-dimethyl-3,4-dihydro-2-thiochromen-6-yl)ethynyl]pyridine-3-carboxylate, or a pharmaceutically acceptable salt thereof.

Suitably, the compound of Formula (I) is 6-[2-(2-Hydroxy-acetoxy)-4,4-dimethyl-thiochroman-6-ylethynyl]-nicotinic acid ethyl ester, or a pharmaceutically acceptable salt thereof.

Suitably, the compound of Formula (I) is ethyl 6-[(2-(2-methoxyacetyl)-4,4-dimethyl-3,4-dihydro-2-thiochromen-6-yl)ethynyl]pyridine-3-carboxylate, or a pharmaceutically acceptable salt thereof.

Suitably, the compound of Formula (I) is ethyl 6-[(2-acetyl-4,4-dimethyl-3,4-dihydro-2-thiochromen-6-yl)ethynyl]pyridine-3-carboxylate, or a pharmaceutically acceptable salt thereof.

Suitably, the compound of Formula (I) is ethyl 6-[(2-n-butyryloxyl-4,4-dimethyl-3,4-dihydro-2-thiochromen-6-yl) ethynyl]pyridine-3-carboxylate, or a pharmaceutically acceptable salt thereof.

Suitably, the compound of Formula (I) is ethyl 6-[(2-lauroyl-4,4-dimethyl-3,4-dihydro-2-thiochromen-6-yl)ethynyl]pyridine-3-carboxylate, or a pharmaceutically acceptable salt thereof. Suitably, the compound of Formula (I) is ethyl 6-[(2-isobutyryloxy-4,4-dimethyl-3,4-dihydro-2-thiochromen-6-yl)ethynyl]pyridine-3-carboxylate, or a pharmaceutically acceptable salt thereof.

Suitably, the compound of Formula (I) is ethyl 6-[(2-linoeoyll-4,4-dimethyl-3,4-dihydro-2-thiochromen-6-yl) ethynyl]pyridine-3-carboxylate, or a pharmaceutically acceptable salt thereof.

Suitably, the compound of Formula (I) is ethyl 6-[(2-linleolyl-4,4-dimethyl-3,4-dihydro-2-thiochromen-6-yl)ethynyl]pyridine-3-carboxylate, or a pharmaceutically acceptable salt thereof.

Suitably, the compound of Formula (I) is ethyl 6-[(2-(N-methyl-4-piperidinylcarboxy-4,4-dimethyl-3,4-dihydro-2-thiochromen-6-yl)ethynyl]pyridine-3-carboxylate, or a pharmaceutically acceptable salt thereof.

Suitably, the compound of Formula (I) is ethyl 6-[(2-propionyl-4,4-dimethyl-3,4-dihydro-2-thiochromen-6-yl)ethynyl]pyridine-3-carboxylate, or a pharmaceutically acceptable salt thereof.

Suitably, the compound of Formula (I) is ethyl 6-[(2-salicylicyl-4,4-dimethyl-3,4-dihydro-2-thiochromen-6-yl)ethynyl]pyridine-3-carboxylate, or a pharmaceutically acceptable salt thereof.

Suitably, the compound of Formula (I) is ethyl 6-[(2-(4-pyranyloxy-4,4-dimethyl-3,4-dihydro-2-thiochromen-6-yl) ethynyl]pyridine-3-carboxylate, or a pharmaceutically acceptable salt thereof.

Suitably, the compound of Formula (I) is ethyl 6-[(2-monomethyladopyl-4,4-dimethyl-3,4-dihydro-2-thiochromen-6-yl)ethynyl]pyridine-3-carboxylate, or a pharmaceutically acceptable salt thereof.

Suitably, the compound of Formula (I) is ethyl 6-[(2-(3-monomethylazelauate-4,4-dimethyl-3,4-dihydro-2-thiochromen-6-yl)ethynyl]pyridine-3-carboxylate, or a pharmaceutically acceptable salt thereof.

Suitably, the compound of Formula (I) is 6-[2-((S)-2-Amino-3-methyl-butyryloxy)-4,4-dimethyl-thiochroman-6-ylethynyl]-nicotinic acid ethyl ester, or a pharmaceutically acceptable salt thereof.

According to another embodiment, the compound of Formula (I) is selected from the group consisting of:

Ethyl 6-[(2-propionyl-4,4-dimethyl-3,4-dihydro-2-thiochromen-6-yl)ethynyl]pyridine-3-carboxylate;
Ethyl 6-[(2-(N-methyl-4-piperidinylcarboxy-4,4-dimethyl-3,4-dihydro-2-thiochromen-6-yl)ethynyl]pyridine-3-carboxylate;
6-((4,4-dimethyl-2-oxothiochroman-6-yl)ethynyl)nicotinic acid;

6-[2-((S)-2-Amino-3-methyl-butyryloxy)-4,4-dimethyl-thiochroman-6-ylethynyl]-nicotinic acid ethyl ester;

6-[2-(2-Hydroxy-acetoxy)-4,4-dimethyl-thiochroman-6-yl-ethynyl]-nicotinic acid ethyl ester; and Ethyl 6-[(2-monomethyladopyl-4,4-dimethyl-3,4-dihydro-2-thiochromen-6-yl) ethynyl]pyridine-3-carboxylate; or a pharmaceutically acceptable salt thereof.

In another aspect, the invention provides a compound of the formula:

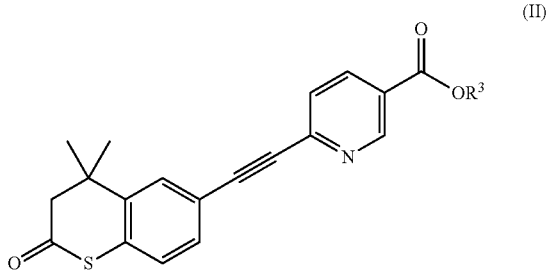

(II)

wherein $R^3$ is hydrogen, optionally substituted $C_{1-18}$ alkyl, optionally substituted $C_{2-18}$ alkenyl, optionally substituted $C_{2-18}$ alkynyl, optionally substituted aryl group, optionally substituted heterocyclic group, optionally substituted $C_{3-7}$ cycloalkyl group, or an optionally substituted heteroaryl group; or a pharmaceutically acceptable salt thereof.

When $R^3$ is an optionally substituted $C_{1-18}$ alkyl, $C_{2-18}$ alkenyl, $C_{2-18}$ alkynyl, aryl, heterocyclic, cycloalkyl or heteroaryl group, the group is optionally substituted one or more times, preferably 1 to 4 times independently by halogen; hydroxy; $NR_4R_5$; hydroxy substituted $C_{1-6}$ alkyl; $C_{1-6}$ alkoxy, such as methoxy or ethoxy; halosubstituted $C_{1-6}$ alkoxy; halo-substituted $C_{1-6}$ alkyl, such as $CF_2CF_2H$ or $CF_3$; $C_{1-6}$ alkyl such as methyl, ethyl, isopropyl, etc.; —C(O)$OR_6$ or —OC(O)$R_6$.

Suitably, $R_4$ and $R_5$ are independently selected from hydrogen or $C_{1-6}$ alkyl. In one embodiment both $R_4$ and $R_5$ are hydrogen.

Suitably, $R_6$ is independently selected from hydrogen or $C_{1-6}$ alkyl. In one embodiment $R_6$ is $C_{1-6}$ alkyl. In another embodiment the $C_{1-6}$ alkyl is methyl.

When $R^3$ is an optionally substituted aryl group, it is as defined above for $R^1$ or $R^2$ in Formula (I) herein.

When $R^3$ is an optionally substituted heteroaryl group, it is as defined above for $R^1$ or $R^2$ in Formula (I) herein.

When $R^3$ is an optionally substituted heterocyclic group, it is as defined above for $R^1$ or $R^2$ in Formula (I) herein.

In one embodiment, $R^3$ is hydrogen or an optionally substituted $C_{1-6}$ alkyl.

In one embodiment, $R^3$ is hydrogen. This compound is 6-((4,4-dimethyl-2-oxothiochroman-6-yl)ethynyl)nicotinic acid, and is also described herein as keto tazarotenic acid.

According to another embodiment, $R^3$ is $C_{1-6}$ alkyl. In another embodiment, the $C_{1-6}$ alkyl is ethyl. This compound is ethyl 6-((4,4-dimethyl-2-oxothiochroman-6-yl)ethynyl)nicotinate, and is also described herein as keto tazarotene.

Tazarotene Benzoate

According to a particular embodiment, the compound is 6-(2-(2-benzoyloxy-4,4-dimethylthiochroman-6-yl)ethynyl) nicotinic acid, ethyl ester (i.e. tazarotene benzoate). Tazarotene benzoate is formed by combining tazarotene and benzoyl peroxide. This novel compound penetrates the skin and has retinoid-like activity. The S and R enantiomers have been isolated and characterized, and described herein. A range of analogues and metabolites of tazarotene benzoate have also been isolated, synthesized and characterized as is further described.

Active Metabolites of Tazarotene

Figure 22:
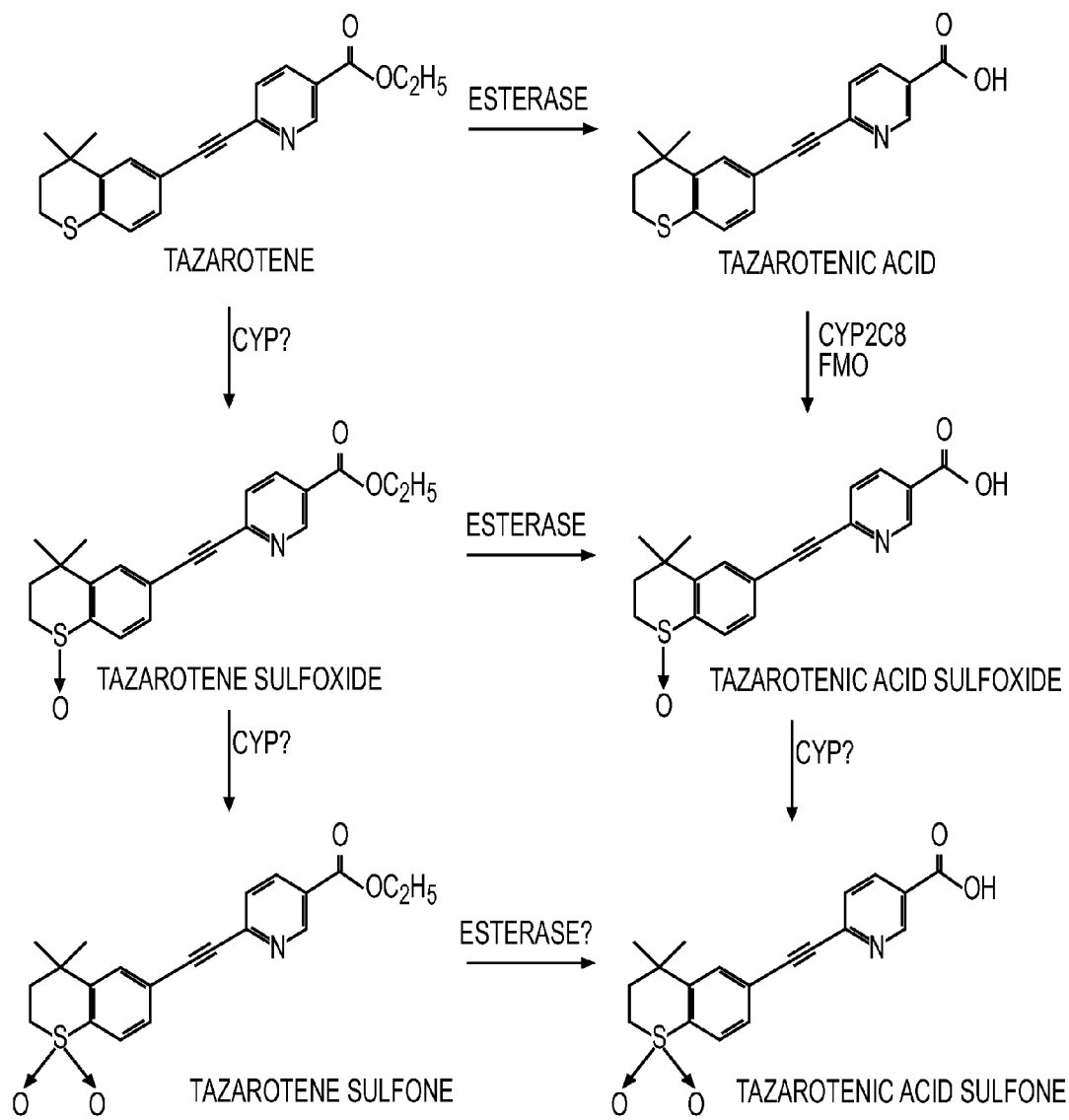
FIG. 22 illustrates the proposed metabolism of tazarotene.

Known metabolites of tazarotene i.e. tazarotene sulfoxide and tazarotenic acid, have been shown to penetrate the skin. However, other known metabolites of tazarotene, namely ethyl 6-((4,4-dimethyl-1,1-dioxidothiochroman-6-yl)ethynyl)nicotinate (tazarotene sulfone), 6-((4,4-dimethyl-1-oxidothiochroman-6-yl)ethynyl)nicotinic acid (tazarotenic acid sulfoxide), and 6-((4,4-dimethyl-1,1-dioxidothiochroman-6-yl)ethynyl)nicotinic acid (tazarotenic acid sulfone), which were previously thought by others to have little or no retinoid activity, have been discovered to exert retinoid like activity (FIG. 22 and Example 3).

Accordingly, the present invention also relates to a method of treating a skin disorder in a subject, the method comprising administering a composition comprising a therapeutically effective amount of a compound selected from the group consisting of ethyl 6-((4,4-dimethyl-1,1-dioxidothiochroman-6-yl)ethynyl)nicotinate, 6-((4,4-dimethyl-1-oxidothiochroman-6-yl)ethynyl)nicotinic acid and 6-((4,4-dimethyl-1,1-dioxidothiochroman-6-yl)ethynyl)nicotinic acid, or a pharmaceutically acceptable salt thereof, along with one or more pharmaceutically acceptable excipients, to a subject in need thereof.

In an embodiment, the present invention relates to the use of a compound selected from the group consisting of ethyl 6-((4,4-dimethyl-1,1-dioxidothiochroman-6-yl)ethynyl) nicotinate, 6-((4,4-dimethyl-1-oxidothiochroman-6-yl)ethynyl)nicotinic acid and 6-((4,4-dimethyl-1,1-dioxidothiochroman-6-yl)ethynyl)nicotinic acid, or a pharmaceutically acceptable salt thereof, in the preparation of a medicament for the treatment of a skin disorder.

In another embodiment, the invention relates to the use of a compound selected from the group consisting of ethyl 6-((4,4-dimethyl-1,1-dioxidothiochroman-6-yl)ethynyl)nicotinate, 6-((4,4-dimethyl-1-oxidothiochroman-6-yl)ethynyl) nicotinic acid and 6-((4,4-dimethyl-1,1-dioxidothiochroman-6-yl)ethynyl)nicotinic acid, or a pharmaceutically acceptable salt thereof, for the treatment of a skin disorder.

In yet another embodiment, the invention relates to a pharmaceutical composition comprising a compound selected from the group consisting of ethyl 6-((4,4-dimethyl-1,1-dioxidothiochroman-6-yl)ethynyl)nicotinate, 6-((4,4-dimethyl-1-oxidothiochroman-6-yl)ethynyl)nicotinic acid and 6-((4,4-dimethyl-1,1-dioxidothiochroman-6-yl)ethynyl) nicotinic acid, or a pharmaceutically acceptable salt thereof, along with one or more pharmaceutically acceptable excipients.

Pharmaceutical Compositions

According to an embodiment, the present invention provides a pharmaceutical composition comprising a compound of Formula (I) or (II), or a pharmaceutically acceptable salt thereof, and one or more pharmaceutically acceptable carriers or excipients.

In one embodiment, the pharmaceutical composition comprises a second pharmaceutically active agent.

In one embodiment, the second pharmaceutically active agent is selected from the group consisting benzoyl peroxide, an antibiotic, a corticosteroid and a vitamin D analogue.

In an embodiment, the second pharmaceutically active agent is benzoyl peroxide.

In another embodiment, the second pharmaceutically active agent is an antibiotic, such as clindamycin or a pharmaceutically acceptable salt thereof (e.g. clindamycin phosphate).

In another embodiment, the second pharmaceutically active agent is a corticosteroid. Suitable corticosteroids include, but are not limited to, alclometasone dipropionate, amcinonide, beclomethasone dipropionate, betamethasone benzoate, betamethasone dipropionate, betamethasone valerate, budesonide, clobetasol propionate, clobetasone butyrate, cortisone acetate, desonide, desoximetasone, diflorasone diacetate, diflucortolone valerate, fluclorolone acetonide, flumethasone pivalate, fluocinolone acetonide, fluocinonide, fluocortin butyl, fluocortolone, fluprednidene acetate, flurandrenolide, flurandrenolone, fluticasone propionate, halcinonide, halobetasol propionate, hydrocortisone, hydrocortisone acetate, hydrocortisone butyrate, hydrocortisone propionate, hydrocortisone valerate, methylprednisolone acetate, mometasone furoate, pramoxine hydrochloride, prednisone acetate, prednisone valerate, triamcinolone acetonide, prednicarbate, and pharmaceutically acceptable salts thereof.

In another embodiment, the second pharmaceutically active agent is a vitamin D analogue. Suitable vitamin D analogues include, but are not limited to, calcidiol, calcitriol, calcipotriene, paricalcitol, 22-oxacolcitriol, dihydrotachysterol, calciferol, and pharmaceutically acceptable salts thereof.

In an embodiment, the invention provides a pharmaceutical composition comprising a compound of Formula (I) or (II) or a pharmaceutically acceptable salt thereof and a second active agent, wherein the stability of the compound of Formula (I) or (II) is superior to the stability of tazarotene in a pharmaceutical composition comprising tazarotene and the second active agent. In an embodiment, the compound of Formula (I) or (II) is tazarotene benzoate or tazarotene nicotinate. According to a particular embodiment, the second active agent is benzoyl peroxide. Suitably, the amounts present in the composition are therapeutically effective amounts for the treatment of skin disorders.

The compounds of the present invention may be formulated as pharmaceutical compositions and administered orally, topically, dermally, parenterally, by injection, by pulmonary or nasal delivery, sublingually, rectally or vaginally. According to a particular embodiment, the pharmaceutical composition is adapted for oral or topical administration. The term "administered by injection" includes intravenous, intraarticular, intramuscular (e.g. by depot injection where the active compounds are released slowly into the blood from the depot and carried from there to the target organs), intraperitoneal, intradermal, subcutaneous, and intrathecal injections, as well as use of infusion techniques. Dermal administration may include topical or transdermal administration. Transdermal administration can be accomplished by suitable patches, solutions, emulsions, suspensions, ointments, pastes, powders, foams, creams, lotions or gels as generally known in the art, specifically designed for the transdermal delivery of active agents, optionally in the presence of specific permeability enhancers. Similarly, topical administration can be accomplished by a solution, emulsion, suspension, ointment, paste, powder, foam, cream, lotion or gel. In a particular embodiment, topical administration is accomplished with an aerosol foam.

Exemplary pharmaceutically acceptable excipients include abrasives, acidifying agents, adhesives, adsorbents, alkalizing agents, antibacterial agents, anticaking agents, antioxidants, binding agents, buffering agents, bulking agents, chelating agents, coating agents, coloring agents, complexing agents, controlled release agents, cooling agents, detergents, diluents, dispersing agents, dissolution enhancers, emollients, emulsifying agents, emulsion stabilizers, film forming agents, gelling agents, glidants, humectants, lubricants, opacifying agents, penetration enhancers, pH adjusting agents, pigments, plasticizers, preservatives, propellants, sequestering agents, solubilizing agents, solvents, surfactants, suspending agents, thickening agents, viscosity increasing agents and wetting agents.

The pharmaceutical composition may be formulated using methods known in the art as immediate release, sustained release, delayed release, pulsatile release or two step release, for example.

The dosage of the active agent in the pharmaceutical composition will depend upon a variety of factors, including but not limited to, the activity of the active agent, the condition being treated, the nature of the pharmaceutical composition, the mode of administration and the age, body weight, general health and gender of the patient.

Methods of Use

According to an embodiment, the present invention relates to a method of treating a skin disorder. The method comprises administering to a subject a pharmaceutical composition comprising a therapeutically effective amount of a compound of Formula (I) or (II), or a pharmaceutically acceptable salt thereof, along with one or more pharmaceutically acceptable excipients, to a subject in need thereof.

Another to an embodiment, the skin disorder is acne, psoriasis, seborrhea, ichthyosis or keratosis pilaris. According to a particular embodiment, the skin disorder is acne or psoriasis.

Definitions

The term "halo" or "halogens" is used herein to mean the halogens, chloro, fluoro, bromo and iodo.

The term "alkyl" is used herein to mean an aliphatic hydrocarbon group which may be straight or branched chain having about 1 to about 18 carbon atoms in the chain. A preferred embodiment is an alkyl group having from 1 to about 6 carbon atoms. Alkyl as defined herein may be optionally substituted with a designated number of substituents.

The term "unsaturated" refers to the presence of one or more double or triple bonds between carbon atoms of a hydrocarbon chain.

The term "alkenyl" is used herein to mean a hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl or 2-butenyl. Alkenyl as defined herein may be optionally substituted with a designated number of substituents.

The term "alkynyl" is used herein to mean a hydrocarbon chain of a specified number of carbon atoms of either a straight or branched configuration and having at least one carbon-carbon triple bond, which may occur at any point along the chain. An example of an alkynyl is acetylene. Alkynyl as defined herein may be optionally substituted with a designated number of substituents.

The term "cycloalkyl" is used herein to refer to cyclic radicals, such as a non-aromatic hydrocarbon ring containing a specified number of carbon atoms. For example, $C_{3-7}$ cycloalkyl means a non-aromatic ring containing at least three, and at most seven, ring carbon atoms. Representative examples of "cycloalkyl" as used herein include, but are not limited to, cyclopropyl, cyclobutyl, cyclopentyl, cyclohexyl and cycloheptyl.

The term "aryl" is used herein to mean an aromatic cyclic hydrocarbon group of from 5 to 20 carbon atoms having a single ring (e.g., phenyl) or multiple condensed (fused) rings (e.g. naphthyl or anthryl). Preferred aryl groups include phenyl and naphthyl.

The terms "heteroaryl ring", "heteroaryl moiety", and "heteroaryl" are used herein to mean a monocyclic five- to seven-membered unsaturated aromatic hydrocarbon ring containing at least one heteroatom selected from oxygen, nitrogen and sulfur. Examples of heteroaryl rings include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil. The terms "heteroaryl ring", "heteroaryl moiety", and "heteroaryl" shall also be used herein to refer to fused aromatic rings comprising at least one heteroatom selected from oxygen, nitrogen and sulfur. Each of the fused rings may contain five or six ring atoms. Examples of fused aromatic rings include, but are not limited to, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl and phthalazinyl.

The terms "heterocyclic rings", "heterocyclic moieties" and "heterocyclyl" are used herein to mean a monocyclic three- to seven-membered saturated or non-aromatic, unsaturated hydrocarbon ring containing at least one heteroatom selected from nitrogen, oxygen, sulphur or oxidized sulphur moieties, such as S(O)m, and m is 0 or an integer having a value of 1 or 2. The terms "heterocyclic rings", "heterocyclic moieties", and "heterocyclyl" shall also refer to fused rings, saturated or partially unsaturated, and wherein one of the rings may be aromatic, or heteroaromatic. Each of the fused rings may have from four to seven ring atoms. Examples of heterocyclyl groups include, but are not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), azepine, diazepine, aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety).

The terms "arylalkyl" or "heteroarylalkyl" or "heterocyclicalkyl" are used herein to mean a $C_{1-4}$ alkyl (as defined above) attached to an aryl, heteroaryl or heterocyclic moiety (as also defined above) unless otherwise indicated.

"Heteroatom" refers to a nitrogen, sulfur or oxygen atom, wherein the nitrogen and sulfur atoms may be optionally oxidized.

The phrases an "effective amount" or "an amount effective to" or a "therapeutically effective amount" of a pharmaceutically active agent or ingredient, are used herein to refer to an amount of the pharmaceutically active agent sufficient to have a therapeutic effect upon administration. Effective amounts of the pharmaceutically active agent will vary with the particular condition or conditions being treated, the severity of the condition, the duration of the treatment, and the specific components of the composition being used.

The terms "administering" and "administration" are used herein to mean any method which in sound medical practice delivers the pharmaceutical composition to a subject in such a manner as to provide a therapeutic effect.

The term "prodrug" is used herein to mean a compound which releases an active agent in vivo when the prodrug is administered to a subject. Prodrugs of an active agent are prepared by modifying one or more functional groups present in the active agent in such a way that the modification may be cleaved in vivo to release the active compound.

The terms "treatment" or "treating" of a skin disorder encompasses alleviation of at least one symptom thereof, a reduction in the severity thereof, or the delay, prevention or inhibition of the progression thereof. Treatment need not mean that the disorder is totally cured. A useful composition herein need only to reduce the severity of the disorder, reduce the severity of symptoms associated therewith, provide improvement to a patient's quality of life, or delay, prevent or inhibit the onset of the disorder.

The term "pharmaceutically acceptable salt" refers to salts that are pharmaceutically acceptable and that possess the desired pharmacological activity of the parent compound. Such salts include: (1) acid addition salts, formed with acids such as, for example, acetic acid, benzoic acid, citric acid, gluconic acid, glutamic acid, glutaric acid, glycolic acid, hydrochloric acid, lactic acid, maleic acid, malic acid, malonic acid, mandelic acid, phosphoric acid, propionic acid, sorbic acid, succinic acid, sulfuric acid, tartaric acid, naturally and synthetically derived amino acids, and mixtures thereof; or (2) salts formed when an acidic proton present in the parent compound is either (i) replaced by a metal ion e.g. an alkali metal ion, an alkaline earth metal ion or an aluminum ion; or (ii) protonates an organic base such as, for example, ethanolamine, diethanolamine, triethanolamine, tromethamine and N-methylglucamine Any concentration range, percentage range or ratio range recited herein is to be understood to include concentrations, percentages or ratios of any integer within that range and fractions thereof, such as one tenth and one hundredth of an integer, unless otherwise indicated.

It should be understood that the terms "a" and "an" as used herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

Throughout the application, descriptions of various embodiments use "comprising" language, however in some specific instances, an embodiment can alternatively be described using the language "consisting essentially of" or "consisting of".

All numbers expressing quantities, percentages or proportions, and other numerical values used in the specification and claims, are to be understood as being modified in all instances by the term "about."

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

With regard to stereoisomers, the compounds of the Formulas (I) and (II) herein may have one or more asymmetric carbon atom and may occur as racemates, racemic mixtures and as individual enantiomers or diastereomers. All such isomeric forms are included within the present invention, including mixtures thereof.

Cis (E) and trans (Z) isomerism may also occur. The present invention includes the individual stereoisomers of the compounds of the invention and where appropriate, the individual tautomeric forms thereof, together with mixtures thereof.

Separation of diastereoisomers or cis and trans isomers may be achieved by conventional techniques, e.g. by fractional crystallization, chromatography or HPLC. A stereoisomeric mixture of the agent may also be prepared from a corresponding optically pure intermediate or by resolution, such as HPLC of the corresponding racemate using a suitable chiral support or by fractional crystallization of the diastereoisomeric salts formed by reaction of the corresponding racemate with a suitable optically active acid or base, as appropriate.

Other terms used herein are intended to be defined by their well known meanings in the art.

EXAMPLES

Example 1

Degradation of Tazarotene in the Presence of Benzoyl Peroxide

DUAC® gel (1% clindamycin and 5% benzoyl peroxide marketed by Stiefel Laboratories, Inc.) and TAZORAC® cream (0.1% tazarotene marketed by Allergan, Inc.) have been successfully used to treat facial acne. However, these topical treatments are not approved for concomitant use. To study whether tazarotene is susceptible to oxidative decomposition by benzoyl peroxide, an in vitro laboratory study was conducted wherein a mixture of DUAC gel and TAZORAC cream was prepared.

Samples were prepared by taking equal portions of DUAC gel and TAZORAC cream and mixing them thoroughly at room temperature with a spatula in a suitable container to form a uniform mixture. The initial samples were analyzed immediately by HPLC. The other samples were placed into an oven at 35° C. and removed for analysis after one, two, four, six and eight hours. An allowance was made for product evaporation over the course of the study.

FIG. 1 and Table 1 illustrate that approximately 22% of tazarotene was lost after four hours. The major degradant product was tazarotene sulfoxide (~16% after 4 hours). A previously unknown derivative was also identified, namely tazarotene benzoate, which eluted chromatographically after tazarotene and accounted for ~6.3% by weight after four hours.

Similar results were obtained when "aged" samples of DUAC gel and TAZORAC cream were used (Table 2). It is believed that the tazarotene sulfoxide and tazarotene benzoate are oxidative reaction products arising from reaction of the benzoyl peroxide in DUAC gel with the tazarotene in TAZORAC cream.

TABLE 1

HPLC analysis of mixtures of DUAC gel and TAZORAC cream (using "fresh" samples)

| | | | | % Label | | | |
|---|---|---|---|---|---|---|---|
| Substance | Time Point (hours) | Preparation | Tazarotene | Tazarotene Sulfoxide | Tazarotene Benzoate | RRT = 1.05 | RRT = 1.15 |
| TAZORAC | 0 | A | 99.0 | 0.1 | | | 0.9 |
| | | B | 99.0 | 0.1 | | | 0.9 |
| | | C | 98.3 | 0.1 | | | 1.6 |
| | 8 | A | 99.7 | 0.1 | | | 0.3 |
| | | B | 99.5 | 0.1 | | | 0.4 |
| | | C | 99.0 | 0.1 | | | 0.9 |
| Mixture (DUAC/ TAZORAC) | 0 | A | 98.6 | 1.1 | 0.3 | | |
| | | B | 98.6 | 1.1 | 0.3 | | |
| | | C | 98.4 | 1.3 | 0.3 | | |
| | 1 | A | 93.8 | 4.5 | 1.7 | | |
| | | B | 94.5 | 4.0 | 1.5 | | |
| | | C | 94.1 | 4.3 | 1.6 | | |
| | 2 | A | 86.0 | 10.0 | 3.7 | 0.3 | |
| | | B | 86.9 | 9.1 | 3.6 | 0.3 | |
| | | C | 87.5 | 8.8 | 3.4 | 0.3 | |
| | 4 | A | 77.3 | 16.0 | 6.3 | 0.4 | |
| | | B | 77.3 | 16.0 | 6.3 | 0.4 | |
| | | C | 76.9 | 16.2 | 6.5 | 0.4 | |
| | 6 | A | 67.1 | 23.3 | 9.1 | 0.6 | |
| | | B | 69.6 | 21.6 | 8.3 | 0.5 | |
| | | C | 70.6 | 20.9 | 8.0 | 0.5 | |
| | 8 | A | 61.1 | 27.8 | 10.5 | 0.6 | |
| | | B | 60.2 | 28.6 | 10.6 | 0.6 | |
| | | C | 59.4 | 29.4 | 10.6 | 0.6 | |

TABLE 2

HPLC analysis of mixtures of DUAC gel and TAZORAC cream (using "aged" samples)

| | | | | % Label | | | |
|---|---|---|---|---|---|---|---|
| Substance | Time Point | Preparation | Tazarotene | Tazarotene Sulfoxide | Tazarotene Benzoate | RRT = 1.05 | RRT = 1.15 |
| TAZORAC | 0 | A | 99.4 | 0.1 | | | 0.5 |
| | | B | 99.1 | 0.1 | | | 0.8 |
| | | C | 99.1 | 0.1 | | | 0.8 |

TABLE 2-continued

HPLC analysis of mixtures of DUAC gel and TAZORAC cream (using "aged" samples)

| | | | | % Label | | | |
|---|---|---|---|---|---|---|---|
| Substance | Time Point | Preparation | Tazarotene | Tazarotene Sulfoxide | Tazarotene Benzoate | RRT = 1.05 | RRT = 1.15 |
| | 8 | A | 99.4 | 0.1 | | | 0.5 |
| | | B | 99.5 | 0.1 | | | 0.4 |
| | | C | 99.5 | 0.1 | | | 0.4 |
| Mixture (DUAC/ TAZORAC) | 0 | A | 99.2 | 0.8 | | | |
| | | B | 99.3 | 0.7 | | | |
| | | C | 99.2 | 0.8 | | | |
| | 1 | A | 95.2 | 3.5 | 1.3 | | |
| | | B | 95.2 | 3.4 | 1.4 | | |
| | | C | 95.3 | 3.5 | 1.3 | | |
| | 2 | A | 89.1 | 7.8 | 3.1 | | |
| | | B | 89.0 | 7.7 | 3.0 | 0.3 | |
| | | C | 89.1 | 7.6 | 3.0 | 0.3 | |
| | 4 | A | 76.9 | 16.3 | 6.5 | 0.4 | |
| | | B | 77.0 | 16.2 | 6.5 | 0.4 | |
| | | C | 77.1 | 16.0 | 6.5 | 0.4 | |
| | 6 | A | 63.4 | 25.6 | 10.5 | 0.5 | |
| | | B | 63.7 | 25.5 | 10.3 | 0.5 | |
| | | C | 64.2 | 25.2 | 10.1 | 0.6 | |
| | 8 | A | 54.6 | 31.9 | 12.9 | 0.6 | |
| | | B | 54.2 | 32.2 | 12.9 | 0.7 | |
| | | C | 53.6 | 32.7 | 13.1 | 0.7 | |

Example 2

Further Study of Tazarotene and its Metabolites

An in vitro study was conducted to assess the formation of tazarotene degradants following the application of a mixture of DUAC gel and TAZORAC cream to human skin.

Equal portions of DUAC gel and TAZORAC cream were dispensed into a glass vial and mixed for approximately three minutes with a metal spatula to ensure a homogenous mixture. Samples of European DUAC gel and US DUAC gel were used in separate experiments. The products differ inasmuch as European DUAC gel does not contain paraben preservatives. The test mixtures were then applied to the surface of split-thickness skin (~0.25 mm) at a dose of 15.6 mg/cm$^2$ and spread evenly using a positive displacement pipette.

After 2 and 6 hours, the skin samples were washed, tape stripped twice, and then the epidermis was peeled from the dermis using a heat block. The skin samples were then extracted with acetonitrile overnight at 4° C. The distribution of tazarotene and its degradants within the epidermis, dermis and surface wash were quantified by LC/MS/MS with a 50 pg/mL LOQ. The experiments were performed under yellow light conditions. For the purposes of comparison, mixtures of DUAC gel and TAZORAC cream were also prepared and retained for stability testing at 0, 2 and 6 hour time points.

Figure 2A:
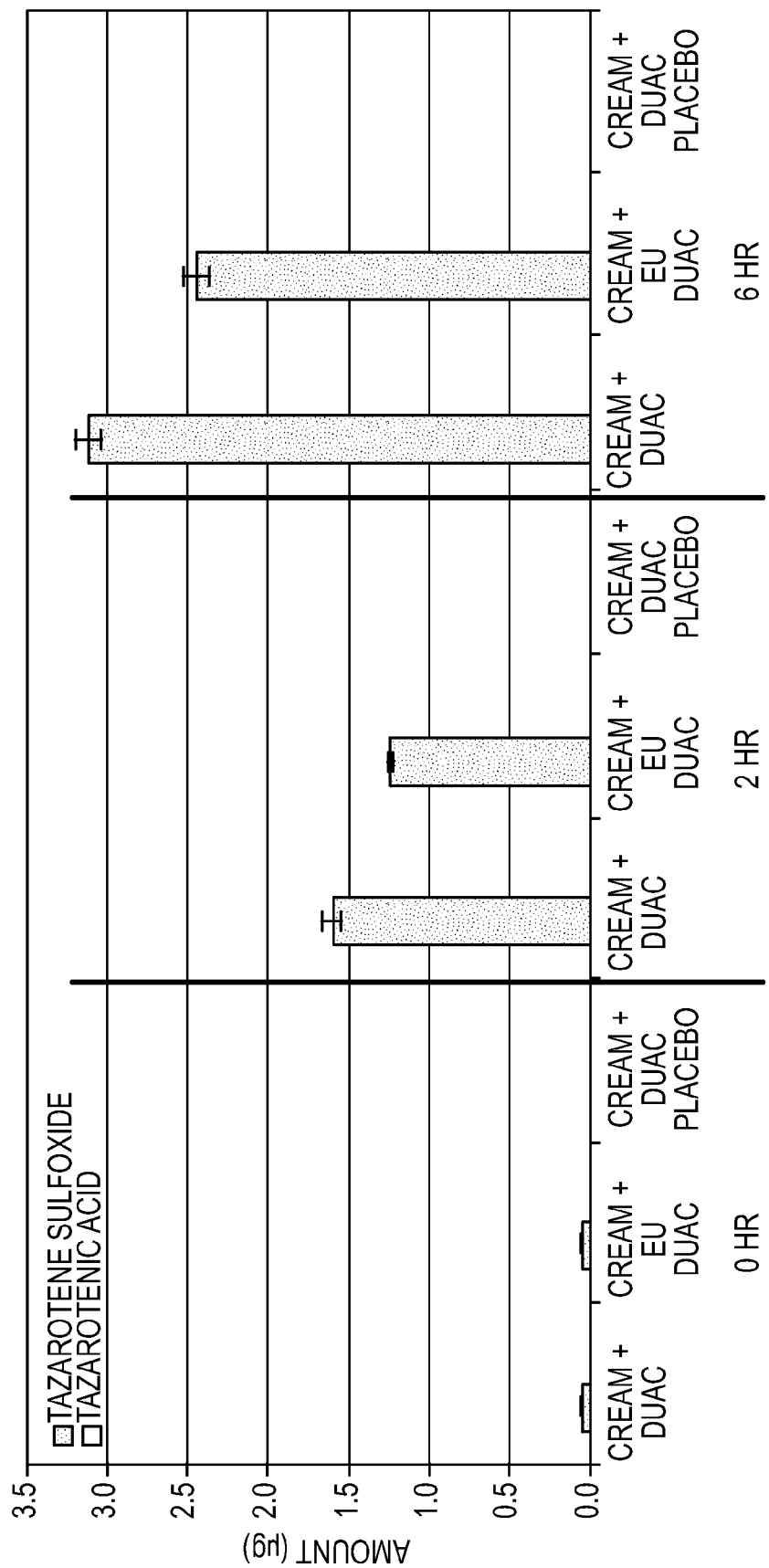
FIG. 2A illustrates the amount of tazarotene sulfoxide and tazarotenic acid in stability samples (at least 4 replicates and 4 donors (n≥17)±SEM).
Figure 2B:
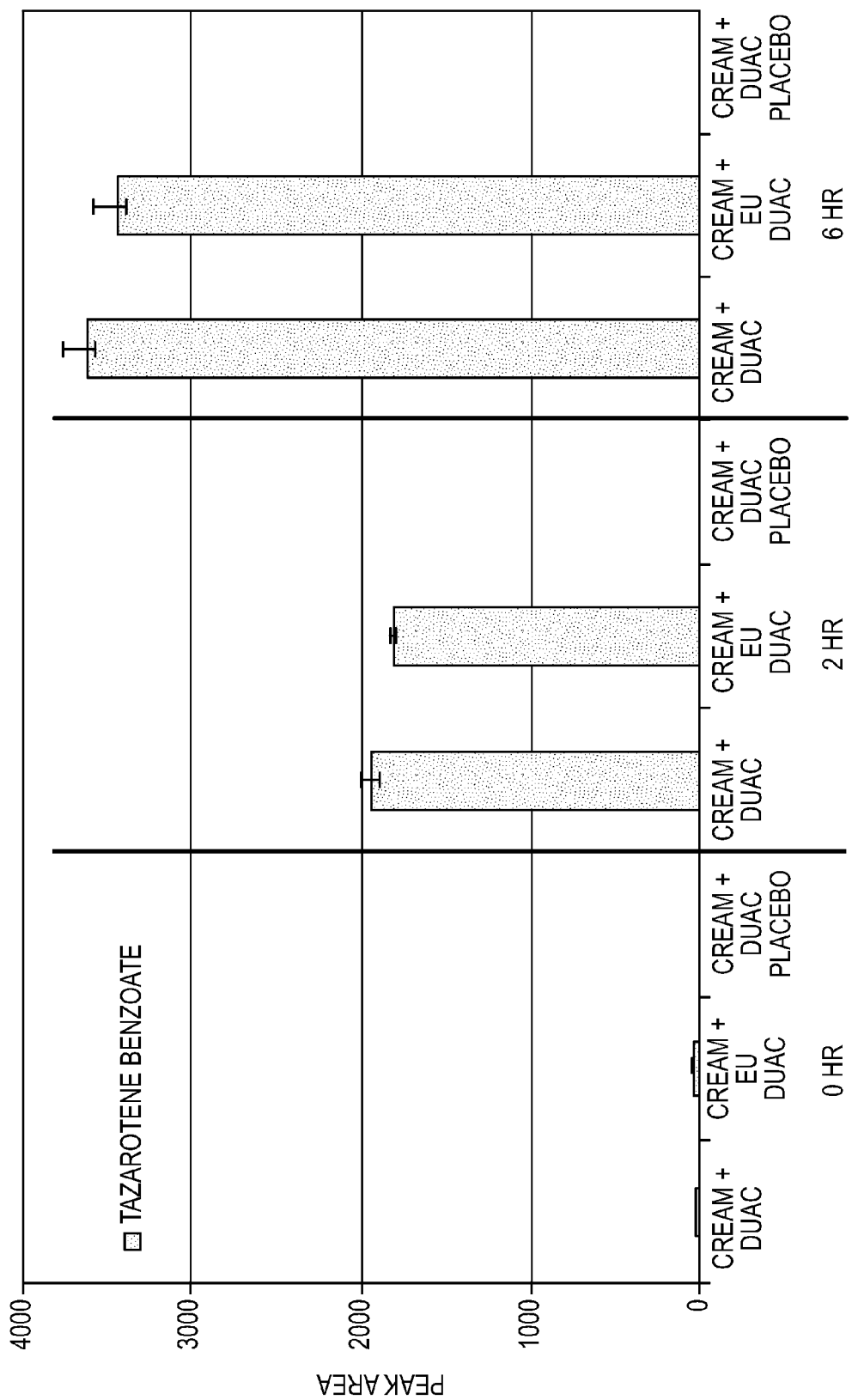
FIG. 2B illustrates the amount of tazarotene benzoate in stability samples (at least 4 replicates and 4 donors (n≥17) ±SEM).

As illustrated in FIG. 2A, the mixture of DUAC gel and TAZORAC cream in the stability samples resulted in the formation of tazarotene sulfoxide. The quantity of the tazarotene sulfoxide degradant doubled from the 2 hour time point to the 6 hour time point. As shown in FIG. 2B, tazarotene benzoate also formed. Again, there was a significant increase in the quantity of tazarotene benzoate present at the 6 hour time point relative to the 2 hour time point.

Figure 3A:
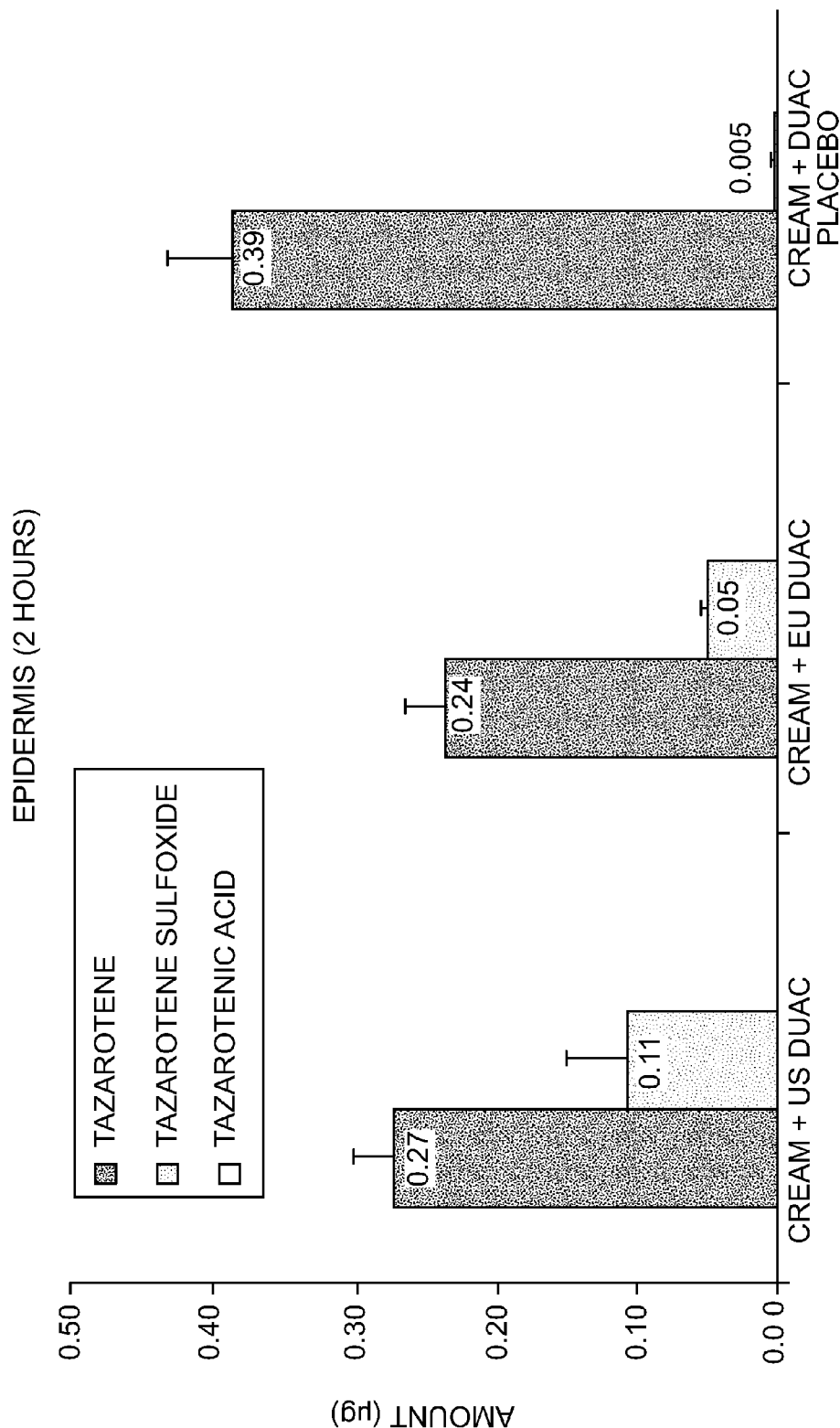
FIG. 3A illustrates the amount of tazarotene, tazarotene sulfoxide and tazarotenic acid in the epidermis 2 hours post-application (at least 4 replicates and 4 donors (n≥17)±SEM).
Figure 3B:
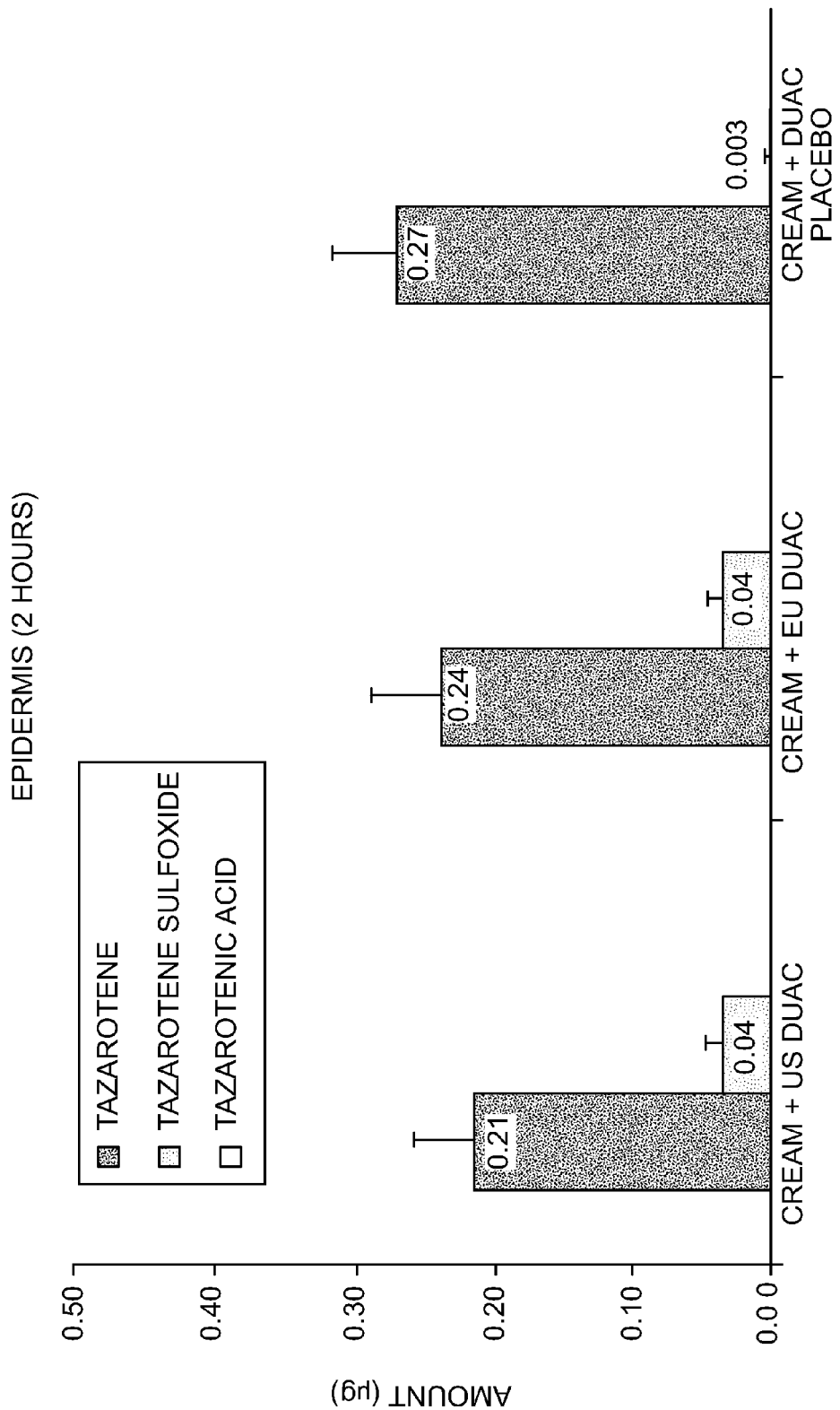
FIG. 3B illustrates the amount of tazarotene, tazarotene sulfoxide and tazarotenic acid in the dermis 2 hours post-application (at least 4 replicates and 4 donors (n≥17)±SEM).
Figure 4A:
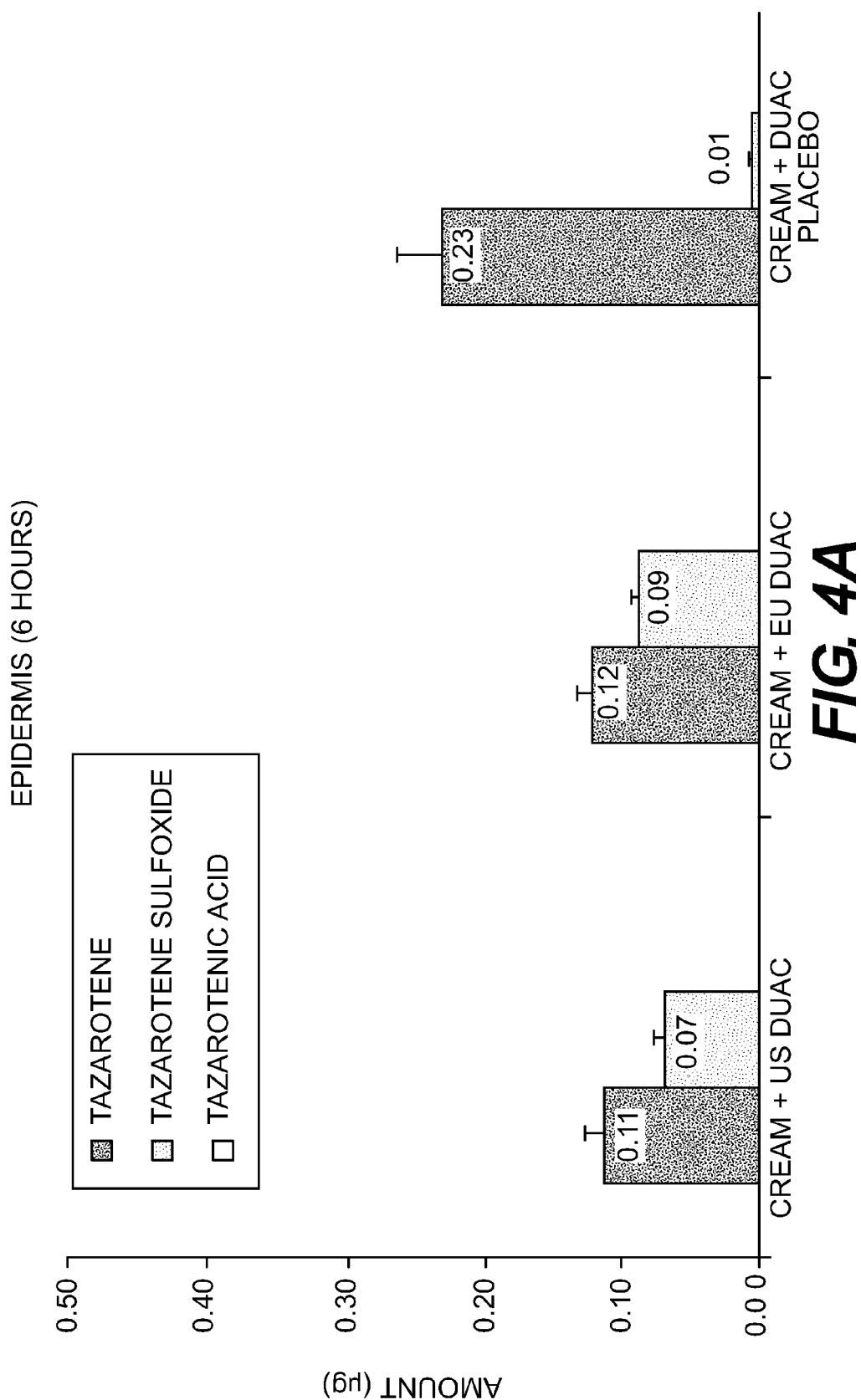
FIG. 4A illustrates the amount of tazarotene, tazarotene sulfoxide and tazarotenic acid in the epidermis 6 hours post-application (at least 4 replicates and 4 donors (n≥17)±SEM).
Figure 4B:
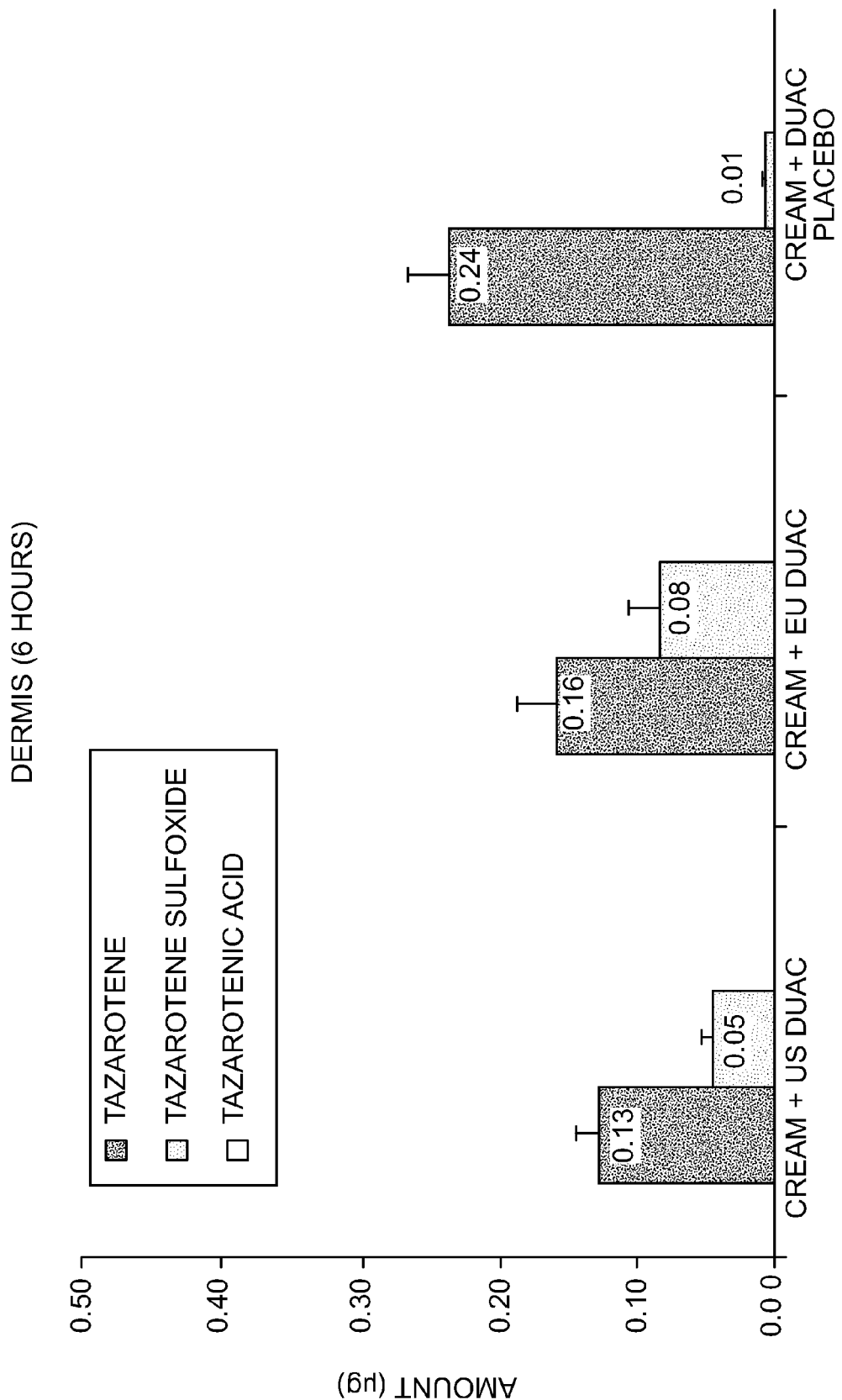
FIG. 4B illustrates the amount of tazarotene, tazarotene sulfoxide and tazarotenic acid in the dermis 6 hours post-application (at least 4 replicates and 4 donors (n≥17)±SEM).

The study also showed that after 2 hours of application of the DUAC/TAZORAC mixture to the skin, tazarotene sulfoxide was identified in the epidermis and dermis (FIGS. 3A and 3B). After 6 hours of application, there was a continued loss of tazarotene and resultant formation of tazarotene sulfoxide (FIGS. 4A and 4B).

Figure 5A:
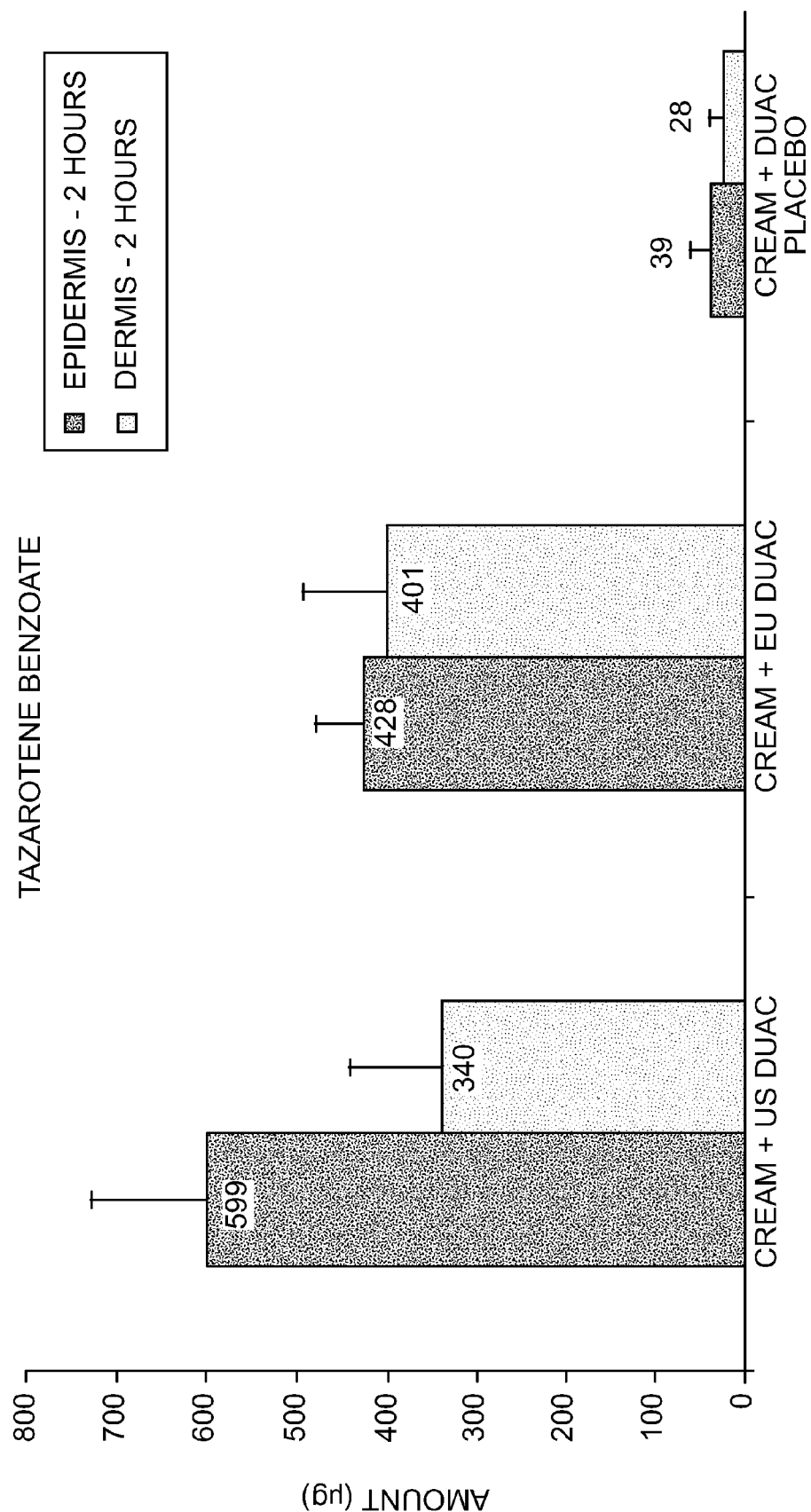
FIG. 5A illustrates the amount of tazarotene benzoate in the epidermis and dermis 2 hours post-application (at least 4 replicates and 4 donors (n≥17)±SEM).
Figure 5B:
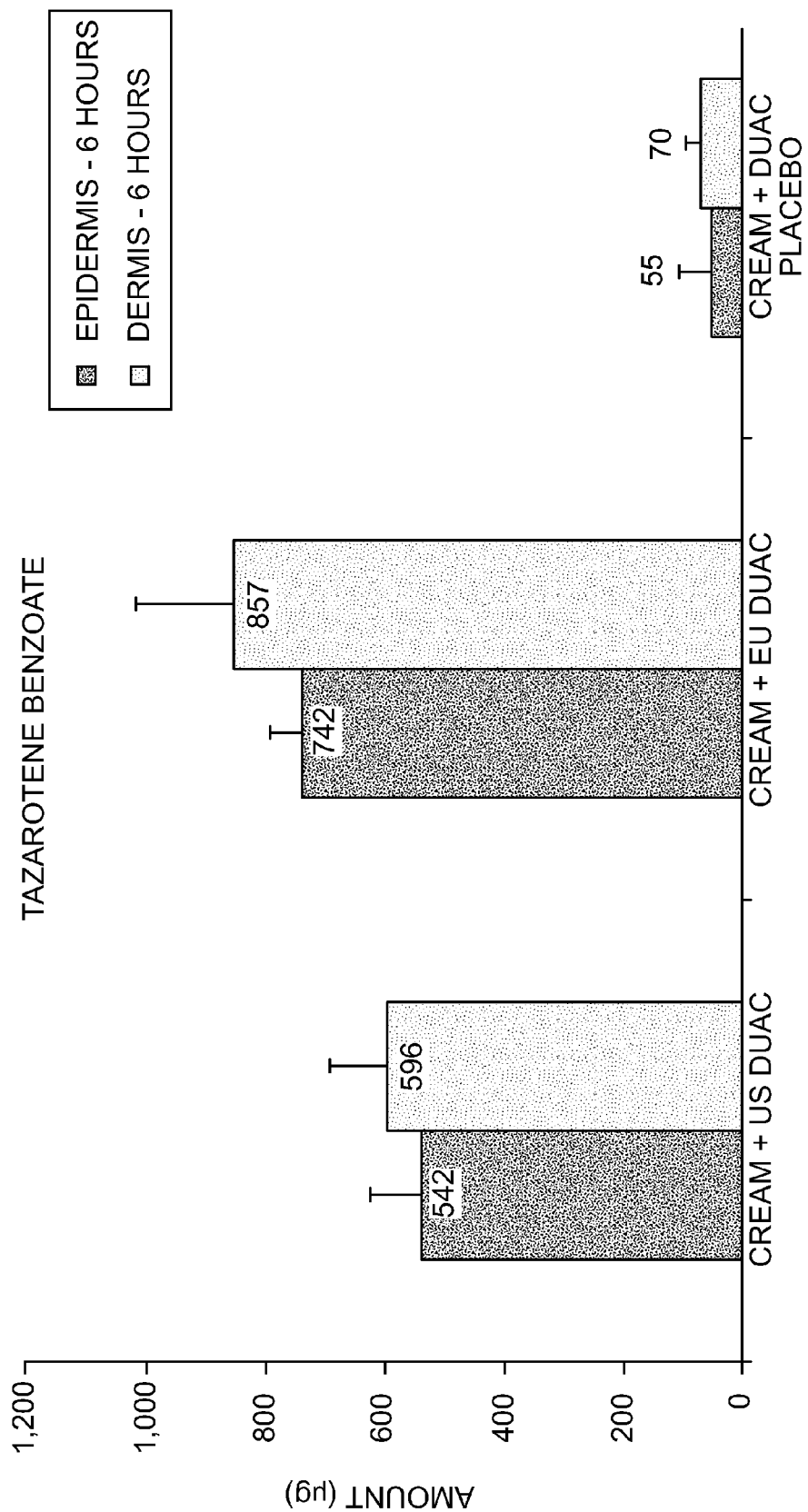
FIG. 5B illustrates the amount of tazarotene benzoate in the epidermis and dermis 6 hours post-application (at least 4 replicates and 4 donors (n≥17)±SEM).

Tazarotene benzoate was detectable in all samples including the placebo (FIGS. 5A and 5B). The presence of tazarotene benzoate in the placebo sample suggests that endogenous benzoic acid may be present.

While tazarotene and tazarotene benzoate could not be detected in the receiving medium of the assay (i.e. did not pass through the skin), tazarotene sulfoxide was detected in the receiving medium, as shown in FIG. 6.

Tazarotenic acid was not detected under these experimental conditions.

Example 3

Retinoid Activity of Tazarotene, Tazarotene Benzoate and Tazarotene Metabolites

A study was conducted to evaluate the retinoid activity of tazarotene, tazarotene benzoate and tazarotene metabolites (tazarotenic acid, tazarotene sulfone, tazarotenic acid sulfone and tazarotenic acid sulfoxide).

SkinEthic RHE cultures were transferred into 6-well plates containing 1.0 mL/well growth media. The cultures were equilibrated at 37° C. and the media was changed daily. The cultures were subsequently placed in 60 mm petri dishes containing 3.5 mL growth media. 6 μl aliquots of the Test Articles shown in Table 3 were applied to duplicate cultures. The cultures were incubated at 37° C. for 72 hours. At the end of the incubation period, the growth media was collected and stored at −20° C. The tissues were cut in half and one half was placed in 10% NBF for histology, while the other half was placed in RNAlater™ solution (Ambion). The following analyses were performed: a) IL-1α and IL-8 activity assay; b) H and E staining; c) Immunohistochemistry for K10, K19 and filaggrin; and d) qRT-PCR to quantitate K10, K19 and filaggrin expression.

TABLE 3

| | Test Articles |
|---|---|
| 1 | Untreated (negative control) |
| 2 | Octyldodecanol (OD) vehicle control |
| 3 | TAZORAC ® 0.1% cream |
| 4 | Retin-A Micro ® 0.04% (tretinoin) gel |
| 5 | Tretinoin (0.1% in OD) |
| 6 | Tazarotene (0.1% in OD) |
| 7 | Tazarotenic acid (0.1% in OD) |
| 8 | Tazarotene benzoate (0.1% in OD) |
| 9 | Tazarotene sulfone (0.1% in OD) |
| 10 | Tazarotenic acid sulfoxide (0.1% in OD) |
| 11 | Tazarotenic acid sulfone (0.1% in OD) |

Figure 7:
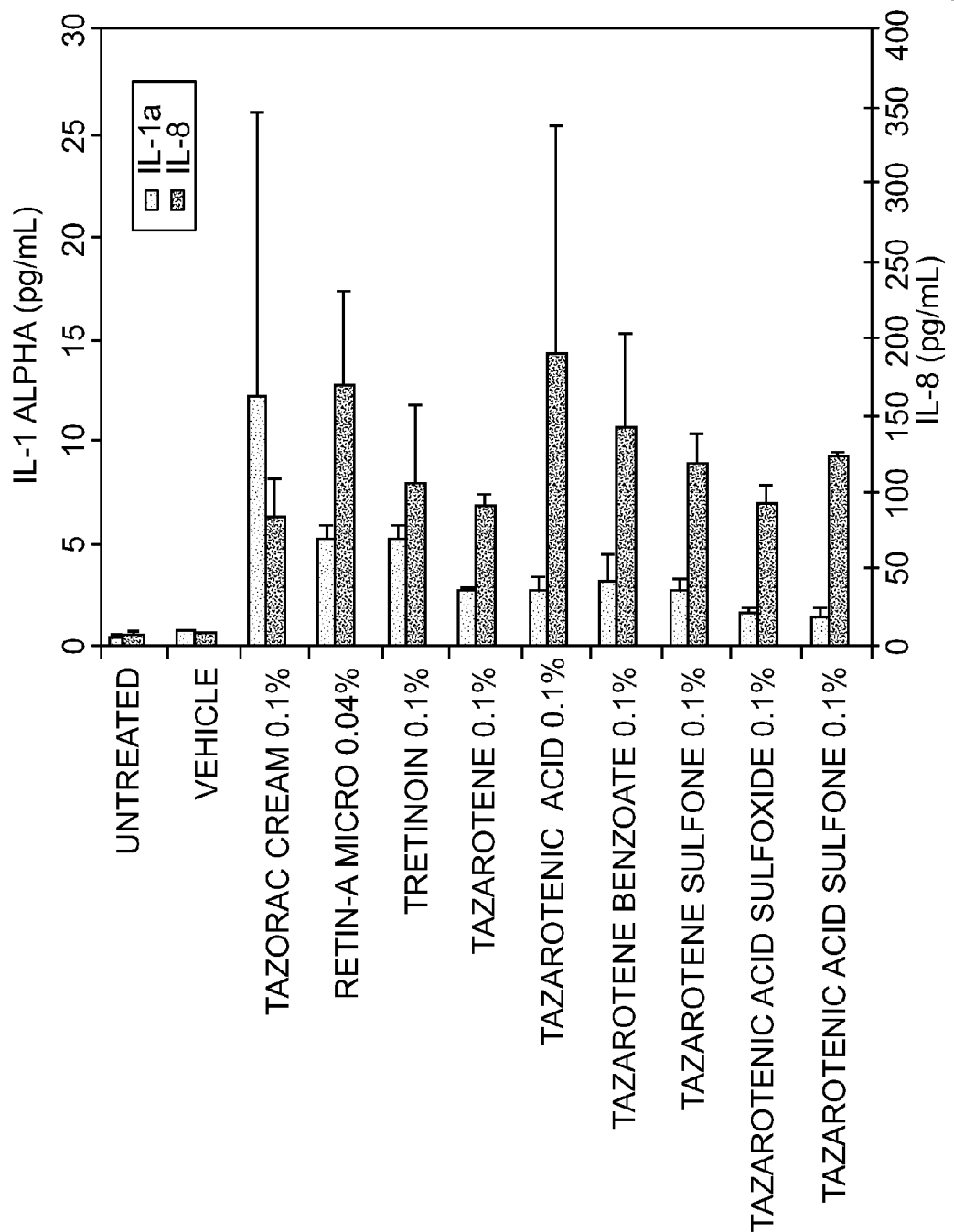
FIG. 7 illustrates pro-inflammatory cytokine (IL-1α and IL-8) release from SkinEthic RHE cultures following exposure to various retinoids. Each bar represents the average of duplicate cultures (±Stdev).
Figure 15:
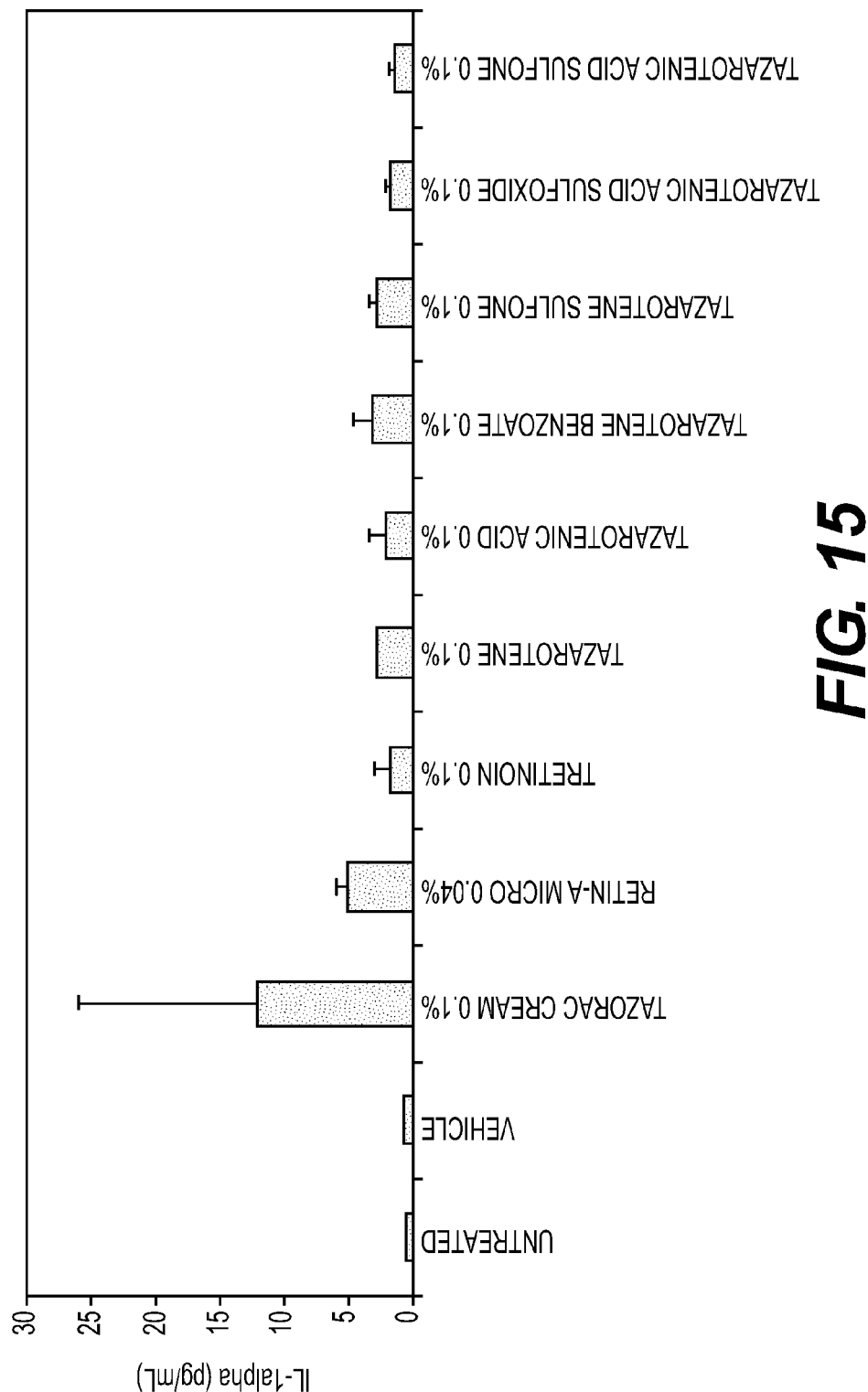
FIG. 15 illustrates the amount of IL-1α released in the presence of various retinoids.
Figure 16:
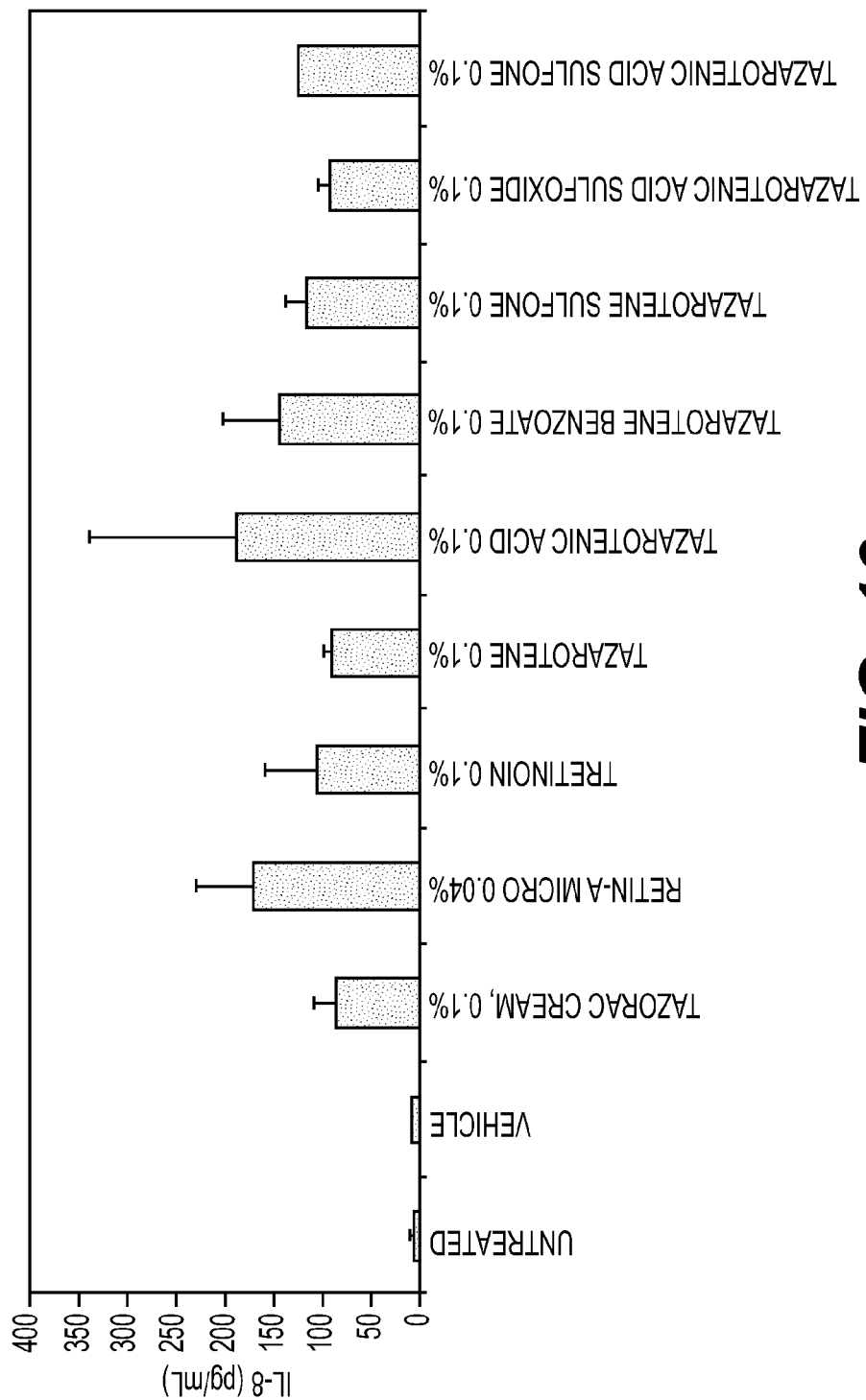
FIG. 16 illustrates the amount of IL-8 released in the presence of various retinoids.
Figure 17:
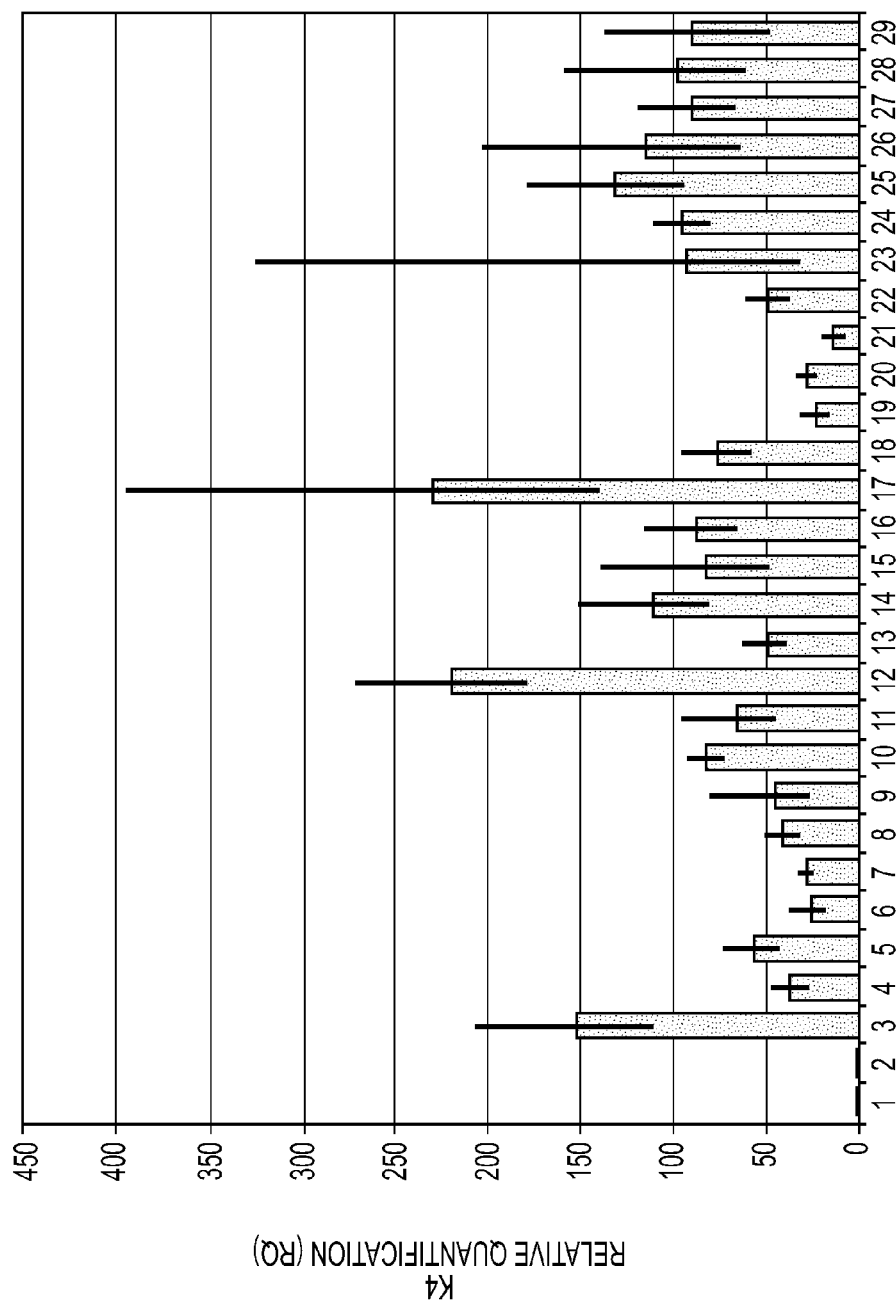
FIG. 17 illustrates the biological (retinoid) activity of various metabolites and analogues of tazarotene benzoate i.e. by determining gene expression levels for K4. The respective metabolites and analogues are shown in Table 11 (labeled compounds 1 to 29).
Figure 18:
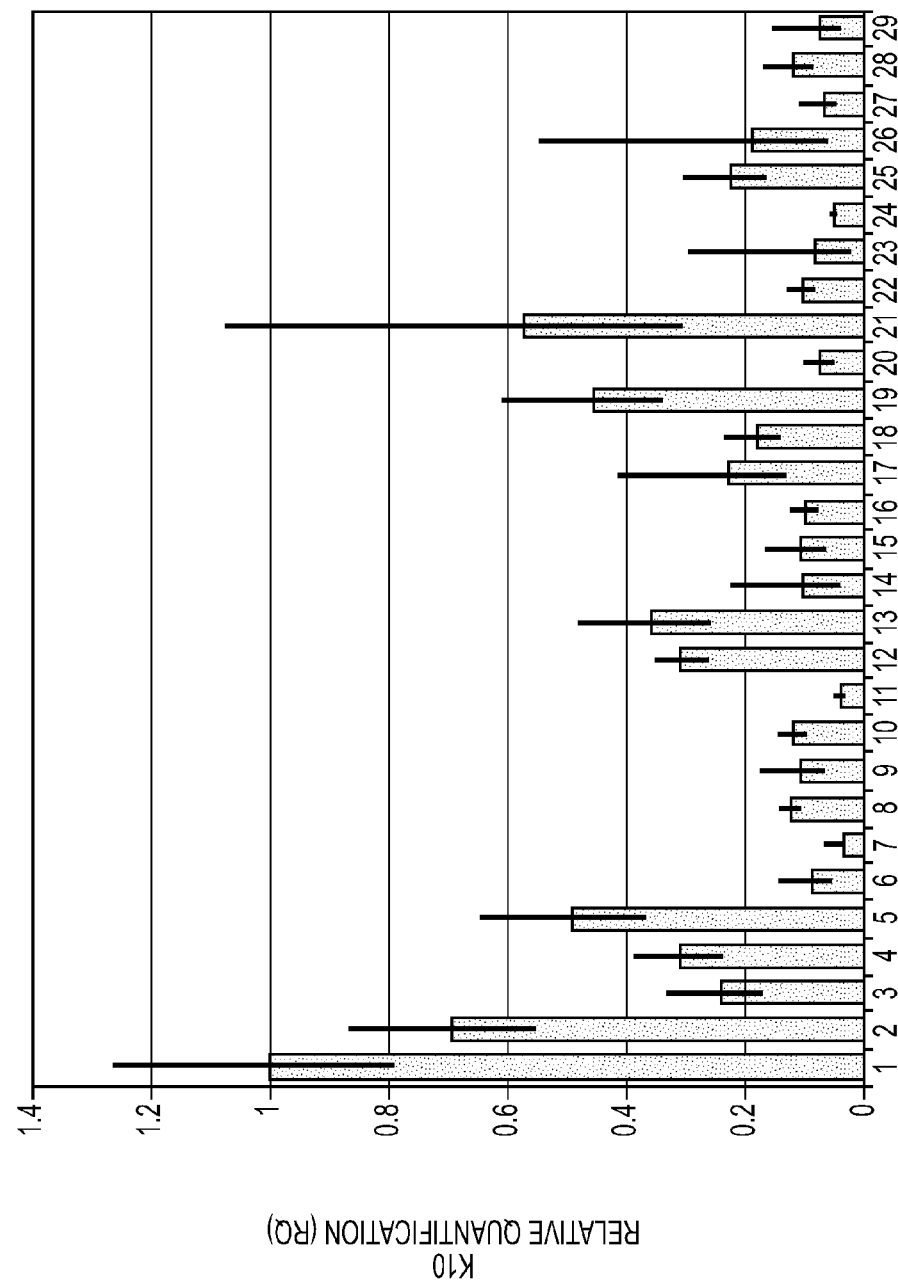
FIG. 18 illustrates the biological (retinoid) activity of various metabolites and analogues of tazarotene benzoate i.e. by determining gene expression levels for K10. The respective metabolites and analogues are shown in Table 11.
Figure 19:
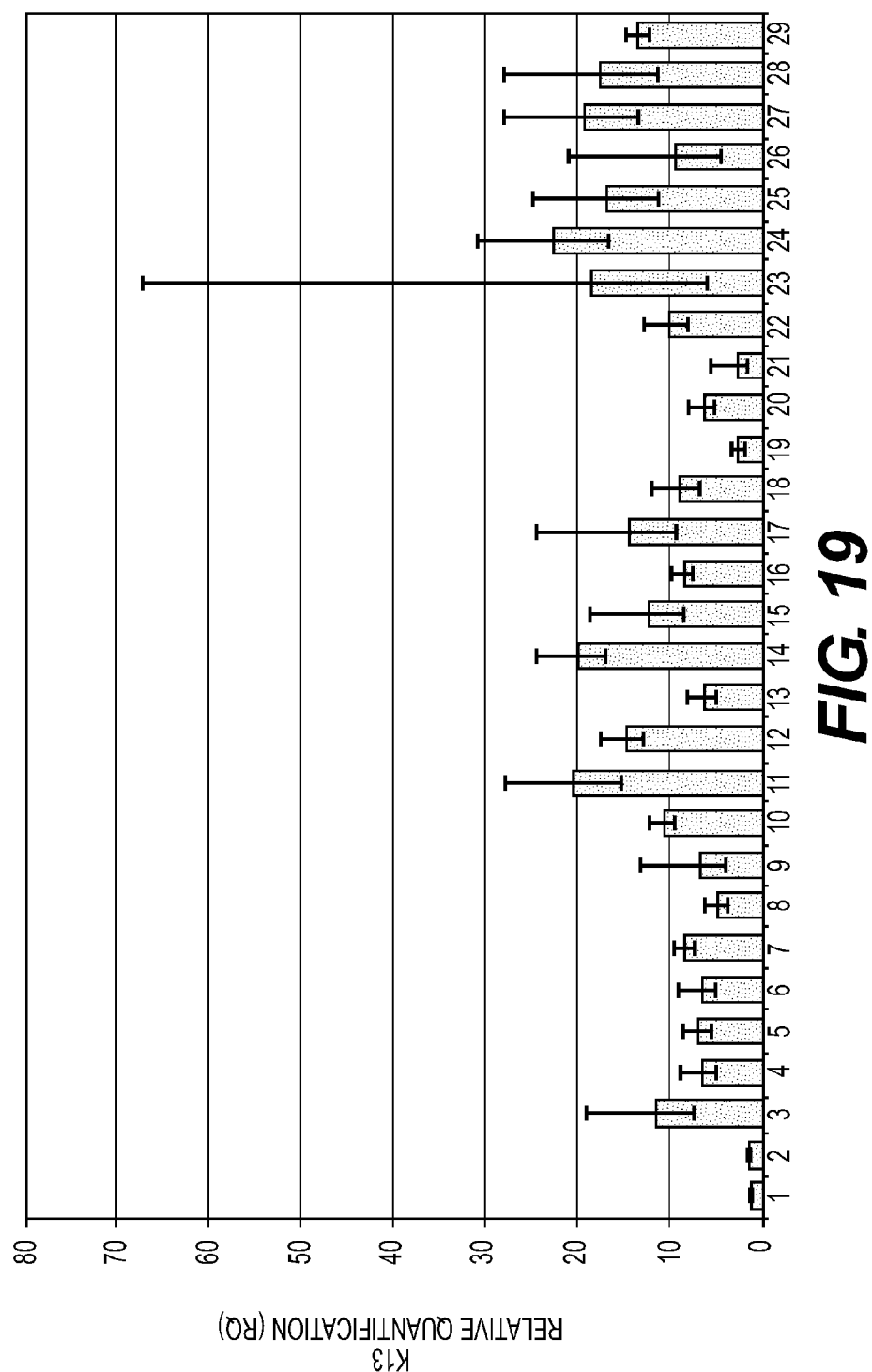
FIG. 19 illustrates the biological (retinoid) activity of various metabolites and analogues of tazarotene benzoate i.e. by determining gene expression levels for K13. The respective metabolites and analogues are shown in Table 11.
Figure 20:
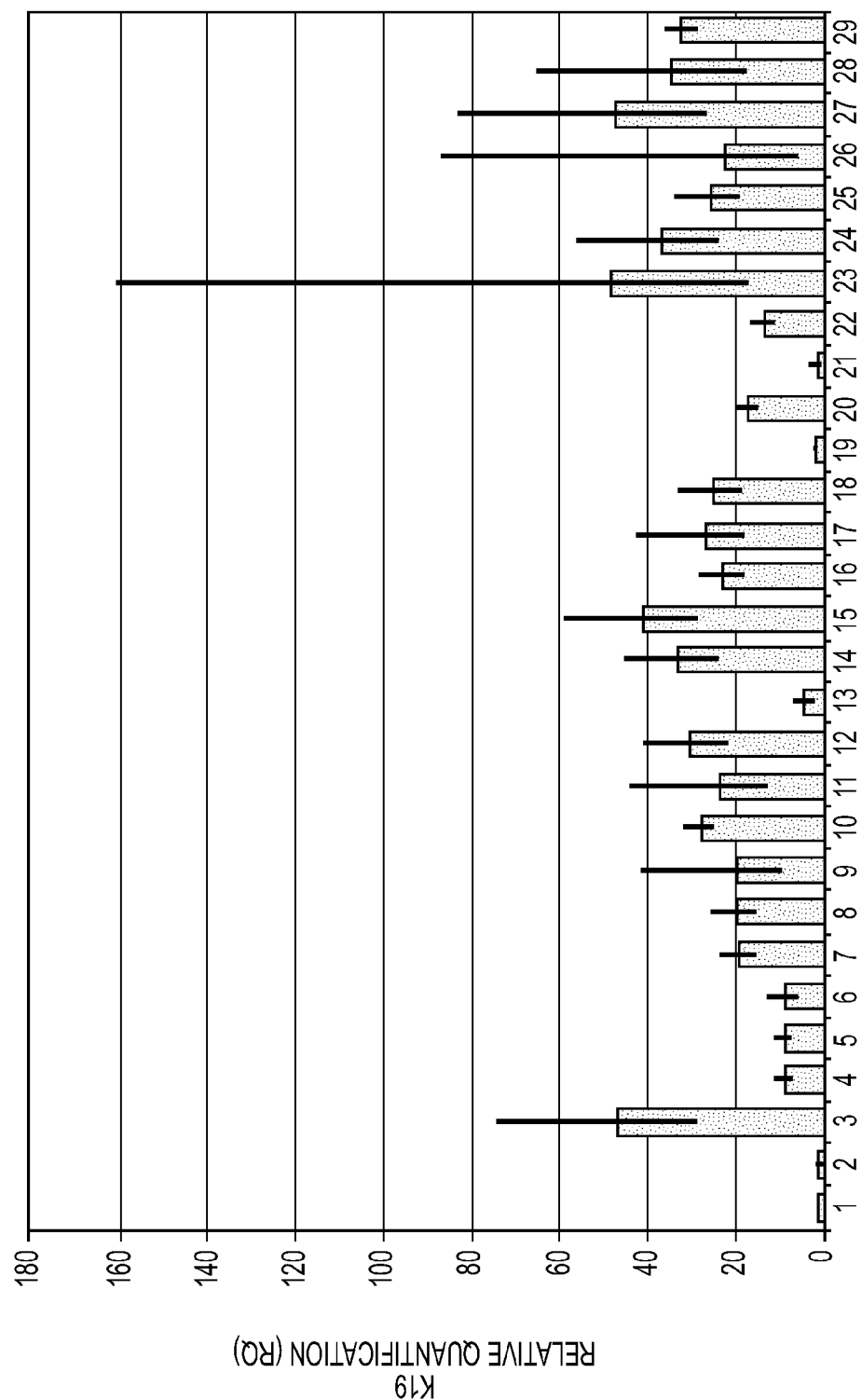
FIG. 20 illustrates the biological (retinoid) activity of various metabolites and analogues of tazarotene benzoate i.e. by determining gene expression levels for K19. The respective metabolites and analogues are shown in Table 11.
Figure 21:
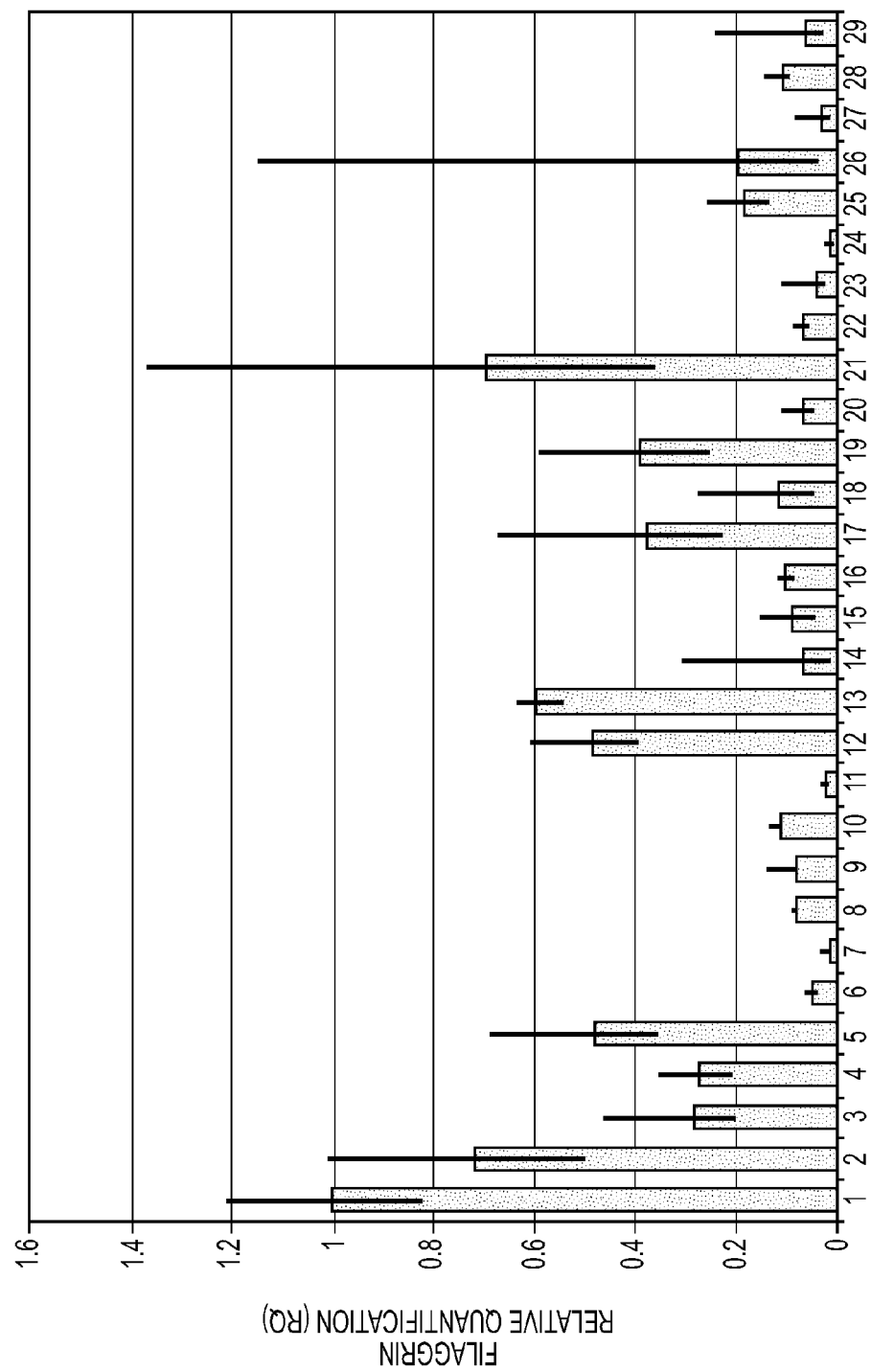
FIG. 21 illustrates the biological (retinoid) activity of various metabolites and analogues of tazarotene benzoate i.e. by determining gene expression levels for filaggrin. The respective metabolites and analogues are shown in Table 11.

The study demonstrated that interleukin-1α (IL-1α) (a pro-inflammatory cytokine) activity was only slightly increased in cultures treated with tazarotene, tazarotene benzoate or tazarotene metabolites compared to untreated and vehicle controls (FIGS. 7 and 15). However, IL-1α activity was significantly increased in cultures treated with TAZORAC cream, and to a lesser extent with Retin-A Micro® tretinoin gel, suggesting that formulation excipients may contribute to the irritation potential of retinoids. Furthermore, interleukin-8 (IL-8) (a pro-inflammatory cytokine specific to retinoids) was significantly increased in all cultures treated with retinoids compared to untreated and vehicle treated controls, suggesting that tazarotene, tazarotene benzoate and the tazarotene metabolites have retinoid activity (FIGS. 7 and 16).

The histological profiles of cultures treated with TAZORAC cream or Retin-A Micro gel were as expected: namely, there was a decrease in keratohyalin granules (Hand E), a decrease in K10 expression in the suprabasal layers, and an increase in K19 expression in all viable cell layers, compared to untreated controls. Histological profiles for cultures treated with tazarotene, tazarotene benzoate and the tazarotene metabolites were similar to those of TAZORAC cream and Retin-A Micro gel, providing further evidence that they have retinoid activity.

Following the histological profile study, gene expression profiles for K10, K19 and filaggrin in RHE cultures treated with the various retinoids were examined Gene expression profiles were consistent with histological observations. There was a 3- to 1000-fold down regulation of K10 in all retinoid-treated cultures compared to untreated and vehicle controls, with the possible exception of tazarotene benzoate, which was uninterpretable due to a high standard deviation. In addition, there was a 15- to 1500-fold up regulation of K19 in all retinoid-treated cultures compared to untreated and vehicle controls. There was also a 2- to 15-fold down regulation of filaggrin in all retinoid-treated cultures compared to untreated and vehicle controls. The filaggrin expression after treatment with tazarotene benzoate appeared equivocal due to a high variability in one culture. However, the immunohistochemistry illustrates that filaggrin is down regulated by tazarotene benzoate.

The results of these studies provide strong evidence that tazarotene, tazarotene benzoate and the tazarotene metabolites have retinoid activity in human skin.

Example 4

Retinoid Activity of Tazarotene Benzoate

A study was conducted to specifically evaluate the retinoid activity of tazarotene benzoate, using a human keratinocyte model (A431).

A431 cells were purchased from ATCC(CRL-1555). Cells were seeded onto 12-well plates at a density of 250,000 cells/well and incubated for 72 hours at 37° C./5% $CO_2$ to allow cells to grow to confluency. Phorbol-12-myristate 13-acetate (PMA), diluted in DMSO (10 mg/mL stock), was added in a concentration of 10 ng/mL and retinoids were added in concentrations of 0.01 to 1 μg/mL from a 10 mg/mL stock solution in DMSO. Cultures were incubated for 48 hours at 37° C. At the end of the incubation period, growth media was collected and cell viability was determined using a CellTiterGlo assay kit (Promega). Concentrations of IL-6 were determined by ELISA and normalized based on cell viability.

It is known that PMA up regulates IL-6 expression through transactivation of the nuclear transcription factor, AP-1. Retinoids, such as tretinoin, are known to inhibit transactivation of AP-1 via retinoic acid receptors.

Figure 8:
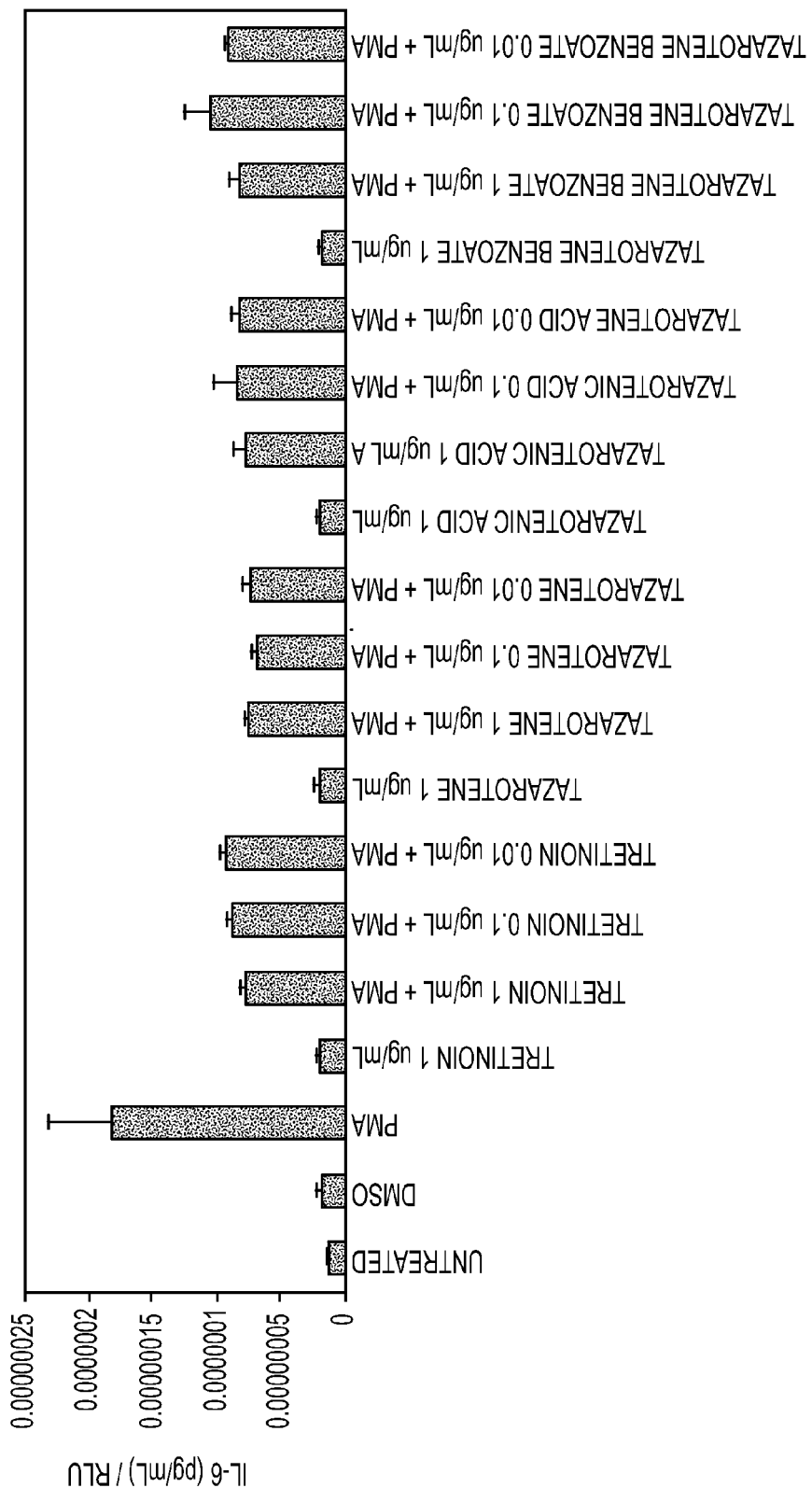
FIG. 8 illustrates the PMA-induced IL-6 release from A431 cultures following exposure to various retinoids. Each bar represents the average of triplicate cultures (±Stdev).

The study illustrated that PMA-induced IL-6 release was significantly decreased in cultures treated with tazarotene benzoate, and was similar to the results obtained for cultures treated with tretinoin, tazarotene and tazarotenic acid (FIG. 8).

As such, these results provide further evidence that tazarotene benzoate has retinoid activity in human skin.

Example 5

Stability of Tazarotene Benzoate in Plasma

To further characterize tazarotene benzoate, the stability of tazarotene benzoate, tazarotene sulfoxide and tazarotene in human and rat plasma was studied.

Tazarotene, tazarotene sulfoxide and tazarotene benzoate were incubated at room temperature with human and rat plasma. The incubation was carried out in duplicate and samples were taken at specific time points for stability analyses (i) rat samples (0 hour, 2 hours and 4 hours) and (ii) human samples (0 hour, 2 hours, 4 hours and 8 hours). Samples were analyzed by LC-MS/MS.

Figure 9:
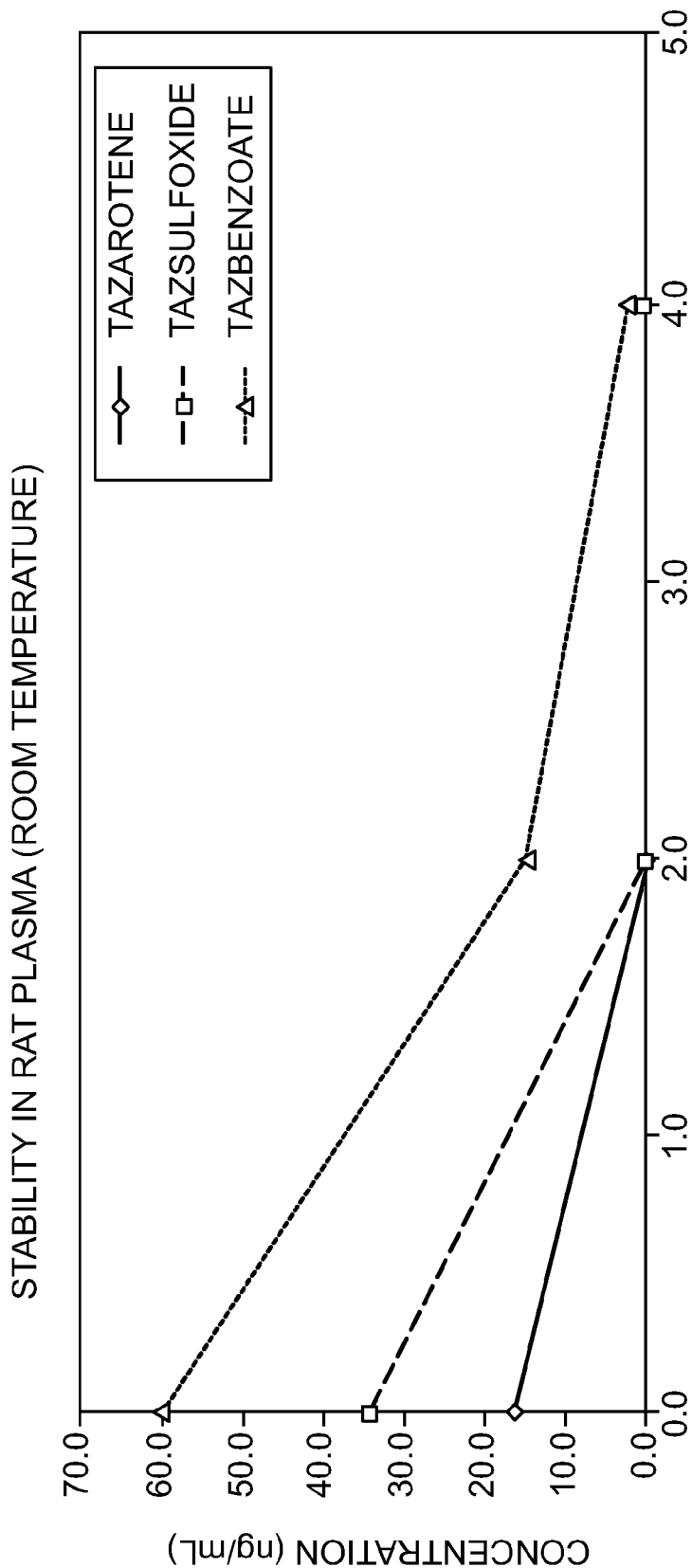
FIG. 9 illustrates the stability of tazarotene, tazarotene sulfoxide and tazarotene benzoate in rat plasma at room temperature.
Figure 10:
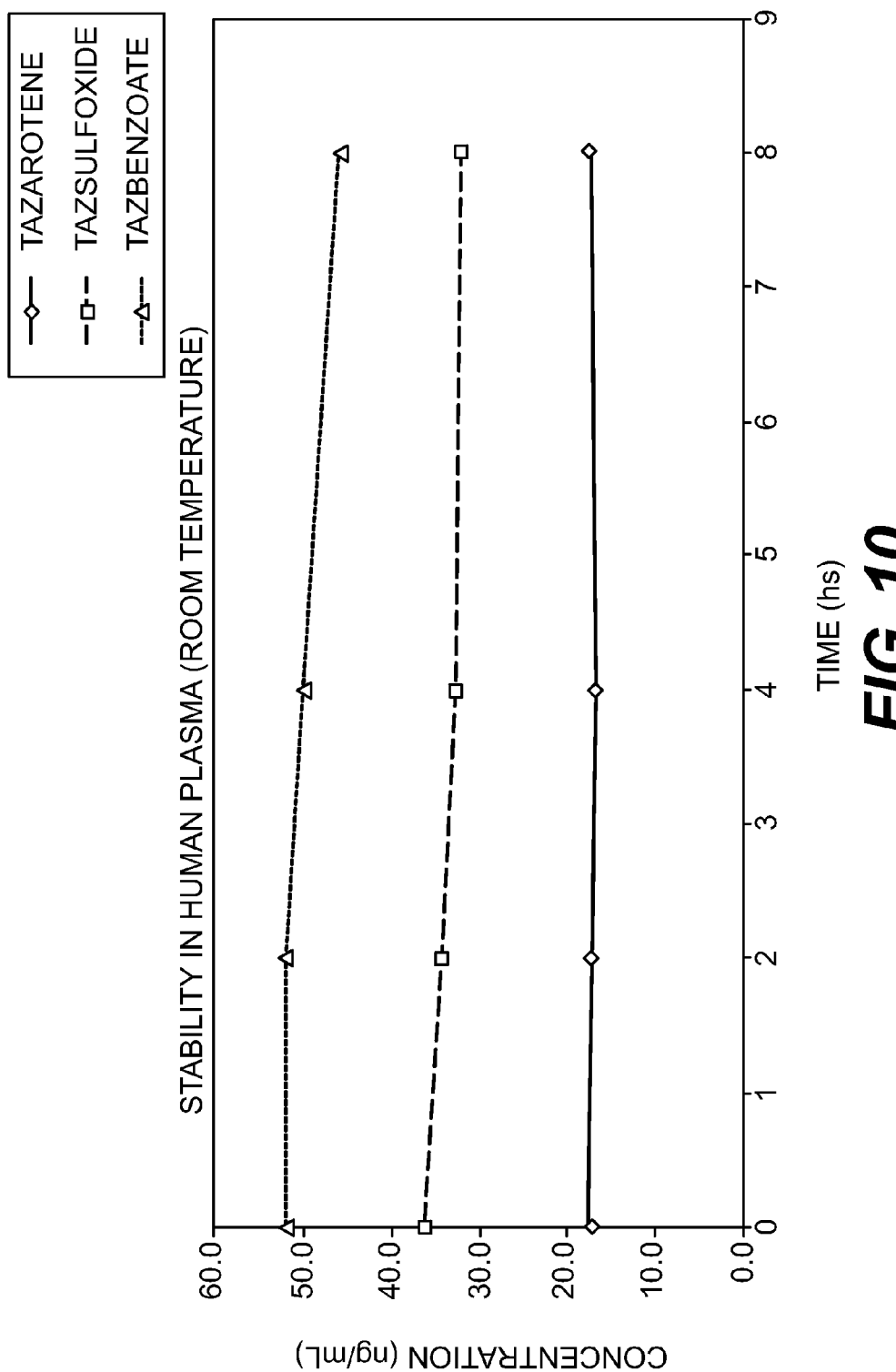
FIG. 10 illustrates the stability of tazarotene, tazarotene sulfoxide and tazarotene benzoate in human plasma at room temperature.
Figure 11:
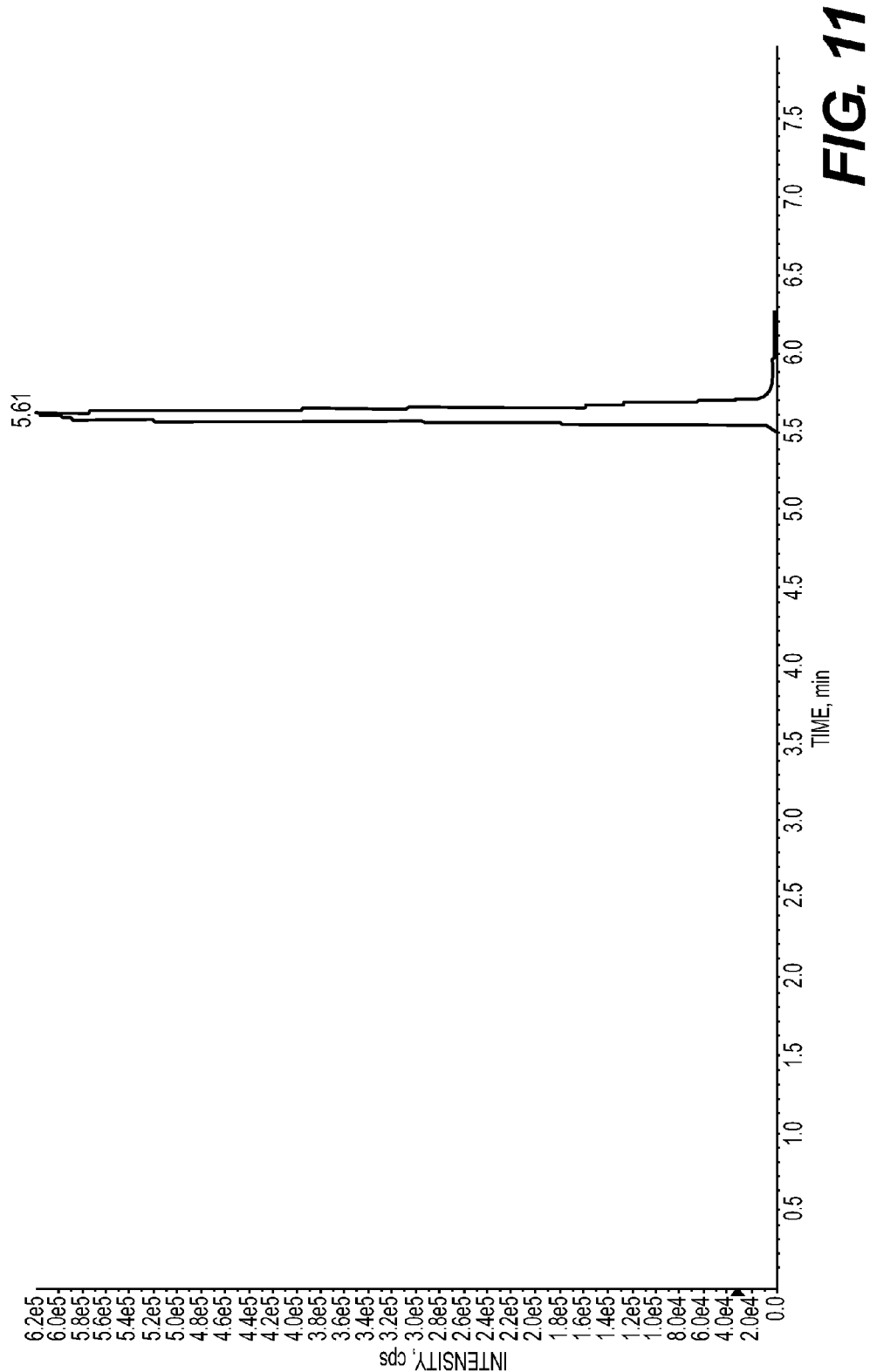
FIG. 11 illustrates the peak for tazarotene benzoate measured with a Shimadzu HPLC-Applied Biosystems 4000 QTRAP.

The study demonstrates that in rat plasma, tazarotene, tazarotene sulfoxide and tazarotene benzoate showed rapid degradation, with 75-100% loss in 2 hours (Table 4 and FIG. 9). In human plasma, the rate of degradation of tazarotene, tazarotene sulfoxide and tazarotene benzoate was significantly slower, with <10% loss at 2 hours and <15% loss by 8 hours (Table 5 and FIG. 10). The degradation products were the corresponding ester hydrolysis products of each compound tested.

TABLE 4

| Rat plasma | 0 hour | 2 hours | 4 hours |
|---|---|---|---|
| Tazarotene (ng/mL) | 16.4 | <LOD | <LOD |
| Tazarotene sulfoxide (ng/mL) | 34.1 | <LOD | <LOD |
| Tazarotene benzoate (ng/mL) | 59.8 | 15.0 | 2.29 |

TABLE 5

| Human plasma | 0 hour | 2 hours | 4 hours | 8 hours |
|---|---|---|---|---|
| Tazarotene (ng/mL) | 17.1 | 17.1 | 16.6 | 17.5 |
| Tazarotene sulfoxide (ng/mL) | 36.2 | 34.0 | 32.2 | 31.9 |
| Tazarotene benzoate (ng/mL) | 52.0 | 52.0 | 50.0 | 45.8 |

Example 6

Metabolism of Tazarotene, Tazarotene Sulfoxide, Tazarotenic Acid and Tazarotene Benzoate in the Presence of Human Liver Microsomes The metabolic stability of tazarotene, tazarotene sulfoxide, tazarotenic acid and tazarotene benzoate in the presence of human liver microsomes was studied.

Hepatic microsomal reactions were carried out in microcentrifuge tubes in the following manner. Human liver microsomes (0.5 or 1.0 mg/ml protein), Test Article (1 or 10 μM), paraoxon (0, 10 or 100 μM), NADPH regenerating system (10 mM glucose-6-phosphate, 1 unit/ml glucose-6-phosphate dehydrogenase, 1 mM NADP$^+$), magnesium chloride (5 mM) in 0.1 M potassium phosphate buffer, pH 7.4 were incubated at 37° C. in a shaking water bath. Reactions were initiated with the addition of substrate with the exception of the zero-time incubations. The total reaction volume was 0.2 ml. The reactions were incubated for 15, 30, 45 or 60 minutes, terminated with 0.2 ml ice-cold acetonitrile and then placed on ice. For zero-time incubations, ice cold acetonitrile was added to the mixture containing microsomes, along with NADPH regenerating system, magnesium chloride in phosphate buffer and the Test Article. Each time point was carried out in triplicate.

Disappearance of Test Article and formation of metabolites following in vitro metabolism were determined by LC-MS/MS using multiple reaction monitoring. LightSight® software (Applied Biosystems, Foster City, Calif.) was used to generate the mass spectrometry methods and carry out the data mining.

Control incubations were carried out with the identical incubation procedures as described above with the following exceptions. In negative control reactions, microsomes were not included. Positive control incubations for liver microsomes included an assessment of the microsomal stability of 7-ethoxycoumarin, which is quickly metabolized by CYPs in liver microsomal incubations of laboratory animals and humans. Duplicate reactions with an initial concentration of 10 μM were incubated for 0 or 30 minutes. Microsomal metabolic stability of 7-ethoxycoumarin was determined by LC-MS/MS.

TABLE 6

Metabolism of tazarotene, tazarotene sulfoxide, tazarotenic acid and tazarotene benzoate

| Compound | Enzyme System | Conc (μM) | Type of reaction | k constant | R-squared | Half-life (min) | $CL_{int}$* |
|---|---|---|---|---|---|---|---|
| Tazarotene | HLM | 1 | Complete | −0.0880 | 0.977 | 7.88 | 176 |
| | | | Without NADPH | −0.0899 | 0.981 | 7.71 | 180 |
| | | 10 | Complete | −0.0827 | 0.988 | 8.38 | 165 |
| | | | Without NADPH | −0.0914 | 0.988 | 7.58 | 183 |
| Tazarotene sulfoxide | HLM | 1 | Complete | −0.0689 | 0.963 | 10.1 | 138 |
| | | | Without NADPH | −0.0779 | 0.994 | 8.90 | 156 |
| | | 10 | Complete | −0.0647 | 0.977 | 10.7 | 129 |
| | | | Without NADPH | −0.0763 | 0.995 | 9.08 | 153 |
| Tazarotenic acid | HLM | 1 | Complete | −0.0064 | 0.980 | 108 | 6.40 |
| | | | Without NADPH | 0.0003 | 0.124 | 0.00 | 0.00 |
| | | 10 | Complete | −0.0047 | 0.596 | 147 | 4.70 |
| | | | Without NADPH | 0.0006 | 0.037 | 0.00 | 0.00 |
| Tazarotene benzoate | HLM | 1 | Complete | −0.0893 | 0.967 | 7.76 | 179 |
| | | | Without NADPH | −0.0964 | 0.954 | 7.19 | 193 |
| | | 10 | Complete | −0.0097 | 0.897 | 71.4 | 9.70 |
| | | | Without NADPH | −0.0146 | 0.980 | 47.5 | 14.6 |
| Tazarotene benzoate | HSkM | 1 | Complete | −0.0014 | 0.656 | 495 | 0.700 |
| | | | Without NADPH | −0.0032 | 0.360 | 217 | 1.60 |
| | | 10 | Complete | −0.0017 | 0.283 | 408 | 0.850 |
| | | | without NADPH | −0.0015 | −0.194 | 462 | 0.800 |

*= ml/min/mg 15.4% to 19.8% of tazarotene was converted to tazarotenic acid in complete non-zero minute incubations (with NADPH) (Table 7). In the absence of NADPH, incubations contained higher concentrations of tazarotenic acid (32.4% to 52.7% of tazarotene converted). Tazarotenic acid makes up only a fraction of the metabolism, suggesting the existence of other metabolic pathways such as sulfoxidation to tazarotene sulfoxide or additional metabolism of tazarotenic acid to tazarotenic acid sulfoxide and tazarotenic acid sulfone.

TABLE 7

Metabolism of tazarotene to tazarotenic acid

| | | Percent of initial tazarotene concentration | | | | | |
|---|---|---|---|---|---|---|---|
| | | 1 μM initial concentration | | | 10 μM initial concentration | | |
| Type of Reaction | Incubation time (min) | Tazarotene | Tazarotenic acid | Total | Tazarotene | Tazarotenic acid | Total |
| Complete (with NADPH) | 0 | 100% | 0.00% | 100% | 100% | 0.00% | 100% |
| | 15 | 21.1% | 18.0% | 39.1% | 24.1% | 15.4% | 39.5% |
| | 30 | 4.91% | 19.6% | 24.5% | 6.55% | 18.4% | 24.9% |
| | 45 | 1.80% | 19.6% | 21.4% | 2.18% | 18.3% | 20.4% |
| | 60 | 0.70% | 19.8% | 20.5% | 0.89% | 17.4% | 18.3% |

TABLE 7-continued

Metabolism of tazarotene to tazarotenic acid

Percent of initial tazarotene concentration

| Type of Reaction | Incubation time (min) | 1 µM initial concentration | | | 10 µM initial concentration | | |
|---|---|---|---|---|---|---|---|
| | | Tazarotene | Tazarotenic acid | Total | Tazarotene | Tazarotenic acid | Total |
| Without NADPH | 0 | 100% | 0.00% | 100% | 100% | 0.00% | 100% |
| | 15 | 22.0% | 37.2% | 59.2% | 21.9% | 32.4% | 54.3% |
| | 30 | 4.86% | 44.7% | 49.6% | 4.64% | 39.5% | 44.1% |
| | 45 | 1.43% | 48.5% | 49.9% | 1.48% | 41.3% | 42.8% |
| | 60 | 0.65% | 52.7% | 53.4% | 0.55% | 40.5% | 41.1% |

Tazarotene sulfoxide was also rapidly metabolized in human liver microsomes (Table 8). Near-quantitative conversion to the tazarotenic acid sulfoxide was observed for 1 µM reactions as shown in the mass balance calculations. In the case of 1 µM reactions without NADPH, the percentage values of tazarotene sulfoxide converted to tazarotenic acid sulfoxide were over 100%. This is an unexpected result which may be due to ion suppression effects between standard and sample injections. For 10 µM substrate reactions, greater than 50% of the Test Article metabolized to tazarotenic acid sulfoxide. In the presence of NADPH, tazarotenic acid sulfoxide was a major metabolite, but its levels were lower than those observed in incubations without NADPH. Only a fraction of NADPH-dependent metabolism is detected as tazarotenic acid sulfoxide. This suggests other metabolic pathways either by oxidation of tazarotene sulfoxide to its sulfone or by additional metabolism of tazarotenic acid sulfoxide to its sulfone.

TABLE 8

Metabolism of tazarotene sulfoxide to tazarotenic acid sulfoxide

Percent of initial tazarotene sulfoxide concentration

| Type of Reaction | Incubation time (min) | 1 µM initial concentration | | | 10 µM initial concentration | | |
|---|---|---|---|---|---|---|---|
| | | Tazarotene sulfoxide | Tazarotenic acid sulfoxide | Total | Tazarotene sulfoxide | Tazarotenic acid sulfoxide | Total |
| Complete (with NADPH) | 0 | 100% | 0.00% | 100% | 100% | 0.00% | 100% |
| | 15 | 25.6% | 43.1% | 68.7% | 30.9% | 27.7% | 58.6% |
| | 30 | 8.86% | 50.8% | 59.7% | 11.4% | 38.3% | 49.7% |
| | 45 | 4.24% | 55.4% | 59.7% | 4.80% | 38.4% | 43.2% |
| | 60 | 2.17% | 56.7% | 58.9% | 2.70% | 41.0% | 43.7% |
| Without NADPH | 0 | 100% | 0.00% | 100% | 100% | 0.00% | 100% |
| | 15 | 27.9% | 87.1% | 115% | 30.4% | 58.4% | 88.8% |
| | 30 | 8.40% | 108% | 116% | 8.96% | 74.2% | 83.2% |
| | 45 | 2.72% | 112% | 115% | 2.98% | 76.6% | 79.6% |
| | 60 | 1.11% | 116% | 117% | 1.18% | 79.1% | 80.3% |

Figure 14:
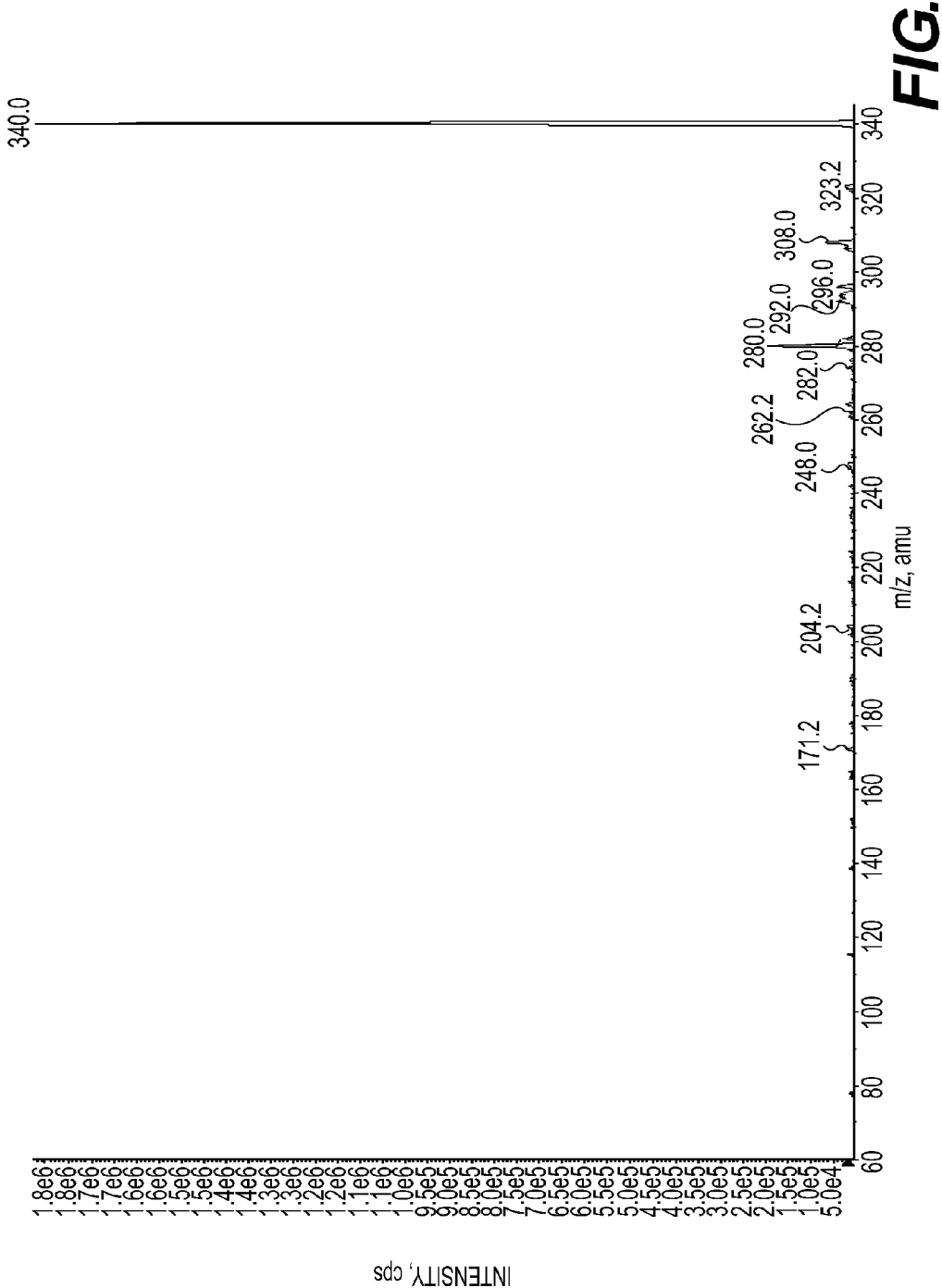
FIG. 14 illustrates the mass spectra fragmentation of tazarotenic acid sulfoxide.

In the presence of NADPH, tazarotenic acid was slowly metabolized by human liver microsomes to tazarotenic acid sulfoxide (Table 9). Tazarotenic acid was not metabolized in the absence of NADPH. A mass spectrum for tazarotenic acid sulfoxide is shown in FIG. 14.

TABLE 9

Metabolism of tazarotenic acid to tazarotenic acid sulfoxide

Percent of initial tazarotenic acid concentration

| Type of Reaction | Incubation time (min) | 1 µM initial concentration | | | 10 µM initial concentration | | |
|---|---|---|---|---|---|---|---|
| | | tazarotenic acid | tazarotenic acid sulfoxide | Total | tazarotenic acid | tazarotenic acid sulfoxide | Total |
| Complete (with NADPH) | 0 | 100% | 0.00% | 100% | 100% | 0.00% | 100% |
| | 15 | 89.9% | 12.6% | 103% | 93.1% | 3.83% | 96.9% |
| | 30 | 82.0% | 22.3% | 104% | 88.6% | 7.68% | 96.3% |
| | 45 | 75.8% | 30.4% | 106% | 77.8% | 10.3% | 88.1% |
| | 60 | 68.0% | 35.9% | 104% | 77.4% | 13.6% | 91.0% |

TABLE 9-continued

Metabolism of tazarotenic acid to tazarotenic acid sulfoxide

Percent of initial tazarotenic acid concentration

| | | 1 µM initial concentration | | | 10 µM initial concentration | | |
|---|---|---|---|---|---|---|---|
| Type of Reaction | Incubation time (min) | tazarotenic acid | tazarotenic acid sulfoxide | Total | tazarotenic acid | tazarotenic acid sulfoxide | Total |
| Without NADPH | 0 | 100% | 0.00% | 100% | 100% | 0.00% | 100% |
| | 15 | 100% | 0.00% | 100% | 102% | 0.01% | 102% |
| | 30 | 101% | 0.00% | 101% | 99.0% | 0.01% | 99.0% |
| | 45 | 102% | 0.00% | 102% | 106% | 0.01% | 106% |
| | 60 | 101% | 0.00% | 101% | 102% | 0.02% | 102% |

Figure 12:
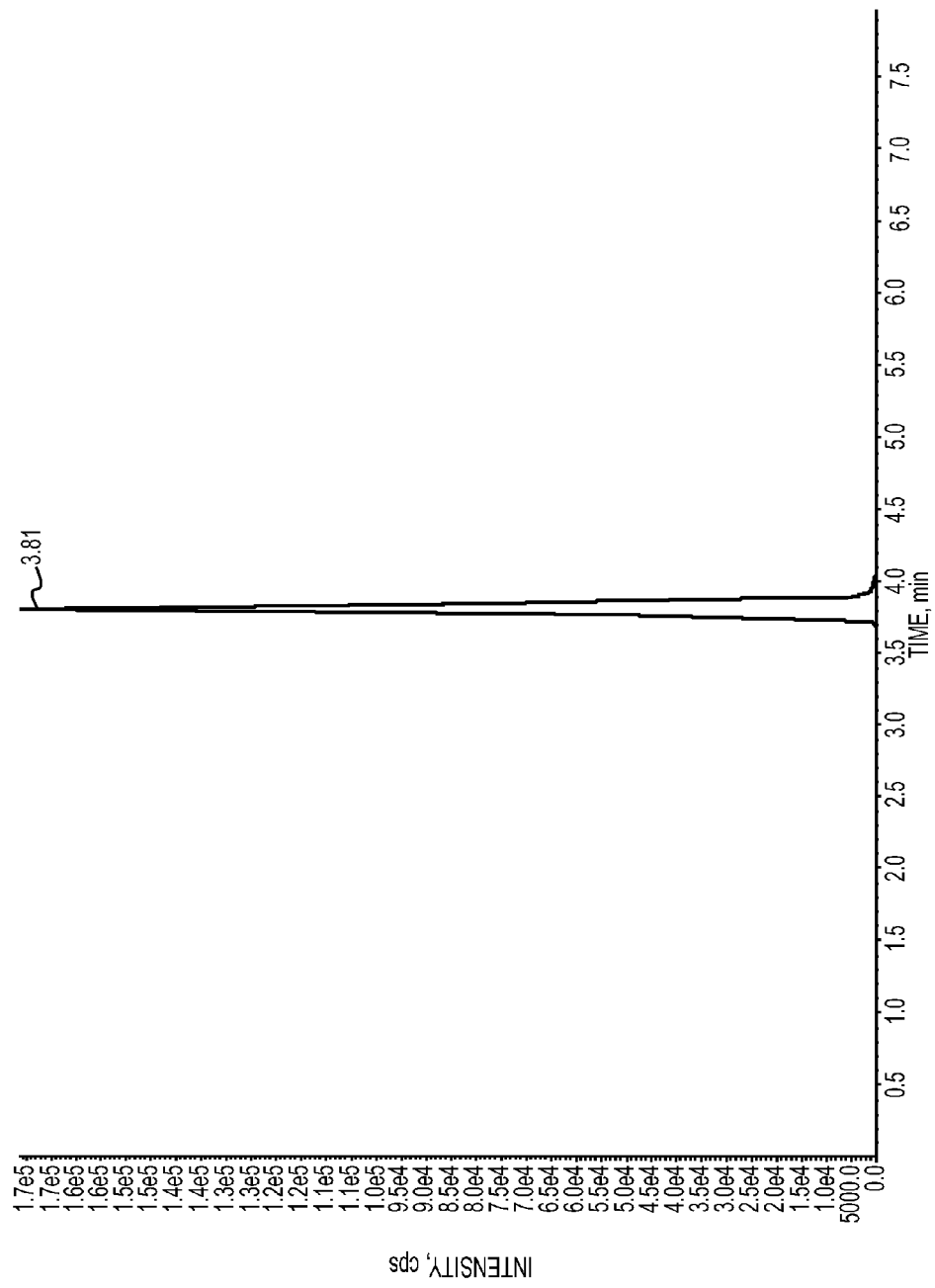
FIG. 12 illustrates the peak for hydroxytazarotenic acid measured with a Shimadzu HPLC-Applied Biosystems 4000 QTRAP.
Figure 13:
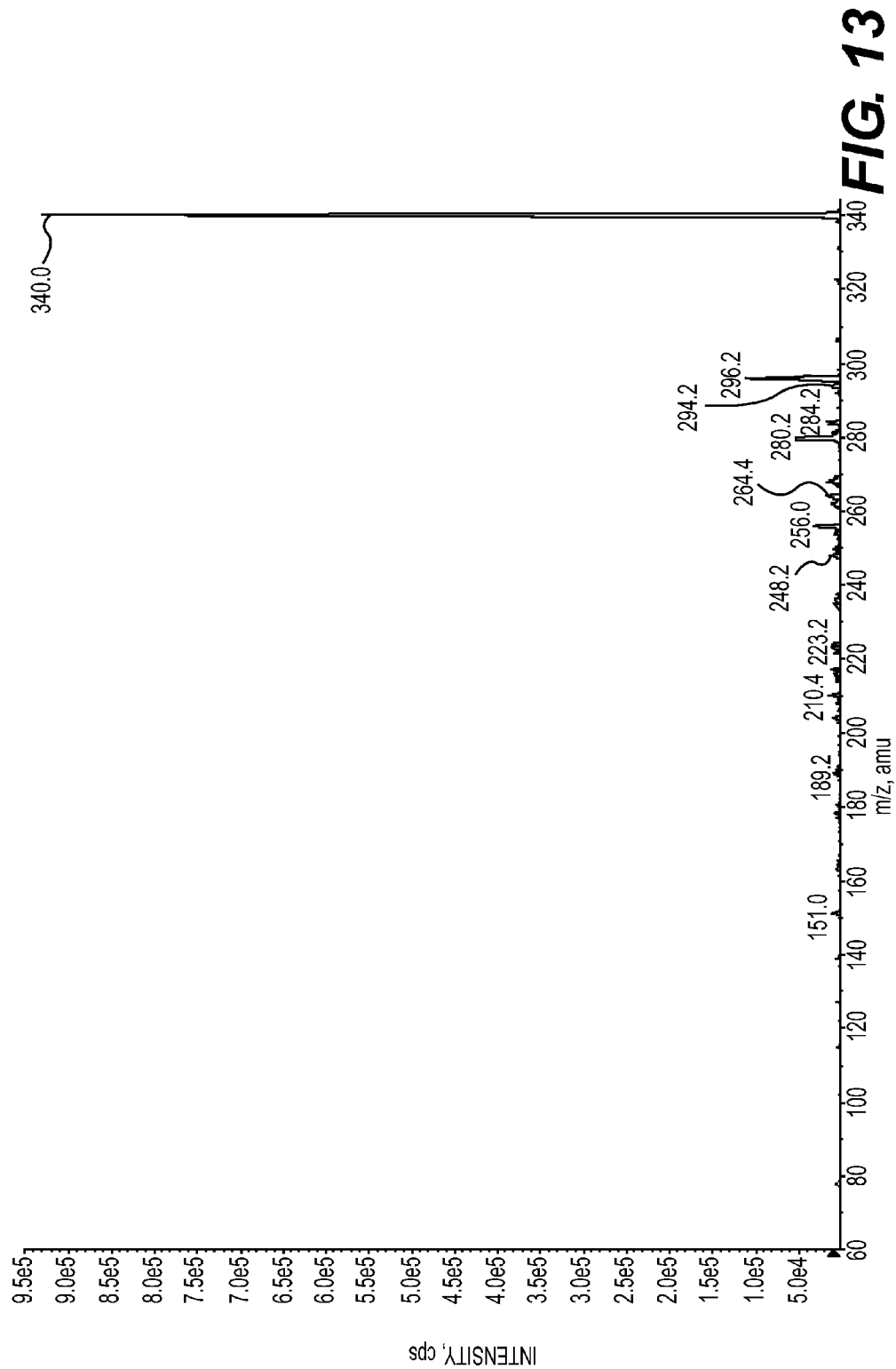
FIG. 13 illustrates the mass spectra fragmentation of hydroxytazarotenic acid.

31.7% to 47.6% of tazarotene benzoate was converted to hydroxy tazarotenic acid in 1 µM reactions with NADPH. Similarly, greater than 50% of tazarotene benzoate was converted to hydroxy tazarotenic acid in 1 µM reactions without NADPH (Table 10). Since the mass balance is significantly less than 100%, particularly for the 1 µM reactions, it appears that other metabolites are also formed. A HPLC chromatogram and mass spectrum corresponding to hydroxy tazarotenic acid is shown in FIGS. 12 and 13, respectively.

Human liver microsomes metabolized 7-ethoxycoumarin as expected, confirming satisfactory incubation conditions for the metabolic stability assay.

Among the metabolites detected, three were identified as tazarotenic acid benzoate (m/z 444), hydroxy tazarotene (m/z 368), and hydroxy tazarotenic acid (m/z 340). Hydroxy tazarotenic acid was identified as a major metabolite. Metabolites with m/z 338 and 366 were also observed. While not bound by the proposal, it is believed that these are products

TABLE 10

Metabolism of tazarotene benzoate to hydroxy tazarotenic acid

Percent of initial tazarotene benzoate concentration

| | | 1 µM initial concentration | | | 10 µM initial concentration | | |
|---|---|---|---|---|---|---|---|
| Type of Reaction | Incubation time (min) | tazarotene benzoate | hydroxy tazarotenic acid | Total | tazarotene benzoate | hydroxy tazarotenic acid | Total |
| Complete (with NADPH) | 0 | 100% | 0.00% | 100% | 100% | 0.00% | 100% |
| | 15 | 20.3% | 31.7% | 52.0% | 99.3% | 6.10% | 105% |
| | 30 | 4.45% | 47.6% | 52.1% | 73.4% | 15.6% | 89.0% |
| | 45 | 1.47% | 43.8% | 45.3% | 63.2% | 24.3% | 87.5% |
| | 60 | 0.73% | 35.2% | 35.9% | 55.2% | 29.2% | 84.4% |
| Without NADPH | 0 | 100% | 0.00% | 100% | 100% | 0.00% | 100% |
| | 15 | 17.3% | 54.5% | 71.8% | 87.0% | 13.2% | 100% |
| | 30 | 2.97% | 71.1% | 74.1% | 64.0% | 32.4% | 96.4% |
| | 45 | 1.07% | 63.1% | 64.2% | 51.0% | 43.2% | 94.2% |
| | 60 | 0.53% | 53.1% | 53.6% | 41.0% | 51.5% | 92.5% |

The study demonstrated that tazarotene, tazarotene sulfoxide, tazarotenic acid and tazarotene benzoate were metabolized by human liver microsomes. Ester hydrolysis is believed to be a major metabolic pathway.

To determine the role of esterases in metabolism of tazarotene, tazarotene sulfoxide, tazarotenic acid and tazarotene benzoate, inhibition studies were carried out with paraoxon, a potent inhibitor of all serine esterases including carboxylesterases. Paraoxon inhibited:
(i) tazarotene metabolism to tazarotenic acid in human liver microsomes,
(ii) tazarotene sulfoxide metabolism to tazarotenic acid sulfoxide in human liver microsomes, and
(ii) tazarotene benzoate metabolism to hydroxy tazarotenic acid in human liver and skin microsomes.

Paraoxon did not inhibit the metabolism of tazarotenic acid to tazarotenic acid sulfoxide, which is a CYP- and FMO-mediated reaction.

Figure 23:
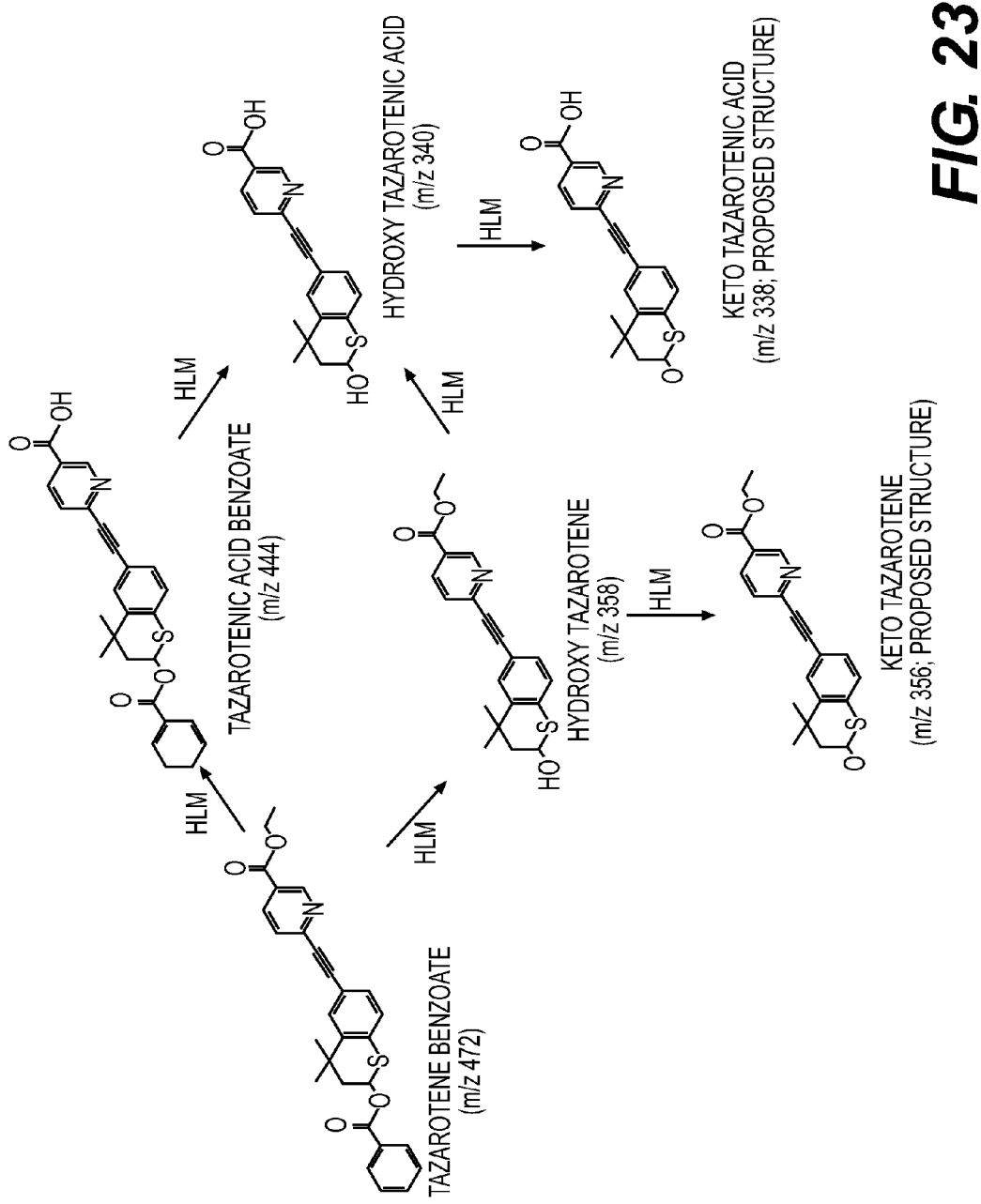
FIG. 23 illustrates the proposed metabolism of tazarotene benzoate.

In all, these results support a conclusion that esterases are responsible for ester hydrolysis of tazarotene, tazarotene sulfoxide and tazarotene benzoate.

following enzymatic oxidation of the thiolactol group to the thiolactone i.e. to form keto tazarotene and keto tazarotenic acid (FIG. 23). In all, these findings are consistent with cleavage of both ester bonds by esterases.

The proposed metabolism of (i) tazarotene and (ii) tazarotene benzoate is illustrated in FIGS. 22 and 23, respectively.

Example 7

Metabolism of Tazarotene Benzoate in the Presence of Human Skin Microsomes

Insofar as several liver microsomal enzymes (including esterases) are found in the human skin, the metabolism of tazarotene benzoate was further studied in vitro in the presence of human skin microsomes.

Five time points were chosen, but because of the limitation of human skin microsome supply, each one was carried out in duplicate. Skin microsomal reactions were carried out as described above for hepatic microsomal reactions with the following two exceptions. Firstly, the total reaction volume was 0.1 mL. Secondly, incubations were terminated with 0.1 mL acetonitrile.

Human skin microsomes catalyzed fexofenadine formation from terfenadine (positive control), confirming drug metabolizing activity of human skin microsomes.

The tazarotene benzoate and hydroxy tazarotenic acid metabolite concentrations were quantified by LC-MS/MS.

The results showed that while tazarotene benzoate was metabolized by the human skin microsomes, the compound was metabolized at a slower rate relative to human liver microsomes i.e. after 150 min, 20% of tazarotenic benzoate was metabolized in the presence of 2 mg/ml human skin microsomes. Formation of hydroxy tazarotenic acid was again observed, suggesting esterase metabolism of tazarotene benzoate.

Example 8

The retinoid activity of tazarotene, tazarotene benzoate, hydroxy tazarotenic acid, keto tazarotenic acid, keto tazarotene and a number of analogues of tazarotene benzoate were evaluated using the following methodology. The compounds are set out in Table 11.

Reconstructed human epidermis (RHE) tissues were cultured in-house as previously described by Poumay et al. Briefly, polycarbonate culture inserts (12 mm diameter and 0.4 µm pore size, Millipore) were filled with 150 µL of a suspension containing approximately $5 \times 10^5$ primary adult human keratinocytes. The inserts received another 500 µL of keratinocyte culture media and were placed in a 6-well plate (1 insert/well) containing 2.5 mL of RHE Growth Media (Epilife media +1.5 mM $CaCl_2$). RHE cultures were incubated at 37° C. in a humidified atmosphere containing 5% $CO_2$, for 24 hours. Subsequently (on Day 0), RHE cultures were exposed to the air-liquid interface by removing the RHE Growth Media from the top of the cultures, and replacing with 1.5 mL/well of RHE Growth Media containing 50 µg/mL vitamin C. Media was changed every other day until the cultures were dosed with Test Articles. A stock solution of 0.1% tazarotene (2.83 mM at 99.5% purity) in OD/10% DMSO was prepared. For tazarotene benzoate, hydroxytazarotenic acid, keto tazarotenic acid, keto tazarotene, and tazarotene nicotinate, a 10 mg/mL stock solution (in DMSO) was already prepared. From this stock solution, a 2.83 mM working solution (in octyldodecanol) was prepared. All other tested compounds were resuspended in DMSO and OD to obtain a final concentration of 2.83 mM in OD/10% DMSO. On Day 12, the cultures were placed in 60 mm petri dishes containing 3 mL of RHE Growth Media (+VitC). Test articles (6 µl) were applied to triplicate cultures and cultures were incubated at 37° C. for 72 hours. Untreated and OD alone served as negative controls. At the end of the incubation period, the growth media was collected and stored at −20° C. The tissues were cut in half: one half was placed in 10% NBF for histology, and the other half was placed in RNAlater™ solution for RT-qPCR. RNA was isolated and concentrations were determined using a NanoDrop spectrophotometer. In addition to using the same amount of RNA for each sample, data was normalized to internal GAPDH mRNA levels and is expressed as relative quantification (RQ) to untreated controls. RNA extracts from each replicate were amplified using RT-qPCR. The relative gene expression of five biomarkers was determined: Keratin 10, Keratin 19, Filaggrin, Keratin 4, and Keratin 13.

The results of the analyses are shown in FIGS. 17 to 21. The compounds displayed on the X axes of FIGS. 17 to 21 correspond to the compounds set out in Table 11. The compounds were ranked for their effect on each biomarker, as set out in Table 12.

Keratin 4 (K4) is not normally expressed in human epidermis but is known to be upregulated upon treatment with retinoids. All tazarotene derivatives caused significant upregulation of K4 (from 11-180-fold) compared to untreated and vehicle controls. Tazarotene, keto tazarotene, compound 17, compound 25 and compound 28 showed the highest increase (from 103 to 180-fold). Compound 21 and compound 19 showed the lowest upregulation with 11 and 19-fold, respectively.

Keratin 10 (K10) is an early differentiation marker that is normally expressed in the suprabasal layers of the viable epidermis, but is known to be downregulated upon treatment with retinoids. With the exception of the S enantiomer of tazarotene benzoate, compound 19 and compound 21, all other tazarotene derivatives caused a significant downregulation of K10 (approximately 7±4-fold) compared to untreated and vehicle controls. The highest K10 downregulation was observed with tazarotene nicotinate, keto tazarotenic acid, and compound 24 (14 to 17-fold).

Keratin 13 (K13) is not normally expressed in human epidermis but is known to be upregulated upon treatment with retinoids. With the exception of compound 19 and compound 21, all tazarotene derivatives caused a significant upregulation of K13 (approximately 13±5-fold) compared to untreated and vehicle controls. The highest K13 upregulation was observed with compound 24 (23-fold), keto tazarotenic acid, and hydroxy tazarotene (20-fold), compound 23 and compound 27 (19-fold), compound 28 (18-fold), and compound 25 (17-fold).

Keratin 19 (K19) is not normally expressed in human epidermis but is known to be upregulated in all the viable layers of the epidermis upon treatment with retinoids. With the exception of compound 19 and compound 21, all other tazarotene derivatives caused a significant upregulation of K19 (approximately 23±11-fold) compared to untreated and vehicle controls. Tazarotene, compound 15, compound 23, compound 24 and compound 27 showed the highest increase (33 to 43-fold).

Filaggrin is a late-stage differentiation marker that is normally expressed in the stratum granulosum and is known to be downregulated upon treatment with retinoids. With the exception of the S enantiomer of tazarotene benzoate, keto tazarotene, compound 13, compound 17, compound 19, and compound 21, all other tazarotene derivatives caused a significant (3-100-fold) downregulation of filaggrin. The highest level of filaggrin downregulation was observed with tazarotene nicotinate (100-fold), compound 24 (56-fold), keto tazarotenic acid (36-fold) and compound 27 (23-fold).

Based on a qualitative assessment of gene expression profiles (Table 12), the top 5 tazarotene derivatives are: compound 24, compound 23, compound 11, compound 29 and compound 15.

In summary, the retinoid activity of a variety of tazarotene metabolites and derivatives were assessed by 5 biomarkers (Keratins 4, 10, 13, 19 and Filaggrin). The respective compounds had unique expression profiles. In ranking the compounds tested, 13 derivatives were found to be more active than tazarotene.

Example 9

Stability of Tazarotene Benzoate and Tazarotene Nicotinate in the Presence of Benzoyl Peroxide The reaction of (i) tazarotene, tazarotene benzoate, hydroxy tazarotenic acid and tazarotene nicotinate with (ii)

benzoyl peroxide (BPO) in 30% aqueous solutions was monitored at 35° C., room temperature and 5° C.

Individual solutions of each compound were prepared at approximately 0.25 mg/mL in acetonitrile:water (6:4 by volume). Reactions were initiated by mixing equal volumes of the test solution with an approximately 12 mg/mL solution of benzoyl peroxide (BPO) in acetonitrile:water (4:1 by volume). Therefore, the reaction solution contained approximately 0.125 mg/mL of the test compound and the BPO was at a 50-fold excess by weight (i.e. at the same ratio as a product containing 0.1% tazarotene and 5% BPO). Aliquots of the reaction solutions were stored at various temperatures protected from light.

Reactions were quenched by diluting 30 µL of the reaction solution to 50 mL with a diluent (acetonitrile:water in a ratio of 1:1 by volume) and storing the sample at 10° C. in the LC/MS sample tray or at 5° C. for storage. Duplicate samples were prepared at each time point (three at the start of the reaction) and the results were averaged together to generate a single value.

Samples were analyzed on a Waters Acquity UPLC with a Waters Xevo TQMS using an ESI source in the positive mode controlled by MassLynx V4.1 software. Separations were performed using an Acquity BEH C8 UPLC column (1.7 µm particle size, 2.1×50 mm) at 45° C. The mobile phase consisted of water and acetonitrile, each containing 0.1% formic acid. A flow rate of 0.4 mL/min was used.

Figure 24A:
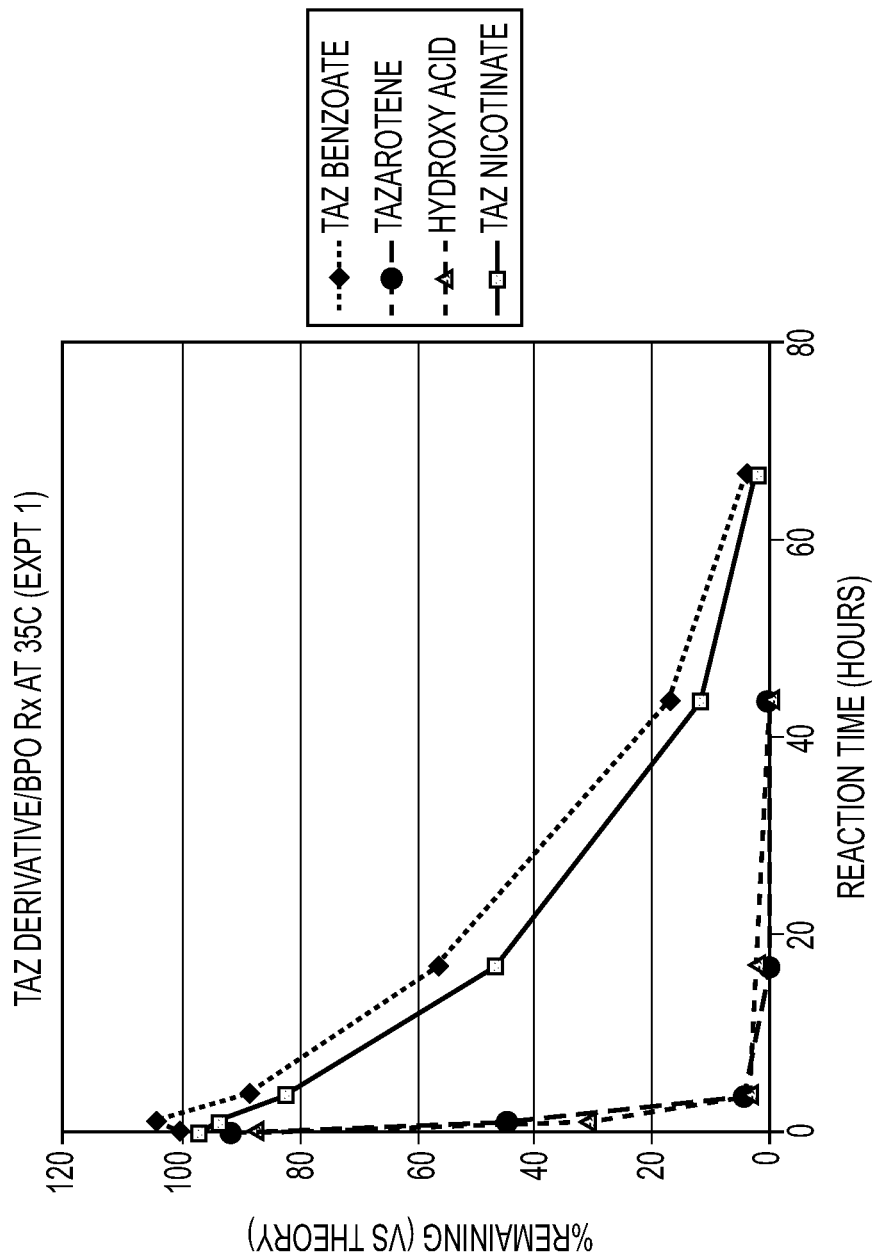
FIGS. 24A, 24B and 24C illustrate the enhanced stability of tazarotene benzoate and tazarotene nicotinate in the presence of benzoyl peroxide, relative to tazarotene and hydroxy tazarotenic acid.
Figure 24B:
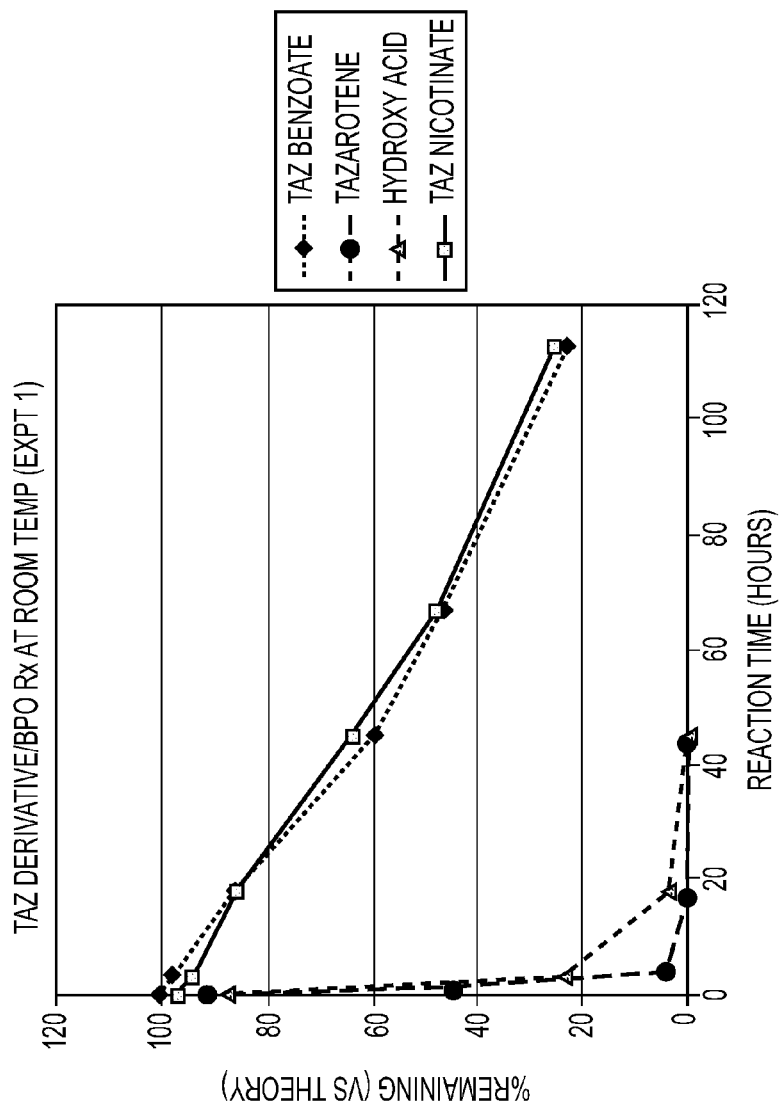
Figure 24C:
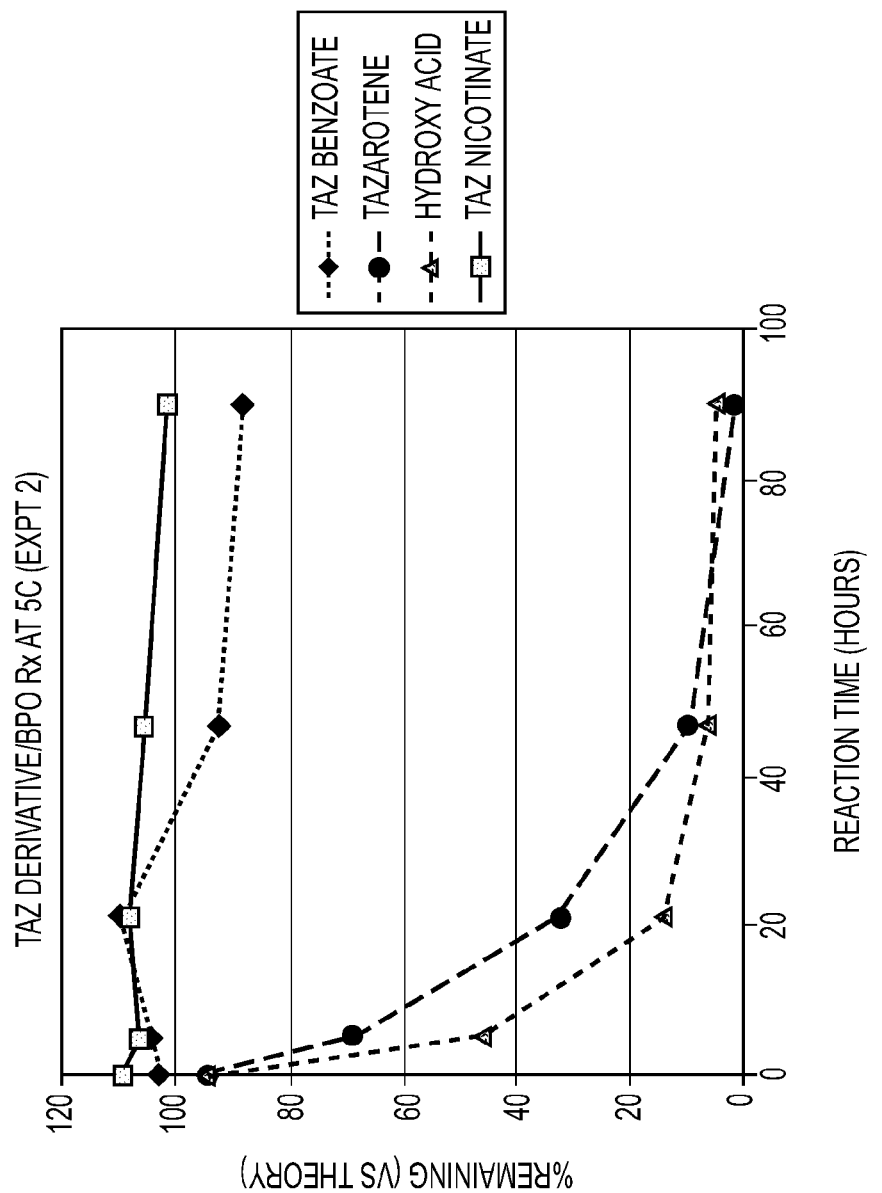

The results are set out in FIGS. 24A, 24B and 24C.

Significantly, at all three temperatures, tazarotene benzoate and tazarotene nicotinate were in the order of 25 times less reactive than tazarotene and hydroxy tazarotenic acid (with BPO). The rate of reaction of each of the test compounds with BPO was found to be a function of temperature. The rate of reaction increased roughly by a factor of 5 at room temperature compared to 5° C. and increased a further factor of approximately 3 when the reaction temperature was increased to 35° C. The reaction rates of tazarotene benzoate and tazarotene nicotinate appear to be similar at all temperatures.

Example 10

Synthesis of Tazarotene Derivatives

The invention will now be described by reference to the following examples which are merely illustrative and are not to be construed as a limitation of the scope of the present invention. All temperatures are given in degrees centigrade, all solvents are highest available purity and all reactions run under anhydrous conditions in an Ar atmosphere where necessary.

LIST OF ABBREVIATIONS

| | |
|---|---|
| DMAP: 4-(Dimethylamino)-pyridine | SPE: Solid phase extraction |
| DCM: Dichloromethane | m-CPBA: 3-Chlorobenzene-carboperoxoic acid |
| DMF: N,N-Dimethylformamide | Fmoc: Fluorenylmethyloxycarbonyl |
| dppf: 1,1'-Bis(diphenylphosphino)-ferrocene | NIS: N-Iodosuccinimide |
| DMSO: Dimethylsulfoxide | HATU: O-(7-Azabenzotriazol-1-yl)-N,N,N',N'-tetramethyluronium hexafluorophosphate |
| DIPEA: N,N-Diisopropylethyl-amine | HBTU: O-Benzotriazol-1-yl-N,N,N',N'-tetramethyluronium hexafluorophosphate |
| DSC: differential scanning calorimetry | HOBT: 1-Hydoxybenzotriazole hydrate |
| EtOAc: Ethyl acetate | IPA: isopropyl alcohol |
| EDC: 1-(3-Dimethylaminopropyl)-3-ethylcarbodiimide hydrochloride | THF: Tetrahydrofuran |
| TFA: Trifluoroacetic anhydride | mol: moles |
| TEA: Triethylamine | VCD: Vibrational Circular Dichroism analysis |
| M: molar | mmol: millimoles |
| L: liters | satd: saturated |
| mL: milliliters | eq: equivalents |
| g: grams | min: minutes |
| mg: milligrams | mp: melting point |
| h: hours | rt: room temperature |
| Aq: aqueous | NMP = 1-methyl-2-pyrrolidinone |

General Procedure for the Preparation of Acid Chlorides

Oxalyl chloride (4.0 equivalents) was added to a solution of carboxylic acid (1.0 equivalent) in dichloromethane (DCM) while stirring, along with a catalytic amount of anhydrous dimethyl formamide (DMF). The resultant solution was refluxed at 40° C. for 2 hours. The solution was cooled, the solvent removed under vacuum, the excess oxalyl chloride removed using toluene, and the resultant acid chloride was redissolved in DCM and subsequently used for ester formation.

General Procedure for the Preparation of Esters from Acid Chlorides

The acid chloride (1.6 mmol) was added to a solution of compound 14 (0.5 mmol) in DCM (5 mL) while stirring. Triethylamine (TEA) (2.7 mmol) was subsequently added and the reaction mixture was stirred overnight. The progress of the reaction was monitored by LC/MS. Upon completion of reaction, the reaction mixture was poured into water, extracted with DCM (2×5 mL aliquots). The organic extracts were combined and washed with water/brine and dried over anhydrous $Na_2SO_4$. The organic extract was concentrated and the crude ester was purified with an ISCO cartridge in a Companion system using an ethylacetate/heptanes solvent system (0-40%).

General Procedure for the Preparation of Esters from the Coupling of a Carboxylic Acid and an Alcohol (Using EDC and HOBt)

N-(3-Dimethylaminopropyl)-N'-ethylcarbodiimide hydrochloride (EDC.HCl) (2.7 mmol) and HOBt (2.7 mmol) was added to a solution of the carboxylic acid (2.7 mmol) in DCM (10 mL), while stirring. TEA (5.4 mmol) was added, followed by compound 14 (an alcohol). The reaction mixture was stirred overnight at room temperature. Upon completion of the reaction (determined by LC/MS), the mixture was poured into water (20 mL), the organic phase removed and the aqueous phase extracted with DCM (10 mL). The organic (DCM) phase was washed with brine and dried over anhydrous $Na_2SO_4$ to give the crude ester.

The molecular weight of the metabolites and analogues as determined by mass spectrometry is listed in Table 11.

Analysis of the metabolites and analogues was also conducted using $^1H$ NMR spectroscopy at 400 MHz (Varian), with the samples dissolved in deuterated chloroform or deuterated DMSO.

Compound 4

6-(2-(2-benzoyloxy-4,4-dimethylthiochroman-6-yl) ethynyl)nicotinic acid, ethyl ester (tazarotene benzoate)

Triethylamine (0.75 mL) was added to a cooled (0° C.) solution of compound 14 (0.551 g, 1.5 mmol) in DCM (15 mL) under nitrogen, followed by the addition of benzoyl chloride (0.281 g, 2.0 mmol) in DCM (3 mL). The mixture was stirred for 1 hour at room temperature and then diluted with DCM (50 mL) and then treated with saturated $NaHCO_3$ solution, followed by water (30 mL) and brine (30 mL). The organic phase was extracted, dried over anhydrous $Na_2SO4$, concentrated and purified using column chromatography (20% EtOAc/Heptanes) to obtain a colorless solid. Yield: 0.700 g (99%).

$^1$H NMR (400 MHz, CHLOROFORM-d) d 1.43 (t, J=7.08 Hz, 3H), 1.49 (s, 3H), 1.56 (s, 3H), 2.32 (br. s., 1H), 2.33 (d, J=1.66 Hz, 1H), 4.44 (q, J=7.13 Hz, 2H), 6.49 (t, J=5.52 Hz, 1H), 7.13 (d, J=8.10 Hz, 1H), 7.35 (d, J=0.88 Hz, 1H), 7.46 (t, J=7.71 Hz, 2H), 7.59 (d, J=7.91 Hz, 2H), 7.69 (s, 1H), 8.05 (d, J=7.52 Hz, 2H), 8.29 (dd, J=8.15, 1.81 Hz, 1H), 9.21 (s, 1H)

Compounds 5 and 6

(S)-6-(2-(2-benzoyloxy-4,4-dimethylthiochroman-6-yl)ethynyl) nicotinic acid, ethyl ester and (R)-6-(2-(2-benzoyloxy-4,4-dimethylthiochroman-6-yl) ethynyl)nicotinic acid, ethyl ester (enantiomers of tazarotene benzoate)

The S and R enantiomers of compound 4 (100 mg) were separated by HPLC using a chiral ADH column with a 10-50% gradient of isopropyl alcohol/water. UV absorbance was monitored at 340 nm. 33 mg and 27 mg of the respective enantiomers were obtained in >97% purity.

The stereochemistry of the enantiomers was determined using Ab Initio Vibrational Circular Dichroism (VCD) analysis.

Compound 7

6-[4,4-Dimethyl-2-(pyridine-3-carbonyloxy)thiochroman-6-ylethynyl]nicotinic acid ethyl ester (tazarotene nicotinate)

A solution of compound 14 (1.00 g, 2.72 mmol) in DCM (100 mL) was chilled in an ice water bath to 0° C., then charged with TEA (1.38 g, 1.90 mL, 13.6 mmol), and then nicotinoyl chloride hydrochloride (605 mg, 3.40 mmol) was added. The reaction was then allowed to warm to room temperature and stirred for 18 hours. The reaction was diluted with DCM (200 mL) and washed with water (2×200 mL aliquots). The aqueous washes were then pooled and back-extracted with DCM (2×100 mL). The organic fractions were then pooled, dried over $Na_2SO_4$, filtered and concentrated under reduced pressure. The crude product was chromatographed on a silica column using a heptane:EtOAc solvent system. Yield: 968 mg (75%).

$^1$H NMR (400 MHz, CHLOROFORM-d) δ ppm 1.43 (t, J=7.1 Hz, 3H), 1.49 (s, 3H), 1.56 (s, 3H), 2.33 (d, J=5.6 Hz, 2H), 4.44 (q, J=7.1 Hz, 2H), 6.51 (t, J=5.6 Hz, 1H), 7.13 (d, J=8.2 Hz, 1H), 7.37 (dd, J=8.1, 1.8 Hz, 1H), 7.41 (ddd, J=8.0, 4.9, 0.8 Hz, 1H), 7.59 (dd, J=8.2, 0.8 Hz, 1H), 7.69 (d, J=1.7 Hz, 1H), 8.22-8.36 (m, 2H) 8.81 (dd, J=4.9, 1.7 Hz, 1H), 9.22 (ddd, J=9.3, 2.1, 0.8 Hz, 2H).

Compounds 8 and 9

6-[4,4-Dimethyl-2-(pyridine-3-carbonyloxy)thiochroman-6-ylethynyl]nicotinic acid ethyl ester (tazarotene nicotinate—S and R enantiomers)

The S and R enantiomers of compound 7 were separated by supercritical fluid chromatography using an OJH column (10×250 mm at 10 ml/min) using 15% ethanol as a modifier. UV absorbance was monitored at 254 nm. The respective enantiomers were obtained in a purity of about 96%.

The stereochemistry of the enantiomers was determined using Ab Initio Vibrational Circular Dichroism (VCD) analysis.

Compound 10

6-((2-hydroxy-4,4-dimethylthiochroman-6-yl)ethynyl)nicotinic acid (hydroxytazarotenic acid)

6-(4,4-Dimethyl-1-oxo-1λ$^4$-thiochroman-6-ylethynyl)nicotinic acid ethyl ester A suspension of tazarotene (10.0 g, 28.5 mmol) in methanol (300 mL) was chilled in an ice water bath to <10° C., and then charged with the dropwise addition of a solution of $NaIO_4$ (9.13 g, 42.7 mmol) in water (100 mL) over 30 minutes. The reaction was allowed to warm to room temperature while stirring for 18 hours, and was then concentrated under reduced pressure to remove as much methanol as possible. The reaction was then diluted with DCM (500 mL) and water (150 mL). The two layers were then separated, and the aqueous layer was extracted with DCM (2×100 mL aliquots). The organic fractions were pooled, dried over $Na_2SO_4$, filtered, and concentrated under reduced pressure. The crude sulfoxide product was then chromatographed using a DCM:EtOAc solvent system. Yield: 9.00 g (86%).

$^1$H NMR (400 MHz, $CDCl_3$) δ ppm 1.34 (s, 3H), 1.43 (t, J=7.1 Hz, 3H), 1.47 (s, 3H), 1.91 (ddd, J=15.1, 8.9, 2.3 Hz, 1H), 2.45 (ddd, J=15.1, 10.3, 2.4 Hz, 1H), 3.04-3.29 (m, 2H), 4.44 (q, J=7.1 Hz, 2H), 7.58 (dd, J=8.1, 1.6 Hz, 1H), 7.63 (dd, J=8.2, 0.7 Hz, 1H), 7.71 (d, J=1.6 Hz, 1H), 7.78 (d, J=8.1 Hz, 1H), 8.32 (dd, J=8.2, 2.2 Hz, 1H), 9.22 (dd, J=2.1, 0.7 Hz, 1H). MS (ESI+) 368.0.

6-(2-Acetoxy-4,4-dimethylthiochroman-6-ylethynyl) nicotinic acid ethyl ester A solution of the above sulfoxide (9.00 g, 24.5 mmol) in acetic anhydride (185 mL) was heated to 130° C. for 5 hours, then concentrated under reduced pressure, with toluene added to aid evaporation of the acetic anhydride. The crude acetate was then chromatographed on a silica plug using a heptane:EtOAc solvent system. Yield: 8.47 g (84%).

$^1$H NMR (400 MHz, $CDCl_3$) δ ppm 1.40 (s, 3H), 1.43 (t, J=7.2 Hz, 3H), 1.46 (s, 3H), 2.10-2.22 (m, 2H), 2.11 (s, 3H), 4.43 (q, J=7.1 Hz, 2H), 6.22 (dd, J=6.9, 5.2 Hz, 1H), 7.11 (d, J=8.1 Hz, 1H), 7.34 (dd, J=8.2, 1.8 Hz, 1H), 7.58 (dd, J=8.2, 0.8 Hz, 1H), 7.64 (d, J=1.7 Hz, 1H), 8.29 (dd, J=8.2, 2.2 Hz, 1H), 9.20 (dd, J=2.2, 0.8 Hz, 1H). MS (ESI+) 410.0.

6-((2-hydroxy-4,4-dimethylthiochroman-6-yl)ethynyl)nicotinic acid

A suspension of the above acetate (3.00 g, 7.33 mmol) in ethanol (90 mL) was charged with the dropwise addition of a solution of KOH (2.47 g, 44.0 mmol) in water (15 mL).

Within 30 minutes the reaction became homogenous, and was then allowed to stir at room temperature for 18 hours. The reaction was then concentrated under reduced pressure, diluted with water (40 mL), and then treated with the dropwise addition of 1.0 N HCl (33 mL) until a pH of ~5 was reached. The resulting yellow precipitate was filtered, and the filter cake was then washed with water (40 mL) and heptane (40 mL), and then dried under vacuum at 50° C. for 18 hours. Yield: 1.95 g (78%).

$^1$H NMR (400 MHz, DMSO-d$_6$) δ ppm 1.24 (s, 3H), 1.42 (s, 3H), 1.90 (dd, J=13.5, 9.8 Hz, 1H), 2.11 (dd, J=13.5, 4.2 Hz, 1H), 5.43 (dd, J=9.8, 4.2 Hz, 1H), 7.11 (d, J=8.2 Hz, 1H), 7.32 (dd, J=8.1, 1.8 Hz, 1H), 7.62 (d, J=1.8 Hz, 1H), 7.72 (dd, J=8.1, 0.7 Hz, 1H), 8.26 (dd, J=8.1, 2.2 Hz, 1H), 9.04 (dd, J=2.2, 0.8 Hz, 1H). MS (ESI+) 340.0.

Compound 11

6-((4,4-dimethyl-2-oxothiochroman-6-yl)ethynyl) nicotinic acid (keto tazarotenic acid)

A suspension of compound 12 (1.28 g, 3.50 mmol) in ethanol (30 mL) was charged with the dropwise addition of a solution of KOH (2.47 g, 44.0 mmol) in water (15 mL), and the reaction was allowed to stir at room temperature for 18 hours. The reaction was then concentrated under reduced pressure, diluted with water (20 mL), and then treated with the dropwise addition of 1.0 N HCl until a pH of −5 was reached. The resulting yellow precipitate was filtered, and the filter cake was then washed with water (10 mL) and heptane (10 mL), and then dried under vacuum at 50° C. for 18 hours. Crude product (1.12 g) was then dissolved in DMSO and purified by reversed-phase HPLC using a methanol:water gradient with 0.1% HCO$_2$H present in both solvents. Yield: 26 mg (2.2%).

$^1$H NMR (400 MHz, DMSO-D$_6$) δ ppm 1.35 (s, 6H), 2.80 (s, 2H), 7.37 (br. d, J=7.8 Hz, 1H), 7.52 (br. d, J=7.8 Hz, 1H), 7.65-7.80 (m, 2H), 8.23 (br. d, J=7.2 Hz, 1H), 9.01 (br. s, 1H).

Compound 12 ethyl 6-((4,4-dimethyl-2-oxothiochroman-6-yl)ethynyl)nicotinate (keto tazarotene)

6-(4,4-Dimethyl-1-oxo-1λ$^4$-thiochroman-6-ylethynyl)nicotinic acid ethyl ester

A suspension of tazarotene (10.0 g, 28.5 mmol) in methanol (300 mL) was chilled in an ice water bath to <10° C., and then charged with the dropwise addition of a solution of NaIO$_4$ (9.13 g, 42.7 mmol) in water (100 mL) over 30 minutes. The reaction was allowed to warm to room temperature while stirring for 18 hours, and was then concentrated under reduced pressure to remove as much methanol as possible. The reaction was then diluted with DCM (500 mL) and water (150 mL). The two layers were then separated, and the aqueous layer was extracted with DCM (2×100 mL aliquots). The organic fractions were pooled, dried over Na$_2$SO$_4$, filtered, and concentrated under reduced pressure. The crude sulfoxide product was then chromatographed using a DCM:EtOAc solvent system. Yield: 9.00 g (86%).

$^1$H NMR (400 MHz, CDCl$_3$) δ ppm 1.34 (s, 3H), 1.43 (t, J=7.1 Hz, 3H), 1.47 (s, 3H), 1.91 (ddd, J=15.1, 8.9, 2.3 Hz, 1H), 2.45 (ddd, J=15.1, 10.3, 2.4 Hz, 1H), 3.04-3.29 (m, 2H), 4.44 (q, J=7.1 Hz, 2H), 7.58 (dd, J=8.1, 1.6 Hz, 1H), 7.63 (dd, J=8.2, 0.7 Hz, 1H), 7.71 (d, J=1.6 Hz, 1H), 7.78 (d, J=8.1 Hz, 1H), 8.32 (dd, J=8.2, 2.2 Hz, 1H), 9.22 (dd, J=2.1, 0.7 Hz, 1H). MS (ESI+) 368.0.

6-(2-Acetoxy-4,4-dimethylthiochroman-6-ylethynyl) nicotinic acid ethyl ester

A solution of the above sulfoxide (9.00 g, 24.5 mmol) in acetic anhydride (185 mL) was heated to 130° C. for 5 hours, then concentrated under reduced procedure, with toluene added to aid evaporation of the acetic anhydride. The crude acetate was then chromatographed on a silica plug using a heptane:EtOAc solvent system. Yield: 8.47 g (84%).

$^1$H NMR (400 MHz, CDCl$_3$) δ ppm 1.40 (s, 3H), 1.43 (t, J=7.2 Hz, 3H), 1.46 (s, 3H), 2.10-2.22 (m, 2H), 2.11 (s, 3H), 4.43 (q, J=7.1 Hz, 2H), 6.22 (dd, J=6.9, 5.2 Hz, 1H), 7.11 (d, J=8.1 Hz, 1H), 7.34 (dd, J=8.2, 1.8 Hz, 1H), 7.58 (dd, J=8.2, 0.8 Hz, 1H), 7.64 (d, J=1.7 Hz, 1H), 8.29 (dd, J=8.2, 2.2 Hz, 1H), 9.20 (dd, J=2.2, 0.8 Hz, 1H). MS (ESI+) 410.0.

6-(2-Hydroxy-4,4-dimethylthiochroman-6-ylethynyl) nicotinic acid ethyl ester

A solution of the above acetate (3.29 g, 8.03 mmol) in THF (50 mL) was charged with NaOEt (2.18 g, 32.1 mmol), and the reaction was heated to 75° C. for 12 hours. The reaction was then diluted with EtOAc (250 mL) and washed with water (2×100 mL aliquots). The aqueous washes were then pooled and back-extracted with EtOAc (2×100 mL aliquots). The organic fractions were pooled, dried over Na$_2$SO$_4$, filtered, and concentrated under reduced pressure to give the thiolactol. Yield: 2.31 g (78%).

$^1$H NMR (400 MHz, CDCl$_3$) δ ppm 1.31 (s, 3H), 1.43 (t, J=7.1 Hz, 3H), 1.48 (s, 3H), 1.95-2.07 (m, 1H), 2.26 (dd, J=13.5, 4.5 Hz, 1H), 2.54 (d, J=8.5 Hz, 1H), 4.43 (q, J=7.2 Hz, 2H), 5.50 (td, J=8.8, 4.5 Hz, 1H), 7.09 (d, J=8.2 Hz, 1H), 7.32 (dd, J=8.1, 1.8 Hz, 1H), 7.58 (dd, J=8.2, 0.8 Hz, 1H), 7.62 (d, J=1.7 Hz, 1H), 8.28 (dd, J=8.2, 2.2 Hz, 1H), 9.20 (dd, J=2.2, 0.8 Hz, 1H).

ethyl 6-((4,4-dimethyl-2-oxothiochroman-6-yl)ethynyl)nicotinate

A solution of the above thiolactol (2.31 g, 6.29 mmol) in DCM (500 mL) was charged with Dess-Martin periodinane (2.80 g, 6.60 mmol), and the reaction stirred at room temperature for 1 hour. The reaction was then concentrated under reduced pressure, then diluted with EtOAc (250 mL) and washed with a saturated aqueous NaHCO$_3$ solution (2×100 mL aliquots). The aqueous washes were then pooled and back-extracted with EtOAc (2×200 mL). The organic fractions were then pooled, dried over Na$_2$SO$_4$, filtered, and concentrated under reduced pressure. The crude product was then chromatographed on a silica plug using a heptane:EtOAc solvent system. Yield: 1.28 g (56%).

$^1$H NMR (400 MHz, CDCl$_3$) δ ppm 1.44 (t, J=7.2 Hz, 3H), 1.44 (s, 6H), 2.71 (s, 2H), 4.44 (q, J=7.1 Hz, 2H), 7.23 (d, J=8.1 Hz, 1H), 7.48 (dd, J=8.1, 1.7 Hz, 1H), 7.62 (dd, J=8.1, 0.8 Hz, 1H), 7.73 (d, J=1.7 Hz, 1H), 8.31 (dd, J=8.2, 2.2 Hz, 1H), 9.22 (dd, J=2.2, 0.8 Hz, 1H).

Compound 13

Ethyl 6-[2-palmitoyl-4,4-dimethyl-3,4-dihydro-2-thiochromen-6-yl) ethynyl]pyridine-3-carboxylate Ethyl 6-[2-hydroxy-4,4-dimethyl-3,4-dihydro-2-thiochromen-6-yl)ethynyl]pyridine-3-carboxylate (hydroxy tazarotene) was reacted with palmitoyl chloride in DCM and TEA at room temperature. The crude product was purified by column chromatography to give the desired compound.

$^1$H NMR (400 MHz, CHLOROFORM-d) δ 0.85 (d, J=13.57 Hz, 2H), 0.85 (s, 2H), 1.22 (s, 26H), 1.29 (br. s, 6H), 1.35-1.50 (m, 11H), 1.56 (s, 2H), 1.63 (br. s, 1H), 1.60 (d, J=7.42 Hz, 2H), 2.03-2.20 (m, 2H), 2.31 (d, J=15.03 Hz, 1H), 2.31 (s, 1H), 4.40 (q, J=7.13 Hz, 2H), 6.19 (dd, J=6.49, 5.32 Hz, 1H) 7.07 (d, J=8.10 Hz, 1H), 7.31 (dd, J=8.15, 1.61 Hz, 1H), 7.55 (d, J=8.10 Hz, 1H), 7.61 (d, J=1.56 Hz, 1H), 8.25 (dd, J=8.15, 2.10 Hz, 1H), 9.17 (d, J=1.56 Hz, 1H)

Compound 14

Ethyl 6-[(2-hydroxy-4,4-dimethyl-3,4-dihydro-2-thiochromen-6-yl)ethynyl]pyridine-3-carboxylate (hydroxy tazarotene)

Hydrolysis of compound 17 with sodium ethoxide in refluxing THF gave a mixture of the title compound, along with compound 10. The title compound was obtained (51%) by column chromatographic purification to remove the non-polar impurities and compound 10 (the hydroxy acid).

$^1$H NMR (400 MHz, CHLOROFORM-d) δ 1.25 (s, 3H), 1.38 (t, J=7.13 Hz, 3H), 1.42 (s, 3H), 1.98 (dd, J=13.42, 9.32 Hz, 1H), 2.21 (dd, J=13.47, 4.49 Hz, 1H), 3.21 (d, J=8.10 Hz, 1H), 4.39 (q, J=7.13 Hz, 2H), 5.48 (dt, J=13.03, 4.47 Hz, 1H), 7.02 (d, J=8.10 Hz, 1H), 7.26 (dd, J=8.10, 1.56 Hz, 1H), 7.53 (d, J=8.20 Hz, 1H), 7.57 (d, J=1.46 Hz, 1H), 8.24 (dd, J=8.15, 2.10 Hz, 1H), 9.15 (d, J=1.56 Hz, 1H)

Compound 15

6-[2-(2-Hydroxy-acetoxy)-4,4-dimethyl-thiochroman-6-ylethynyl]-nicotinic acid ethyl ester Glycolic acid (4.2 g, 0.05 mole) and tert-butyldimethylchlorosilane (17.7 g, 0.012 mole) were stirred in 40 mL of dry DMF. Imidazole (15.62 g, 0.23 mol) was added to the mixture and stirred under nitrogen for 18 hours. The mixture was poured into deionized water (approximately 250 mL) and extracted with diethyl ether (3×100 mL aliquots). The organic fractions were combined, washed with saturated NaHCO$_3$, dried over MgSO4, and concentrated in vacuo to give an oil. Further drying under high vacuum provided 10.7 g (91%) of the bis-silylated glycolic acid as a white solid.

The bis-silylated glycolic acid was dissolved in 125 mL of dry DCM containing several drops of DMF. A solution of 13.4 mL oxalyl chloride (148 mmoles, 4.5 equivalents) was added drop wise under nitrogen for 20 minutes. The mixture was stirred for 4 hours at ambient temperature, then concentrated under vacuum to remove the volatiles (unreacted oxalyl chloride) to give the crude acid chloride (tert-butyldimethyl-silyloxy glycolic acid chloride) as a yellow oil.

A solution of Ethyl 6-[(2-hydroxy-4,4-dimethyl-3,4-dihydro-2-thiochromen-6-yl)ethynyl]pyridine-3-carboxylate (hydroxy tazarotene) (400 mg, 1 mmole)) in DCM/TEA at room temperature was prepared. The mixture was placed under a nitrogen atmosphere and the above acid chloride (340 mg, 1.5 mmoles, 1.5 equivalents) was added slowly at room temperature. The mixture was stirred at ambient temperature for 17 hours after which time, LCMS analysis showed complete conversion. The mixture was diluted with DCM (50 mL) and washed with H$_2$O (15 mL) followed by saturated NaHCO$_3$ (15 mL) and brine solution. The organic layer was dried over Na$_2$SO$_4$, filtered and concentrated to an oil—a silylated intermediate. Chromatography on silica gel eluting with an ethyl acetate-heptanes gradient gave 300 mg of purified product.

The silylated intermediate was dissolved in THF (4 mL) and acetic acid (0.5 mL). The stirring mixture was treated with 1M TBAF (1 mL, 1 mmole) and stirred for 1 hour at ambient temperature. The crude reaction mixture was concentrated to an oil. The oil was treated with heptanes (5 mL) and kept cold (~4° C.) overnight. The resulting solid was filtered and washed with heptanes to give 130 mg (29%) of compound 15 as a white translucent solid.

$^1$H NMR (400 MHz, CHLOROFORM-d) δ 1.36-1.51 (m, 11H), 2.10-2.29 (m, 2H), 2.35 (t, J=5.66 Hz, 1H), 4.21 (d, J=5.66 Hz, 2H), 4.37-4.50 (m, 2H), 6.36 (dd, J=6.59, 5.32 Hz, 1H), 7.11 (d, J=8.10 Hz, 1H), 7.36 (dd, J=8.10, 1.56 Hz, 1H), 7.59 (d, J=8.20 Hz, 1H), 7.65 (d, J=1.46 Hz, 1H), 8.29 (dd, J=8.15, 2.10 Hz, 1H), 9.21 (d, J=1.46 Hz, 1H)

Compound 16

Ethyl 6-[(2-(2-methoxyacetyl)-4,4-dimethyl-3,4-dihydro-2-thiochromen-6-yl)ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with methoxyacetyl chloride in DCM/TEA at room temperature. The crude product was purified by column chromatography to give the desired compound.

$^1$H NMR (400 MHz, CHLOROFORM-d) δ 1.43 (d, J=14.45 Hz, 7H), 1.43 (s, 2H), 2.09-2.34 (m, 2H), 3.46 (s, 3H), 4.07 (s, 2H), 4.43 (q, J=7.19 Hz, 2H), 6.33 (dd, J=6.64, 5.27 Hz, 1H), 7.11 (d, J=8.20 Hz, 1H), 7.35 (dd, J=8.15, 1.61 Hz, 1H), 7.58 (d, J=8.10 Hz, 1H), 7.64 (d, J=1.46 Hz, 1H), 8.28 (dd, J=8.15, 2.10 Hz, 1H), 9.20 (d, J=1.46 Hz, 1H)

Compound 17

Ethyl 6-[(2-acetyl-4,4-dimethyl-3,4-dihydro-2-thiochromen-6-yl) ethynyl]pyridine-3-carboxylate Tazarotene was oxidized with sodium periodate in methanol/water to give the corresponding sulfoxide. After column purification it yielded 47 g (90%) of the sulfoxide, which was subjected to Pummerer rearrangement with acetic anhydride as the solvent and acylating agent to yield the desired product (42 g).

$^1$H NMR (400 MHz, CHLOROFORM-d) δ 1.39 (s, 4H), 1.41 (s, 2H) 1.43-1.49 (m, 4H), 2.10 (s, 3H), 2.11-2.18 (m, 2H), 4.42 (q, J=7.13 Hz, 2H), 6.20 (dd, J=6.69, 5.42 Hz, 1H), 7.09 (d, J=8.10 Hz, 1H), 7.33 (dd, J=8.10, 1.37 Hz, 1H), 7.57 (d, J=8.10 Hz, 1H), 7.63 (d, J=1.27 Hz, 1H), 8.27 (dd, J=8.15, 2.00 Hz, 1H), 9.19 (d, J=1.37 Hz, 1H)

Compound 18

Ethyl 6-[(2-n-butyryloxyl-4,4-dimethyl-3,4-dihydro-2-thiochromen-6-yl)ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with butyryl chloride in DCM/TEA at room temperature. The crude product was purified by column chromatography to give the desired compound.

$^1$H NMR (400 MHz, CHLOROFORM-d) δ 0.97 (t, J=7.42 Hz, 4H), 1.38-1.50 (m, 11H), 1.63-1.74 (m, 3H), 2.15 (d, J=6.83 Hz, 1H), 2.17 (d, J=5.27 Hz, 1H), 2.33 (d, J=15.13 Hz,

1H), 2.34 (s, 1H), 4.43 (q, J=7.13 Hz, 2H), 6.23 (dd, J=6.49, 5.42 Hz, 1H), 7.11 (d, J=8.10 Hz, 1H), 7.34 (dd, J=8.10, 1.56 Hz, 1H), 7.58 (d, J=8.10 Hz, 1H), 7.64 (d, J=1.37 Hz, 1H), 8.29 (dd, J=8.15, 2.10 Hz, 1H), 9.21 (d, J=1.56 Hz, 1H)

Compound 19

Ethyl 6-[(2-lauroyl-4,4-dimethyl-3,4-dihydro-2-thiochromen-6-yl) ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with lauroyl chloride in DCM/TEA at room temperature. The crude product was purified by column chromatography to give the desired compound.
$^1$H NMR (400 MHz, CHLOROFORM-d) δ 0.88 (d, J=13.71 Hz, 2H), 0.88 (s, 2H), 1.20-1.38 (m, 4H), 1.26 (s, 18H), 1.41 (s, 4H), 1.43 (s, 2H), 1.44-1.49 (m, 4H), 1.57-1.73 (m, 4H), 2.14 (d, J=6.74 Hz, 1H), 2.17 (d, J=5.22 Hz, 1H), 2.31-2.39 (m, 2H), 4.43 (q, J=7.11 Hz, 2H), 6.22 (dd, J=6.64, 5.22 Hz, 1H), 7.10 (d, J=8.15 Hz, 1H), 7.34 (dd, J=8.13, 1.73 Hz, 1H), 7.58 (dd, J=8.15, 0.83 Hz, 1H), 7.64 (d, J=1.71 Hz, 1H), 8.28 (dd, J=8.15, 2.15 Hz, 1H), 9.20 (dd, J=2.15, 0.78 Hz, 1H)

Compound 20

Ethyl 6-[(2-isobutyryloxy-4,4-dimethyl-3,4-dihydro-2-thiochromen-6-yl)ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with isobutyryl chloride in DCM/TEA at room temperature. The crude product was purified by column chromatography to give the desired compound.
$^1$H NMR (400 MHz, CHLOROFORM-d) δ 0.74-0.98 (m, 4H), 1.20 (d, J=7.03 Hz, 7H), 1.44 (d, J=14.15 Hz, 6H), 1.43 (t, J=7.13 Hz, 5H), 2.17 (d, J=4.39 Hz, 2H), 2.15 (s, 1H) 2.49-2.66 (m, 1H), 4.44 (q, J=7.13 Hz, 2H) 6.16-6.26 (m, 1H), 7.11 (d, J=8.10 Hz, 1H), 7.34 (dd, J=8.10, 1.46 Hz, 1H), 7.59 (d, J=8.20 Hz, 1H), 7.65 (d, J=1.37 Hz, 1H), 8.29 (dd, J=8.10, 2.05 Hz, 1H), 9.21 (d, J=1.46 Hz, 1H)

Compound 21

Ethyl 6-[(2-linoeoyll-4,4-dimethyl-3,4-dihydro-2-thiochromen-6-yl) ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with linoleoyl chloride in DCM/TEA at room temperature. The crude product was purified by column chromatography to give the desired compound.
$^1$H NMR (400 MHz, CHLOROFORM-d) δ 0.76-0.97 (m, 9H), 1.19-1.39 (m, 26H), 1.40-1.50 (m, 15H), 1.67 (br. s, 1H), 1.64 (d, J=7.32 Hz, 2H), 2.03 (br. s, 1H), 2.05 (d, J=6.74 Hz, 5H), 2.15 (d, J=6.83 Hz, 2H), 2.17 (d, J=5.27 Hz, 1H), 2.35 (d, J=14.93 Hz, 2H), 2.35 (s, 1H), 2.78 (d, J=12.49 Hz, 1H), 2.78 (s, 1H), 4.44 (q, J=7.13 Hz, 3H), 5.27-5.45 (m, 6H), 6.23 (dd, J=6.54, 5.37 Hz, 1H), 7.11 (d, J=8.10 Hz, 1H) 7.34 (dd, J=8.10, 1.56 Hz, 1H), 7.59 (d, J=8.20 Hz, 1H), 7.64 (d, J=1.46 Hz, 1H), 8.29 (dd, J=8.15, 2.10 Hz, 1H)

Compound 22

Ethyl 6-[(2-linleolyl-4,4-dimethyl-3,4-dihydro-2-thiochromen-6-yl) ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with linolenoyl chloride in DCM/TEA at room temperature. The crude product was purified by column chromatography to give the desired compound.
$^1$H NMR (400 MHz, CHLOROFORM-d) δ 0.98 (t, J=7.52 Hz, 4H), 1.22-1.38 (m, 14H), 1.38-1.50 (m, 13H), 1.66 (br. s, 1H), 1.64 (d, J=7.22 Hz, 2H), 2.01-2.22 (m, 9H), 2.35 (t, J=7.52 Hz, 3H), 2.69-2.93 (m, 6H), 4.44 (q, J=7.13 Hz, 3H), 5.28-5.45 (m, 9H), 6.23 (dd, J=6.54, 5.37 Hz, 1H), 7.11 (d, J=8.10 Hz, 1H), 7.34 (dd, J=8.10, 1.56 Hz, 1H), 7.59 (d, J=8.20 Hz, 1H), 7.64 (d, J=1.56 Hz, 1H), 8.29 (dd, J=8.15, 2.10 Hz, 1H)

Compound 23

Ethyl 6-[(2-(N-methyl-4-piperidinylcarboxy-4,4-dimethyl-3,4-dihydro-2-thiochromen-6-yl)ethynyl] pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with 1-methyl piperidine carbonyl chloride in DCM/TEA at room temperature. The crude product was purified by column chromatography to give the desired compound.
$^1$H NMR (400 MHz, CHLOROFORM-d) δ 1.35-1.50 (m, 11H), 1.70-1.85 (m, 1H), 1.78 (dd, J=11.23, 1.46 Hz, 2H), 1.85-2.06 (m, 5H), 2.14 (d, J=11.81 Hz, 1H), 2.14 (s, 1H), 2.21-2.36 (m, 1H), 2.25 (s, 4H), 2.79 (d, J=11.23 Hz, 2H), 4.42 (q, J=7.13 Hz, 2H), 6.15-6.26 (m, 1H), 7.09 (d, J=8.10 Hz, 1H), 7.33 (dd, J=8.10, 1.56 Hz, 1H), 7.57 (d, J=8.20 Hz, 1H), 7.63 (d, J=1.37 Hz, 1H), 8.27 (dd, J=8.15, 2.10 Hz, 1H), 9.19 (d, J=1.46 Hz, 1H)

Compound 24

Ethyl 6-[(2-propionyl-4,4-dimethyl-3,4-dihydro-2-thiochromen-6-yl) ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with propionyl chloride in DCM with TEA as a base at room temperature. The crude product was purified by column chromatography to give the desired compound.
$^1$H NMR (400 MHz, CHLOROFORM-d) δ 1.17 (t, J=7.56 Hz, 4H), 1.34-1.51 (m, 11H), 2.15 (d, J=6.74 Hz, 1H), 2.17 (d, J=5.27 Hz, 1H), 2.38 (q, J=7.58 Hz, 2H), 4.43 (q, J=7.13 Hz, 2H), 6.23 (dd, J=6.59, 5.32 Hz, 1H), 7.11 (d, J=8.10 Hz, 1H), 7.34 (dd, J=8.10, 1.56 Hz, 1H), 7.59 (d, J=8.10 Hz, 1H), 7.64 (d, J=1.46 Hz, 1H), 8.29 (dd, J=8.20, 2.15 Hz, 1H), 9.21 (d, J=1.56 Hz, 1H)

Compound 25

Ethyl 6-[(2-salicylicyl-4,4-dimethyl-3,4-dihydro-2-thiochromen-6-yl) ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with salicylic acid using EDC and HOBt. The reaction afforded the desired compound, along with a self coupled impurity. The desired product was obtained via column chromatography.
$^1$H NMR (400 MHz, CHLOROFORM-d) δ 1.40 (t, J=7.13 Hz, 7H), 1.47 (s, 7H), 1.52 (s, 8H), 2.29 (d, J=1.56 Hz, 2H), 2.31 (d, J=2.44 Hz, 2H), 4.41 (q, J=7.06 Hz, 4H), 6.47 (t, J=5.51 Hz, 2H), 6.79-6.92 (m, 2H), 6.98 (d, J=8.30 Hz, 2H), 7.10 (d, J=8.10 Hz, 2H), 7.34 (dd, J=8.10, 1.37 Hz, 2H), 7.46 (s, 2H), 7.57 (d, J=8.10 Hz, 2H), 7.66 (d, J=1.17 Hz, 2H), 7.76 (dd, J=7.96, 1.32 Hz, 2H), 8.26 (dd, J=8.10, 2.05 Hz, 2H), 9.18 (d, J=1.37 Hz, 2H), 10.53 (s, 1H)

Compound 26

Ethyl 6-[(2-(4-tetrahydropyranyloxy-4,4-dimethyl-3,4-dihydro-2-thiochromen-6-yl)ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with tetrahydropyran-4-carbonyl chloride in DCM/TEA at room temperature. The crude product was purified by column chromatography to give the desired compound.

$^1$H NMR (400 MHz, CHLOROFORM-d) δ 1.31-1.50 (m, 11H), 1.69-1.92 (m, 5H), 2.04-2.26 (m, 2H), 2.55 (t, J=10.54 Hz, 1H), 3.32-3.48 (m, 2H), 3.94 (dd, J=11.47, 2.88 Hz, 2H), 4.41 (q, J=7.13 Hz, 2H), 6.14-6.28 (m, 1H), 7.08 (d, J=8.10 Hz, 1H), 7.32 (dd, J=8.10, 1.46 Hz, 1H), 7.56 (d, J=8.10 Hz, 1H), 7.62 (d, J=1.27 Hz, 1H), 8.26 (dd, J=8.20, 2.05 Hz, 1H), 9.18 (d, J=1.37 Hz, 1H)

Compound 27

Ethyl 6-[(2-monomethyladopyl-4,4-dimethyl-3,4-dihydro-2-thiochromen-6-yl)ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with monomethyl adipoyl chloride in DCM/TEA at room temperature. The crude product was purified by column chromatography to give the desired compound.

$^1$H NMR (400 MHz, CHLOROFORM-d) δ 1.40 (d, J=16.40 Hz, 8H), 1.40 (s, 3H), 1.66 (d, J=14.06 Hz, 1H), 1.66 (t, J=3.42 Hz, 3H), 2.05-2.21 (m, 2H), 2.25-2.42 (m, 4H), 3.64 (s, 3H), 4.40 (q, J=7.13 Hz, 2H), 6.19 (dd, J=6.59, 5.32 Hz, 1H), 7.07 (d, J=8.10 Hz, 1H), 7.31 (dd, J=8.10, 1.56 Hz, 1H), 7.55 (d, J=8.20 Hz, 1H), 7.61 (d, J=1.46 Hz, 1H), 8.26 (dd, J=8.10, 2.15 Hz, 1H), 9.17 (d, J=1.46 Hz, 1H)

Compound 28

Ethyl 6-[(2-(3-monomethylazelauate-4,4-dimethyl-3,4-dihydro-2-thiochromen-6-yl)ethynyl]pyridine-3-carboxylate Ethyl 6-[(2-hydroxy-4,4-dimethyl-3,4-dihydro-2-thiochromen-6-yl)ethynyl]pyridine-3-carboxylate (hydroxy tazarotene) was reacted with monomethyl azelate chloride in DCM/TEA at room temperature. The crude product was purified by column chromatography to give the desired compound.

$^1$H NMR (400 MHz, CHLOROFORM-d) δ 1.32 (br. s., 11H), 1.39-1.50 (m, 11H), 1.53-1.73 (m, 7H), 2.15 (d, J=6.74 Hz, 2H), 2.17 (d, J=5.17 Hz, 1H), 2.26-2.46 (m, 7H), 3.58-3.77 (m, 5H), 4.44 (q, J=7.13 Hz, 2H), 6.22 (dd, J=6.54, 5.37 Hz, 1H), 7.11 (d, J=8.20 Hz, 1H), 7.34 (dd, J=8.10, 1.56 Hz, 1H), 7.59 (d, J=8.20 Hz, 1H), 7.64 (d, J=1.46 Hz, 1H), 8.29 (dd, J=8.15, 2.10 Hz, 1H), 9.21 (d, J=1.46 Hz, 1H)

Compound 29

6-[2-((S)-2-Amino-3-methyl-butyryloxy)-4,4-dimethyl-thiochroman-6-ylethynyl]-nicotinic acid ethyl ester Ethyl 6-[(2-hydroxy-4,4-dimethyl-3,4-dihydro-2-thiochromen-6-yl)ethynyl]pyridine-3-carboxylate (hydroxy tazarotene) was reacted with Fmoc protected amino acid chloride (from Valine) to give the Fmoc protected amino ester. Fmoc deprotection was facilitated with dilute piperidine in THF at room temperature, as follows:

20% Piperidine (5 equivalents) in THF was added to a solution of the Fmoc-protected amino ester in THF, while stirring. The reaction mixture was stirred for 5 hours and progress of the reaction was periodically monitored by LC/MS. At completion of the reaction, the reaction mixture was poured into water and extracted with EtOAc (2×20 mL aliquots). The organic layers were combined, washed with brine, dried over anhydrous Na$_2$SO$_4$, concentrated and purified in a Companion purification system using a 12.0 g cartridge.

$^1$H NMR (400 MHz, CHLOROFORM-d) δ 0.92 (t, J=6.78 Hz, 3H), 0.99 (d, J=6.74 Hz, 3H), 1.35-1.59 (m, 12H), 1.97-2.09 (m, 1H), 2.09-2.26 (m, 2H), 3.31 (d, J=5.17 Hz, 1H), 4.43 (q, J=7.06 Hz, 2H), 6.20-6.34 (m, 1H), 7.10 (d, J=8.10 Hz, 1H), 7.34 (d, J=8.10 Hz, 1H), 7.58 (d, J=8.20 Hz, 1H), 7.64 (d, J=1.27 Hz, 1H), 8.28 (dd, J=8.10, 2.05 Hz, 1H), 9.20 (d, J=1.56 Hz, 1H)

TABLE 11

| | Description | Structure | Notes |
|---|---|---|---|
| 1 | Untreated (negative) control | NA | None |
| 2 | OD (vehicle) control | NA | None |
| 3 | Tazarotene (0.1% in OD) | 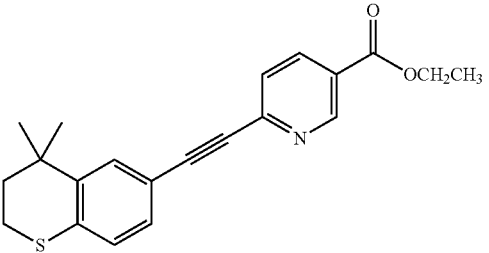 | MW 351.46 Purity 99.5% |

TABLE 11-continued

| Description | Structure | Notes |
|---|---|---|
| 4 Tazarotene benzoate 6-(2-(2-benzoyloxy-4,4-dimethylthiochroman-6-yl)ethynyl)nicotinic acid, ethyl ester | 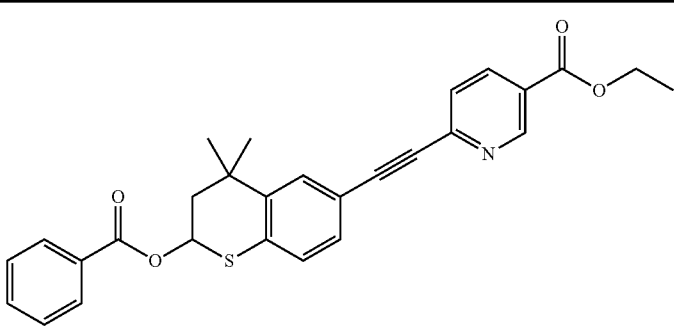 | MW 471.58 Purity 98.0% |
| 5 Tazarotene benzoate (S isomer) (S)-6-(2-(2-benzoyloxy-4,4-dimethylthiochroman-6-yl)ethynyl)nicotinic acid, ethyl ester | 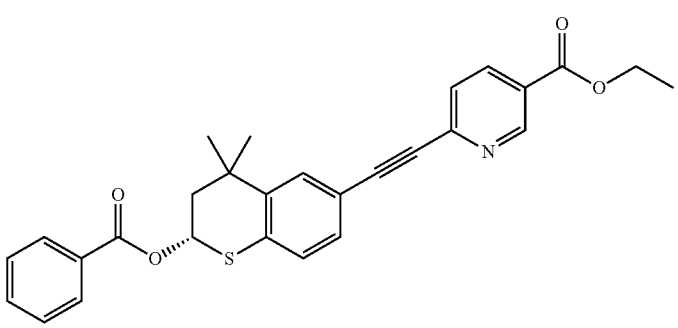 [SMILES: CCOC(=O)c1ccc(C#Cc2ccc3c(c2)C(C)(C)C[C@@H](OC(=O)c2ccccc2)S3)nc1] | MW 471.58 Purity >97.0% |
| 6 Tazarotene benzoate (R isomer) (R)-6-(2-(2-benzoyloxy-4,4-dimethylthiochroman-6-yl)ethynyl)nicotinic acid, ethyl ester | 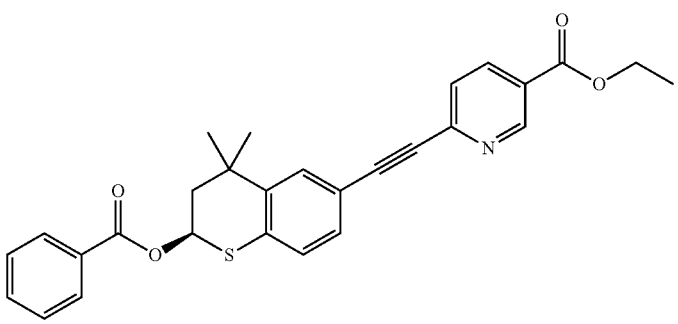 [SMILES: CCOC(=O)c1ccc(C#Cc2ccc3c(c2)C(C)(C)C[C@H](OC(=O)c2ccccc2)S3)nc1] | MW 471.58 Purity >97.0% |
| 7 Tazarotene nicotinate 6-[4,4-Dimethyl-2-(pyridine-3-carbonyloxy)thiochroman-6-ylethynyl]nicotinic acid ethyl ester | 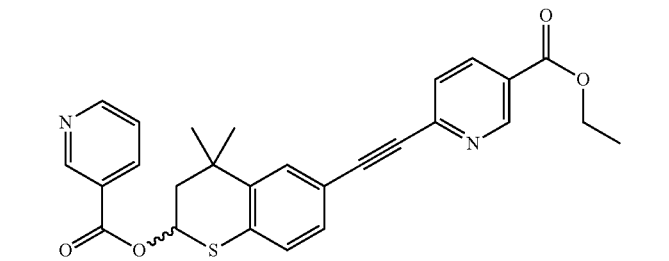 [SMILES: CCOC(=O)c1ccc(C#Cc2ccc3c(c2)C(C)(C)CC(OC(=O)c2cccnc2)S3)nc1] | MW 472.57 Purity 94.0% |
| 8 Tazarotene nicotinate (S isomer) S-6-[4,4-Dimethyl-2-(pyridine-3-carbonyloxy)thiochroman-6-ylethynyl]nicotinic acid ethyl ester | 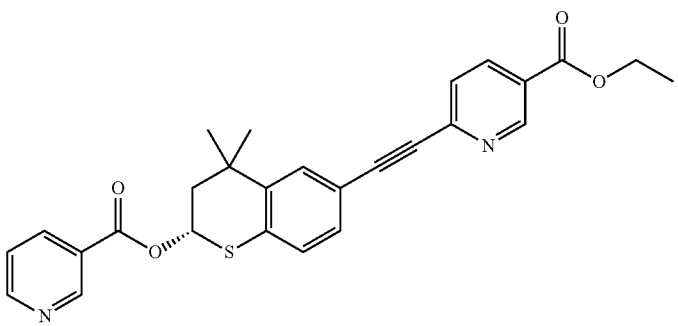 [SMILES: CCOC(=O)c1ccc(C#Cc2ccc3c(c2)C(C)(C)C[C@@H](OC(=O)c2cccnc2)S3)nc1] | MW 472.56 Purity 95.0% |

TABLE 11-continued

| Description | Structure | Notes |
|---|---|---|
| 9 Tazarotene nicotinate (R isomer) R-6-[4,4-Dimethyl-2-(pyridine-3-carbonyloxy)thiochroman-6-ylethynyl]nicotinic acid ethyl ester | 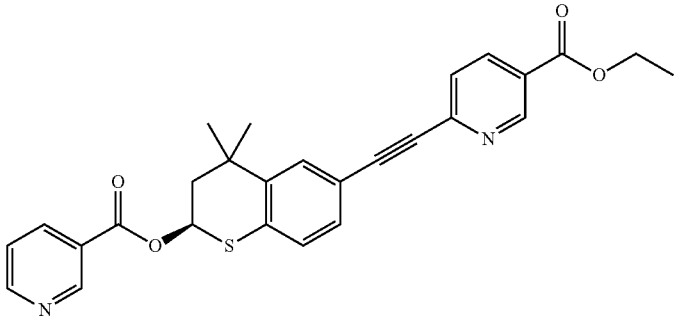 [SMILES: CCOC(=O)c1ccc(C#Cc2ccc3c(c2)C(C)(C)C[C@H](OC(=O)c2cccnc2)S3)nc1] | MW 472.56 Purity 95.0% |
| 10 Hydroxy tazarotenic acid 6-((2-hydroxy-4,4-dimethythiochroman-6-yl)ethynyl)nicotinic acid | 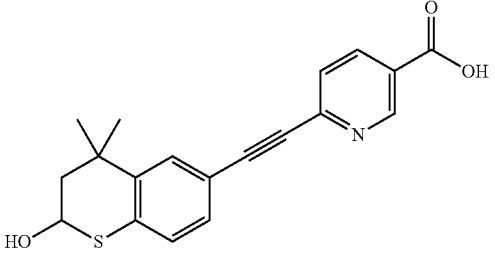 [SMILES: CC1(C)CC(O)Sc2ccc(C#Cc3ccc(C(=O)O)cn3)cc21] | MW 339.42 Purity 99.3% |
| 11 Keto tazarotenic acid 6-((4,4-dimethyl-2-oxothiochroman-6-yl)ethynyl)nicotinic acid | 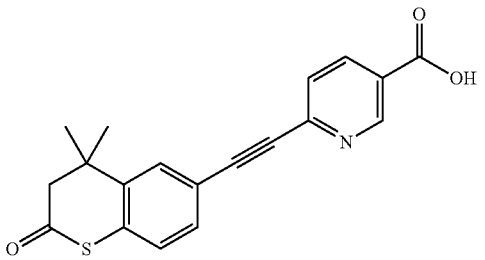 [SMILES: CC1(C)CC(=O)Sc2ccc(C#Cc3ccc(C(=O)O)cn3)cc21] | MW 337.40 Purity 87.0% |
| 12 Keto tazarotene Ethyl 6-((4,4-dimethyl-2-oxothiochroman-6-yl)ethynyl)nicotinate | 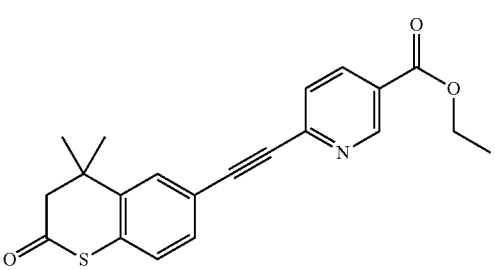 [SMILES: CCOC(=O)c1ccc(C#Cc2ccc3c(c2)C(C)(C)CC(=O)S3)nc1] | MW 406.00 Purity 99.0% |
| 13 Ethyl 6-[2-palmitoyl-4,4-dimethyl-3,4-dihydro-2-thiochromen-6-yl)ethynyl]pyridine-3-carboxylate | 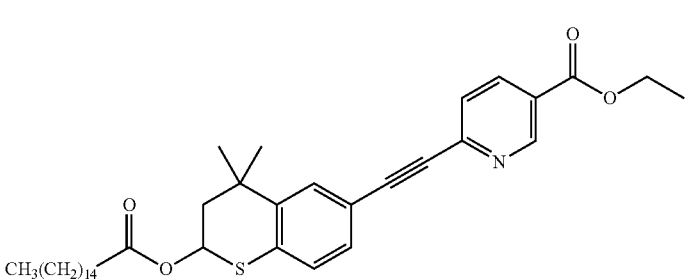 | MW 605.89 Purity 94.8% |

TABLE 11-continued

| Description | Structure | Notes |
|---|---|---|
| 14 Hydroxy Tazarotene Ethyl 6-[(2-hydroxy-4,4-dimethyl-3,4-dihydro-2-thiochromen-6-yl)ethyynyl]pyridine-3-carboxylate | | MW 367.47 Purity 98.4% |
| 15 6-[2-(2-Hydroxy-acetoxy)-4,4-dimethyl-thiochroman-6-ylethynyl]-nicotinic acid ethyl ester | | MW 425.50 Purity >99.5% |
| 16 Ethyl 6-[(2-(2-methoxyacetyl)-4,4-dimethyl-3,4-dihydro-2-thiochromen-6-yl)ethynyl]pyridine-3-carboxylate | | MW 439.53 Purity 96.3% |
| 17 Ethyl 6-[(2-acetyl-4,4-dimethyl-3,4-dihydro-2-thiochromen-6-yl)ethynyl]pyridine-3-carboxylate | | MW 409.51 Purity 95.4% |
| 18 Ethyl 6-[(2-n-butyryloxyl-4,4-dimethyl-3,4-dihydro-2-thiochromen-6-yl)ethynyl]pyridine-3-carboxylate | | MW 437.56 Purity 98.4% |

TABLE 11-continued

| | Description | Structure | Notes |
|---|---|---|---|
| 19 | Ethyl 6-[(2-lauroyl-4,4-dimethyl-3,4-dihydro-2-thiochrornen-6-yl)ethynyl]pyridine-3-carboxylate | 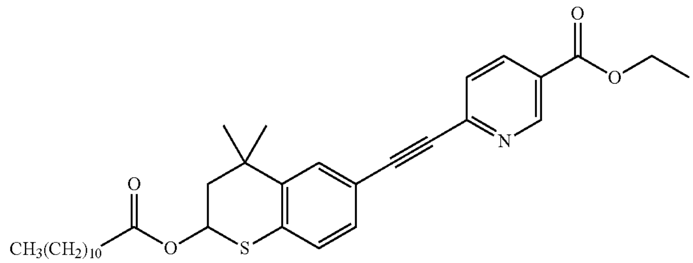 | MW 549.78 Purity 98.5% |
| 20 | Ethyl 6-[(2-isobutyryloxy-4,4-dimethyl-3,4-dihydro-2-thiochrornen-6-yl)ethynyl]pyridine-3-carboxylate | 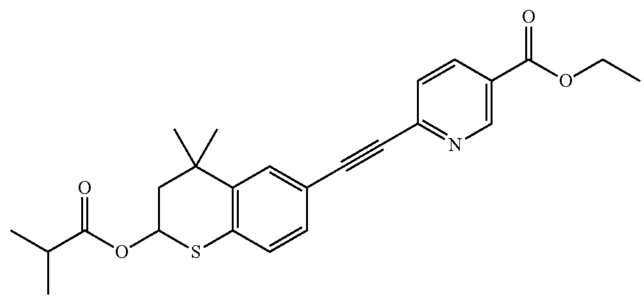 [SMILES: CCOC(=O)c1ccc(C#Cc2ccc3c(c2)C(C)(C)CC(OC(=O)C(C)C)S3)nc1] | MW 437.56 Purity 98.4% |
| 21 | Ethyl 6-[(2-linoeoyll-4,4-dimethyl-3,4-dihydro-2-thiochrornen-6-yl)ethynyl]pyridine-3-carboxylate | 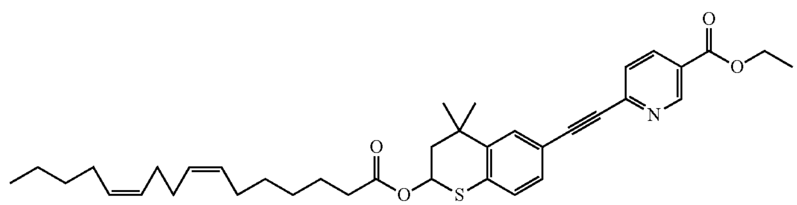 [SMILES: CCCC/C=C\CC/C=C\CCCCCC(=O)OC1CC(C)(C)c2cc(C#Cc3ccc(C(=O)OCC)cn3)ccc2S1] | MW 629.91 Purity 98.3% |
| 22 | Ethyl 6-[(2-linleolyl-4,4-dimethyl-3,4-dihydro-2-thiochrornen-6-yl)ethynyl]pyridine-3-carboxylate | 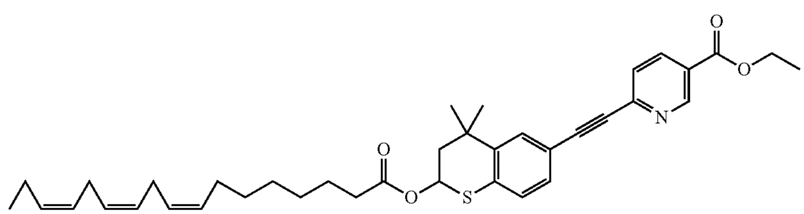 [SMILES: CC/C=C\C/C=C\C/C=C\CCCCCCC(=O)OC1CC(C)(C)c2cc(C#Cc3ccc(C(=O)OCC)cn3)ccc2S1] | MW 627.89 Purity 96.1% |
| 23 | Ethyl 6-[(2-(N-methyl-4-piperidinylcarboxy-4,4-dimethyl-3,4-dihydro-2-thiochrornen-6-yl)ethynyl]pyridine-3-carboxylate | 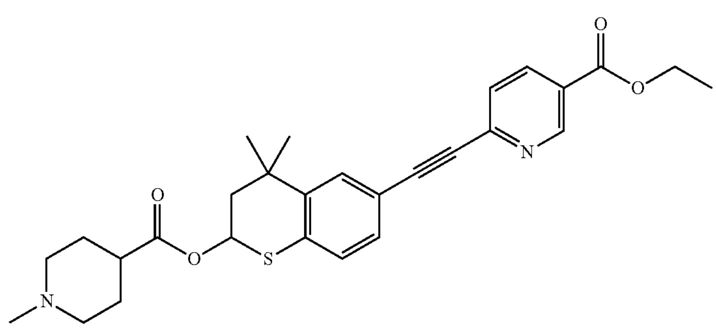 [SMILES: CCOC(=O)c1ccc(C#Cc2ccc3c(c2)C(C)(C)CC(OC(=O)C2CCN(C)CC2)S3)nc1] | MW 492.64 Purity 94.9% |
| 24 | Ethyl 6-[(2-propionyl-4,4-dimethyl-3,4-dihydro-2-thiochrornen-6-yl)ethynyl]pyridine-3-carboxylate | 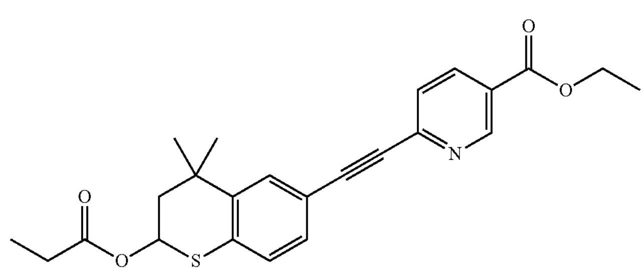 [SMILES: CCOC(=O)c1ccc(C#Cc2ccc3c(c2)C(C)(C)CC(OC(=O)CC)S3)nc1] | MW 423.54 Purity 98.7% |

TABLE 11-continued

| Description | Structure | Notes |
|---|---|---|
| 25 Ethyl 6-[(2-salicylicyl-4,4-dimethyl-3,4-dihydro-2-thiochrornen-6-yl)ethynyl]pyridine-3-carboxylate | 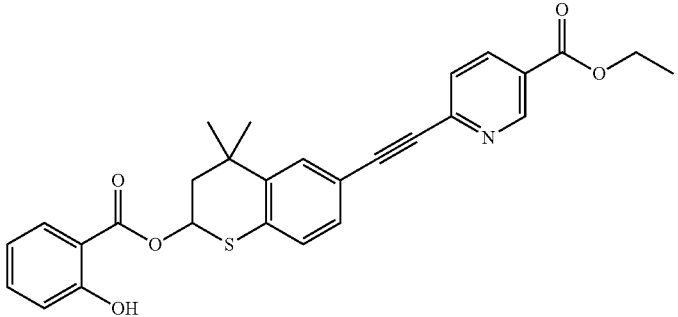 [SMILES: CCOC(=O)c1ccc(C#Cc2ccc3c(c2)C(C)(C)CC(OC(=O)c2ccccc2O)S3)nc1] | MW 487.58 Purity 98.7% |
| 26 Ethyl 6-[(2-(4-tetrahydropyranyloxy-4,4-dimethyl-3,4-dihydro-2-thiochrornen-6-yl)ethynyl]pyridine3-carboxylate | 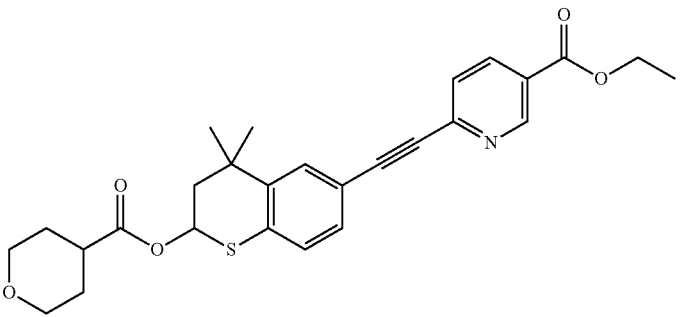 [SMILES: CCOC(=O)c1ccc(C#Cc2ccc3c(c2)C(C)(C)CC(OC(=O)C2CCOCC2)S3)nc1] | MW 479.60 Purity 98.3% |
| 27 Ethyl 6-[(2-monomethyladopyl-4,4-dimethyl-3,4-dihydro-2-thiochrornen-6-yl)ethynyl]pyridine3-carboxylate | 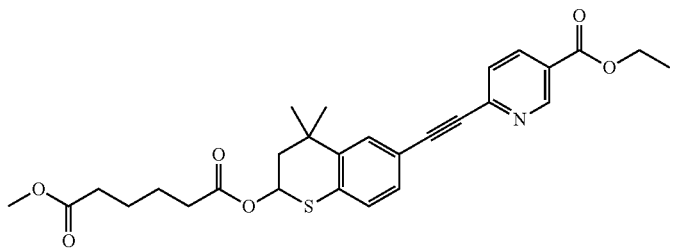 [SMILES: CCOC(=O)c1ccc(C#Cc2ccc3c(c2)C(C)(C)CC(OC(=O)CCCCC(=O)OC)S3)nc1] | MW 509.63 Purity 99.5% |
| 28 Ethyl 6-[(2-(3-monomethylazelauate-4,4-dimethyl-3,4-dihydro-2-thiochrornen-6-yl)ethynyl]pyridine3-carboxylate | 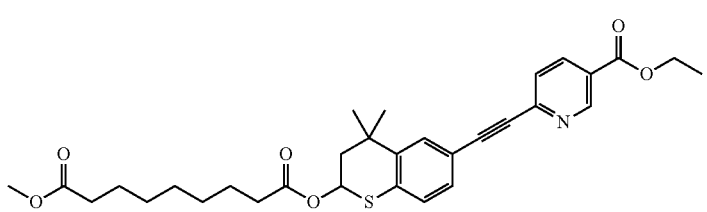 [SMILES: CCOC(=O)c1ccc(C#Cc2ccc3c(c2)C(C)(C)CC(OC(=O)CCCCCCCC(=O)OC)S3)nc1] | MW 551.71 Purity 95.3% |
| 29 6-[2-((S)-2-Amino-3-methyl-butyryloxy)-4,4-dimethyl-thiochroman-6-ylethynyl]-nicotinic acid ethyl ester | 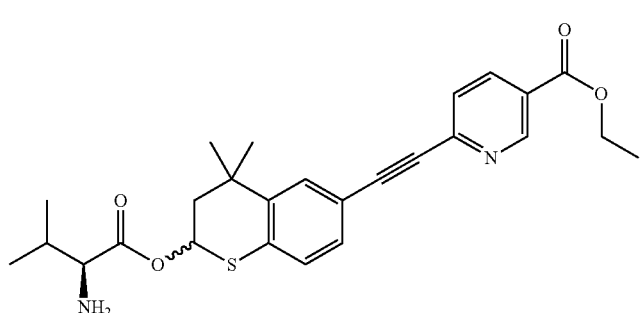 | MW 466.60 Purity 97.8% |

TABLE 12

Qualitative summary of gene expression data from RHE cultures treated with tazarotene derivatives.

| Rank | Compound | Fold Change vs Untreated/OD controls Upregulation/Downregulation | | | | | Ranking Score |
|---|---|---|---|---|---|---|---|
| | | K10 | K19 | Filaggrin | K4 | K13 | |
| 1 | 24 | 14 | 33 | 56 | 74 | 23 | 20 |
| 2 | 23 | 9 | 43 | 18 | 73 | 19 | 23 |
| 3 | 11 | 17 | 21 | 36 | 52 | 20 | 27 |
| 4 | 29 | 9 | 29 | 11 | 71 | 13 | 31 |
| 5 | 15 | 7 | 36 | 8 | 64 | 12 | 33 |
| 6 | 27 | 10 | 41 | 23 | 70 | 19 | 40 |
| 7 | 28 | 6 | 30 | 7 | 77 | 18 | 43 |
| 8 | 14 | 7 | 29 | 11 | 87 | 20 | 44 |
| 9 | 8 | 7 | 18 | 9 | 35 | 7 | 47 |
| 10 | 18 | 4 | 22 | 7 | 60 | 9 | 48 |
| 11 | 10 | 6 | 25 | 6 | 65 | 11 | 48 |
| 12 | 22 | 7 | 12 | 11 | 38 | 10 | 49 |
| 13 | 25 | 3 | 23 | 4 | 103 | 17 | 52 |
| 14 | Tazarotene (3) | 3 | 41 | 3 | 119 | 12 | 52 |
| 15 | 9 | 6 | 17 | 10 | 32 | 5 | 55 |
| 16 | 7 | 19 | 17 | 100 | 23 | 8 | 57 |
| 17 | 12 | 2 | 27 | 1 | 173 | 15 | 59 |
| 18 | 16 | 7 | 20 | 7 | 69 | 9 | 63 |
| 19 | 17 | 3 | 24 | 2 | 180 | 15 | 64 |
| 20 | 6 | 8 | 8 | 16 | 20 | 7 | 64 |
| 21 | 20 | 10 | 15 | 12 | 22 | 6 | 65 |
| 22 | 26 | 4 | 20 | 4 | 90 | 10 | 68 |
| 23 | 5 | 1 | 8 | 1 | 45 | 7 | 76 |
| 24 | 21 | 1 | 2 | 1 | 11 | 3 | 80 |
| 25 | 4 | 2 | 8 | 3 | 29 | 7 | 84 |
| 26 | 13 | 2 | 4 | 1 | 38 | 6 | 89 |
| 27 | 19 | 2 | 2 | 2 | 19 | 2 | 90 |

All publications, including but not limited to patents and patent applications, cited in this specification are herein incorporated by reference as if each individual publication were specifically and individually indicated to be incorporated by reference herein as though fully set forth.

The present invention being thus described, it will be apparent that the same may be modified or varied in many ways. Such modifications and variations are not to be regarded as a departure from the spirit and scope of the present invention, and all such modifications and variations are intended to be included within the scope of the following claims.

What is claimed is:

1. A compound of formula (I):

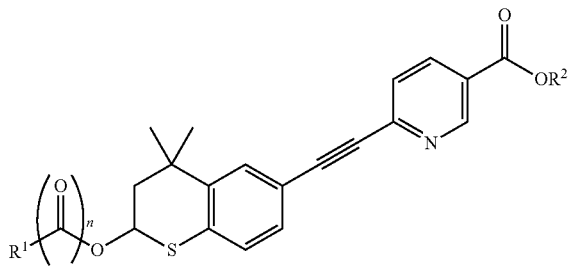

(I)

wherein n is 1;

$R^1$ is hydrogen, optionally substituted $C_{1-18}$ alkyl, optionally substituted $C_{2-18}$ alkenyl, optionally substituted $C_{2-18}$ alkynyl, optionally substituted aryl group, or a optionally substituted cycloalkyl group; and wherein the optional substituents are independently selected from one or more times from halogen; hydroxy; $NR_4R_5$; hydroxy substituted $C_{1-6}$ alkyl; $C_{1-6}$ alkoxy; halosubstituted $C_{1-6}$ alkoxy; halosubstituted $C_{1-6}$ alkyl; $C_{1-6}$ alkyl; —C(O)OR_6, or —OC(O)R_6; and $R^2$ is hydrogen, optionally substituted $C_{1-18}$ alkyl, optionally substituted $C_{2-18}$ alkenyl, optionally substituted $C_{2-18}$ alkynyl, optionally substituted aryl group, optionally substituted cycloalkyl group; or a pharmaceutically acceptable salt thereof and wherein the optional substituents are independently selected from one or more times from halogen; hydroxy; $NR_4R_5$; hydroxy substituted $C_{1-6}$ alkyl; $C_{1-6}$ alkoxy; halosubstituted $C_{1-6}$ alkoxy; halosubstituted $C_{1-6}$ alkyl; $C_{1-6}$ alkyl; —C(O)OR_6, or —OC(O)R_6;

$R_4$ and $R_5$ are independently selected from hydrogen or $C_{1-6}$ alkyl; and $R_6$ is independently selected from hydrogen or $C_{1-6}$ alkyl.

2. The compound according to claim 1, wherein for $R^1$ the optional substituents are selected from hydroxy, $NR_4R_5$, hydroxy substituted $C_{1-6}$ alkyl, or —C(O)OR_6.

3. The compound according to claim 1 wherein $R^1$ is an optionally substituted $C_{1-18}$ alkyl.

4. The compound according to claim 1, wherein $R^1$ is an optionally substituted aryl group.

5. The compound according to claim 1, wherein $R^1$ is an optionally substituted $C_{2-18}$ alkenyl.

6. The compound according to claim 2, wherein when $R^1$ is an optionally substituted $C_{1-18}$ alkyl, $C_{2-18}$ alkenyl, or aryl.

7. The compound according to claim 6, wherein $R^1$ is $C_{1-18}$ alkyl or $C_{1-18}$ alkyl substituted one or more times by hydroxy, $NR_4R_5$, $C_{1-6}$ alkoxy, or —C(O)OR_6.

8. The compound according to claim 4, wherein $R^1$ is an optionally substituted phenyl.

9. The compound according to claim 8, wherein $R^1$ is phenyl.

10. The compound according to claim 1, wherein $R^2$ is hydrogen or $C_{1-6}$ alkyl.

11. The compound according to claim 10, wherein $R^2$ is $C_{1-6}$ alkyl.

12. The compound according to claim 11, wherein $R^2$ is ethyl.

13. The compound according to claim 10, wherein $R^2$ is H.

14. The compound according to claim 1 which is:
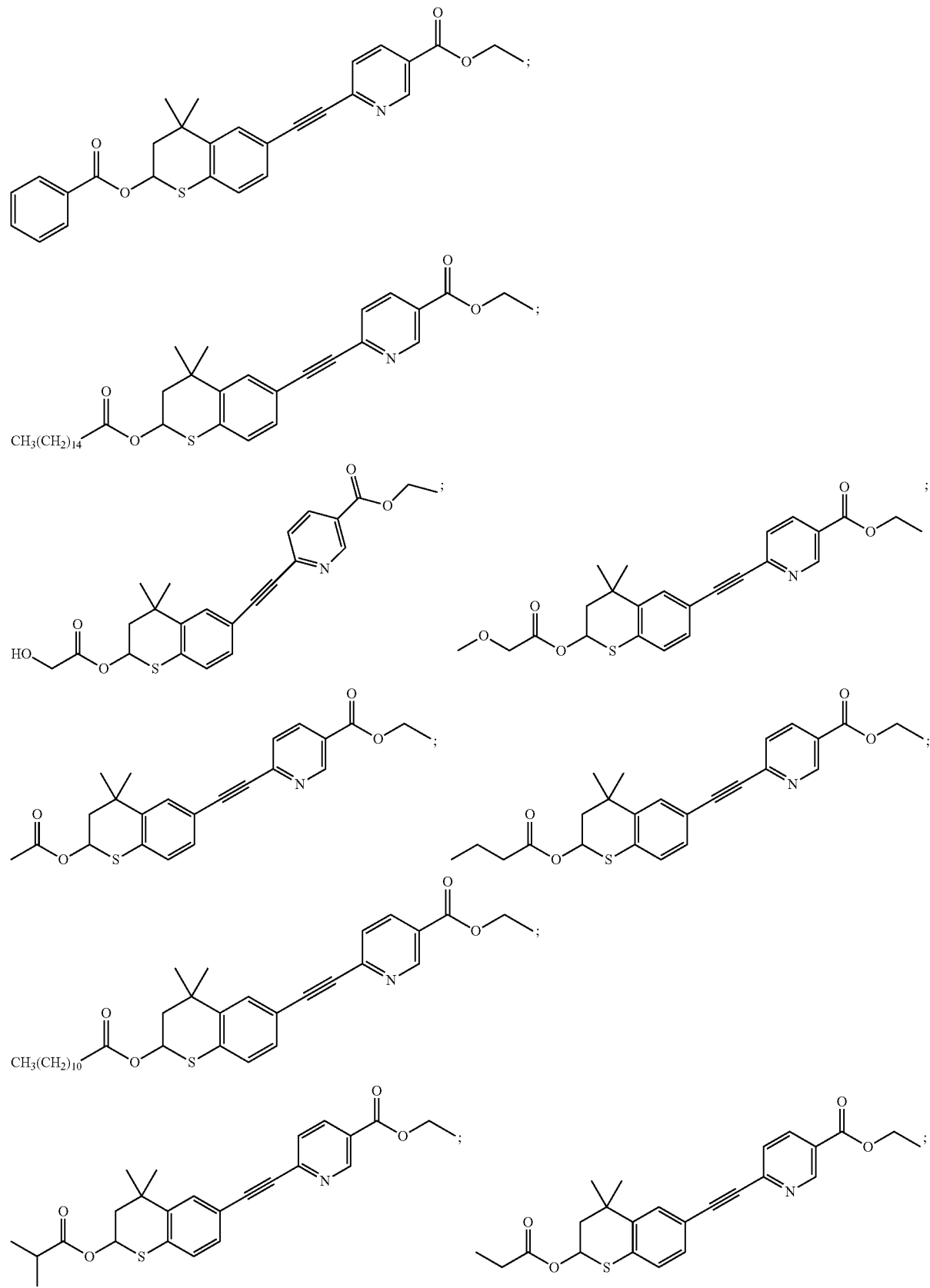

-continued

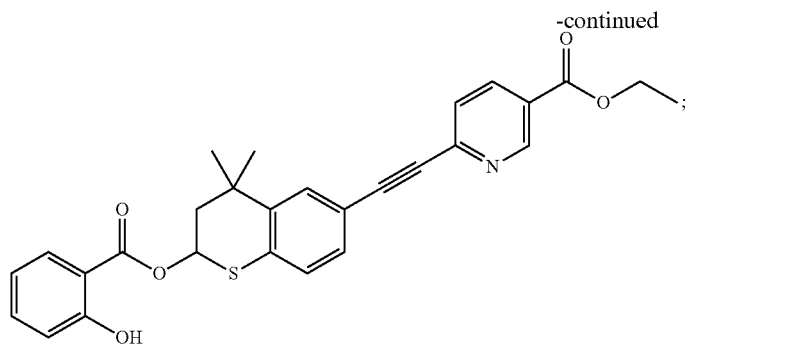

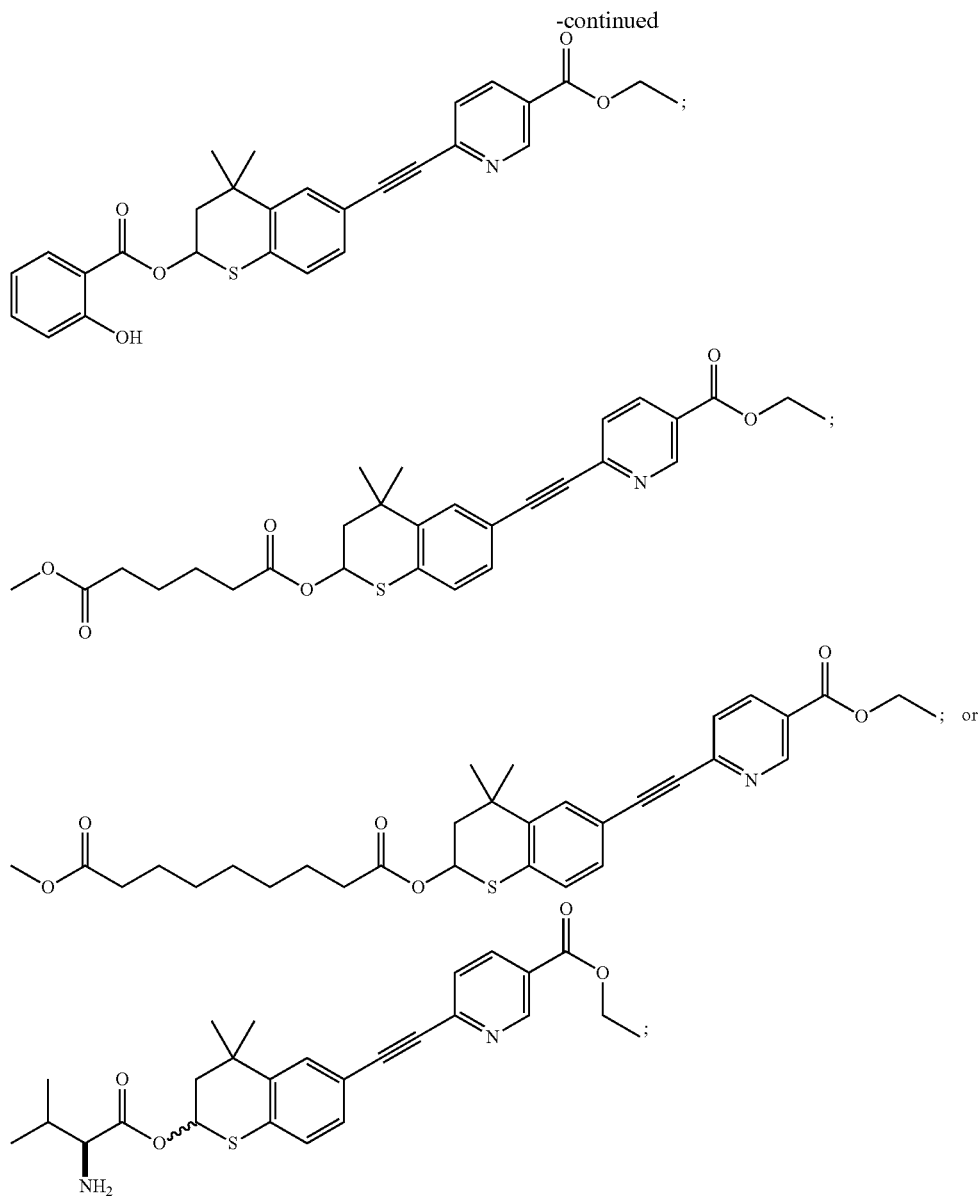

or a pharmaceutically acceptable salt thereof.

15. The compound according to claim 1 which is Tazarotene benzoate

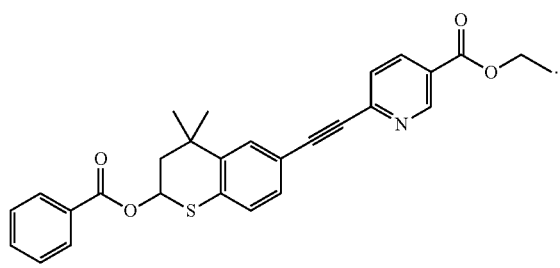 [SMILES: CCOC(=O)c1ccc(C#Cc2ccc3c(c2)C(C)(C)CC(OC(=O)c2ccccc2)S3)nc1]

16. The compound according to claim 15 which is (R)-6-(2-(2-benzoyloxy-4,4-dimethylthiochroman-6-yl)ethynyl) nicotinic acid, ethyl ester.

17. The compound according to claim 15 which is (S)-6-(2-(2-benzoyloxy-4,4-dimethylthiochroman-6-yl)ethynyl) nicotinic acid, ethyl ester.

18. A pharmaceutical composition comprising a compound according to claim 1, and one or more pharmaceutically acceptable carriers or excipients.

19. A pharmaceutical composition comprising a compound according to claim 14, and one or more pharmaceutically acceptable carriers or excipients.

20. A pharmaceutical composition comprising a compound according to claim 15, and one or more pharmaceutically acceptable carriers or excipients.

21. A pharmaceutical composition comprising a compound according to claim 16 and one or more pharmaceutically acceptable carriers or excipients.

22. A pharmaceutical composition comprising a compound according to claim 17 and one or more pharmaceutically acceptable carriers or excipients.

* * * * *